(12) United States Patent
Liu

(10) Patent No.: US 6,565,828 B2
(45) Date of Patent: May 20, 2003

(54) MACROCYCLIC CHELANTS FOR METALLOPHARMACEUTICALS

(75) Inventor: Shuang Liu, Chelmsford, MA (US)

(73) Assignee: Bristol-Myers Squibb Company, Princeton, NJ (US)

(*) Notice: Subject to any disclaimer, the term of this patent is extended or adjusted under 35 U.S.C. 154(b) by 19 days.

(21) Appl. No.: 09/826,549

(22) Filed: Apr. 5, 2001

(65) Prior Publication Data

US 2002/0004032 A1 Jan. 10, 2002

Related U.S. Application Data

(60) Provisional application No. 60/195,234, filed on Apr. 7, 2000.

(51) Int. Cl.[7] .................. A61K 51/00; A61M 36/14
(52) U.S. Cl. .............. 424/1.53; 424/1.11; 424/9.1; 424/1.65; 534/10; 534/14; 534/15
(58) Field of Search .............. 424/1.11, 1.65, 424/1.69, 9.1, 1.49, 1.53; 534/7, 10–16; 514/2, 9

(56) References Cited

U.S. PATENT DOCUMENTS

| | | |
|---|---|---|
| 4,647,447 A | 3/1987 | Gries et al. |
| 4,678,667 A | 7/1987 | Meares et al. |
| 4,885,363 A | 12/1989 | Tweedle et al. |
| 4,923,985 A | 5/1990 | Gansow et al. |
| 5,053,503 A | 10/1991 | Dean et al. |
| 5,250,285 A | 10/1993 | Lauffer et al. |
| 5,310,535 A | 5/1994 | Kruper, Jr. et al. |
| 5,348,954 A | 9/1994 | Almen et al. |
| 5,374,416 A | 12/1994 | Rousseaux et al. |
| 5,409,689 A * | 4/1995 | Winchell et al. .............. 424/9.1 |
| 5,428,154 A | 6/1995 | Gansow et al. |
| 5,428,156 A | 6/1995 | Mease et al. |
| 5,474,756 A | 12/1995 | Tweedle et al. |
| 5,714,604 A * | 2/1998 | Kiefer ................ 540/472 |
| 5,739,323 A | 4/1998 | Kruper, Jr. et al. |
| 5,756,065 A | 5/1998 | Wilson et al. |
| 5,846,519 A | 12/1998 | Tweedle et al. |
| 5,914,095 A | 6/1999 | Watson |
| 5,958,374 A | 9/1999 | Meares et al. |
| 6,005,083 A | 12/1999 | Kasina |

FOREIGN PATENT DOCUMENTS

| | | |
|---|---|---|
| EP | 0292689 B1 | 11/1988 |
| EP | 0374501 | 6/1990 |
| EP | 0382583 B1 | 8/1990 |
| EP | 0565930 | 10/1993 |
| EP | 0872479 A1 | 10/1998 |
| WO | WO 87/05030 | 8/1987 |
| WO | WO 89/01476 | 2/1989 |
| WO | WO 89/11475 | 11/1989 |
| WO | WO 90/06776 | 6/1990 |
| WO | WO 90/12050 | 10/1990 |
| WO | WO 91/07911 | 6/1991 |
| WO | WO 91/14458 | 10/1991 |
| WO | WO 93/06868 | 4/1993 |
| WO | WO 94/00145 | 1/1994 |
| WO | WO 94/03464 | 2/1994 |
| WO | WO 94/26753 | 11/1994 |
| WO | WO 95/05118 | 2/1995 |
| WO | WO 95/26206 | 10/1995 |
| WO | WO 95/31444 | 11/1995 |
| WO | WO 97/31005 | 8/1997 |
| WO | WO 97/32862 | 9/1997 |
| WO | WO 98/30246 | 7/1998 |

OTHER PUBLICATIONS

Baker et al. 1997, J. Am. Chem. Soc. 119, 38, 8749–8755.
Huskens et al., 1997, Inorg. Chem. 36(7), 1495–1503.
Hassfjell et al., 1997, Nucl. Med. Biol. 24, 3, 231–237.
Chavez et al., 1999, Proc. SPIE–Int. Soc. Opt. England, XP002170878.
Mishra et al., 2001, New J. Chem. 25, 2, 336–339.
Sunberg et al., Nature 1974, 250, 587–588.
Krejcarek et al., Biochem. Biophys. Res. Commun. 1977, 77, 2, 581–585.
Hnatowich et al., Science 1983, 220, 613–615.
Moi et al., Anal. Biochem. 1985, 148, 249–253.
Brechbiel et al., Inorg. Chem. 1986, 25, 2772–2781.
Cole et al., Nucl. Med. Biol. 1986, 13, 4, 363–368.
Moi et al., Inorg. Chem. 1987, 26, 3458.
Brechbiel et al., Bioconjugate Chem. 1991, 2, 187–194.
Liu et al., Bioconjugate Chem. 2001, 12, 7–34.

* cited by examiner

Primary Examiner—Dameron L. Jones
(74) Attorney, Agent, or Firm—Paul D. Golian

(57) ABSTRACT

This invention relates to new macrocyclic chelants and metal chelates thereof, methods of preparing the chelants and metal chelates, and pharmaceutical compositions comprising the macrocyclic chelants and metal chelates. This invention relates particularly to the use of the new metal chelates as contrast agents in X-ray or CT, MRI imaging, and radiopharmaceuticals for the diagnosis of cardiovascular disorders, infectious disease and cancer. This invention also relates to new bifunctional chelants (BFCs) for attaching diagnostic metals and therapeutic isotopes to target-specific biomolecules such as proteins, peptides, peptidomimetics, and non-peptide receptor ligands. In addition, the macrocyclic chelants are useful for heavy metal detoxification.

43 Claims, No Drawings

MACROCYCLIC CHELANTS FOR METALLOPHARMACEUTICALS

This application claims the benefit of Provisional Application No. 60/195,234, filed Apr. 7, 2000.

FIELD OF THE INVENTION

This invention relates to new macrocyclic chelants and metal chelates thereof, methods of preparing the chelants and metal chelates, and pharmaceutical compositions comprising the macrocyclic chelants and metal chelates. This invention relates particularly to the use of the new metal chelates as contrast agents in X-ray or CT, MRI imaging, and radiopharmaceuticals for the diagnosis of cardiovascular disorders, infectious disease and cancer. This invention also relates to new bifunctional chelants (BFCs) for attaching diagnostic metals and therapeutic isotopes to target-specific biomolecules such as proteins, peptides, peptidomimetics, and non-peptide receptor ligands. In addition, the macrocyclic chelants are useful for heavy metal detoxification.

BACKGROUND OF THE INVENTION

Medical imaging modalities, such as MRI, X-ray, gamma scintigraphy, and CT scanning, have become extremely important tools in the diagnosis and treatment of various diseases and illness. Imaging of internal body parts relies on the contrast between the targeted organ and the surrounding tissues. The targeted organs or tissues are visible by the use of a particular metallopharmaceutical contast agent. In X-ray and CT diagnostics, increased contrast of internal organs, such as kidney, the urinary tract, the digestive tract, cardiovascular system, tumors, and so forth is obtained by administering a contrast agent which is substantially radiopaque. In conventional proton MRI diagnostics, increased contrast of internal organs and tissues may be obtained by administrating compositions containing paramagnetic metal species, which increase the relaxivity of surrounding water protons. In ultrasound diagnostics, improved contrast is obtained by administering compositions having acoustic inpedances different from that of blood and other tissues. In gamma scintigraphy, contrast of internal organ is obtained by the specific localization of a gamma ray emitting radiopharmaceutical.

Attachment of metal ions to biomolecules (BM) such as antibodies, antibody fragments, peptides, peptidomimetics, and non-peptide receptor ligands leads to useful target-specific diagnostic and therapeutic metallopharmaceuticals. These include fluorescent, radioactive and paramagnetic metal ions attached to proteins that can be used as probes in vivo in biological systems and in vitro in analytical systems as radioimmunoassays. For example, attachment of radionuclides to monoclonal antibodies that recognize tumor associated antigens provides radioimmunoconjugates useful for cancer diagnosis and therapy. The monoclonal antibodies are used as carriers of desired radioisotope to the tumor in vivo.

Radiopharmaceuticals can be classified into two primary classes: those whose biodistribution is determined exclusively by their chemical and physical properties; and those whose ultimate distribution is determined by receptor binding or other biological interactions. The latter class is often called target-specific radiopharmaceuticals. In general, a target specific radiopharmaceutical can be divided into four parts: a targeting molecule, a linker, a BFC, and a radionuclide. The targeting molecule serves as a vehicle, which carries the radionuclide to the receptor site at the diseased tissue or organ. The targeting molecules can be macromolecules such as antibodies; they can also be small biomolecules: peptides, peptidomimetics, and non-peptide receptor ligands. The choice of biomolecule depends upon the targeted disease or disease state. The radionuclide is the radiation source. The selection of radionuclide depends on the intended medical use (diagnostic or therapeutic) of the radiopharmaceutical. Between the targeting molecule and the radionuclide is the BFC, which binds strongly to the metal ion and is covalently attached to the targeting molecule either directly or through a linker. Selection of a BFC is largely determined by the nature and oxidation state of the metallic radionuclide. The linker can be a simple hydrocarbon chain or a long poly(ethylene glycol) (PEG), which is often used for modification of pharmacokinetics. Sometimes, an anionic poly (amino acid) is used to increase the blood clearance and to reduce the background activity, thereby improving the target-to-background ratio.

The use of metallic radionuclides offers many opportunities for designing new radiopharmaceuticals by modifying the coordination environment around the metal with a variety of chelants. The coordination chemistry of the metallic radionuclide will determine the geometry and solution stability of the metal chelate. Different metallic radionuclides have different coodination chemistries, and require BFCs with different donor atoms and ligand frameworks. For "metal essential" radiopharmaceuticals, the biodistribution is exclusively determined by the chemical and physical properties of the metal chelate. For target-specific radiopharmaceuticals, however, the "metal label" is not totally innocent because the target uptake and biodistribution will be affected by not only the targeting biomolecule but also the metal chelate and the linker. This is especially true for radiopharmaceuticals based on small molecules such as peptides due to the fact that in many cases the metal chelate contributes greatly to the overall size and molecular weight. Therefore, the design and selection of the BFC is very important for the development of a new radiopharmaceutical.

The same principle used for target-specific metalloradiopharmaceuticals also applies to target-specific MRI contrast and ultrasound agents. Unlike the target-specific metalloradiopharmaceutical, where the excess unlabeled biomolecule can compete with the radiolabeled BFC-BM conjugate and block the docking of the radiolabeled receptor ligand, MRI and ultrasound contrast agents contain no excess unlabeled BFC-BM conjugate. Saturation of the receptor sites will maximize the contrast between the diseased tissues and normal tissue provided that the use of a relatively large amount of metal-BFC-BM chelate does not cause unwanted side effects.

For a therapeutic radiopharmaceutical or an MRI contrast agent, it is especially important to keep the metal chelate intact under physiological conditions, particularly in the presence of native chelators, such as transferrin, which have very high affinity for trivalent lanthanide metal ions. This requires the chelant to form metal chelate with high thermodynamic stability and kinetic inertness.

Several BFC systems such as ethylenediaminetetraacetic acid (EDTA) and diethylenetriaminepetaacetic acid (DTPA), as well as their derivatives, have been reported to form thermodynamically stable metal chelates. EDTA-based BFCs were first developed by Sunberg et al (*Nature* 1974, 250, 587) in the 1970s. Krejcarek and Tucker (*Biochem. Biophys. Res. Commun.* 1976, 77, 581) developed an activated DTPA analog via a mixed anhydride, which can be linked to proteins. Later, Hnatowich et al (*Science* 1983, 220, 613) used the cyclic anhydride of DTPA for the same purpose. These linear BFCs bond to a variety of metal ions like $^{111}$In or $^{90}$Y and form thermodynamically stable metal chelates. However, metal chelates of linear BFCs are kinetically labile, which contributes to the loss of radionuclide from the metal chelate and often leads to severe bone marrow toxicity. Gansow et al (*Bioconjugate Chem.* 1991, 2, 187; *Inorg. Chem.* 1986, 25, 2772) prepared a series of substituted DTPA analogs, which form metal chelates with improved solution stability.

Polyaza macrocycles have been widely used as chelants for a variety of transition metals. The macrocyclic polyaminocarboxylates such as 1,4,7,10-tetraazacyclo-dodecane-1,4,7,10-tetracetic acid (DOTA) and 1,4,8,11-tetraazacyclo-tetradecane-1,4,8,11-tetracetic acid (TETA) are known to form highly stable metal chelates due to their highly preorganized macrocyclic ligand framework. Their Gd chelates have been widely studied as MRI contrast agents. Examples include gadolinium complexes Gd-DOTA (Dotarem™, Guerbet/France), Gd-HP-DO3A (ProHance™, Bracco/Italy), and Gd-DO3A-butrol (Gadovist™, Schering/Germany).

Macrocyclic chelants such as DOTA have also been used as BFCs for the radiolabeling of proteins (antibodies or antibody fragments) and peptides with various diagnostic and therapeutic radionuclides (such as $^{111}$In and $^{90}$Y). Meares and coworkers were the first to synthesize macrocyclic BFCs (*Anal. Biochem.* 1985, 148, 249; *Nucl. Med. Biol.* 1986, 13, 363; *Inorg. Chem.* 1987, 26, 3458), which form $^{67}$Cu and $^{90}$Y chelates with high thermodynamic stability and kinetic inertness. Macrocyclic chelants with three-dimensional cavities are of particular interest because of the high stability of the metal chelates, the substantial selectivity for certain metal ions, either by enforcing a specific spatial arrangement of donor atoms or by introducing different donor atoms into the ligand backbone, and their capability to adopt a preorganized conformation in the unchelated form. The higher the degree of preorganization of an unchelated ligand, the more stable the complex is.

Preorganization of a polydentate chelant results in not only the high thermodynamic stability but also the increased kinetic inertness of its metal chelate. This has been exemplified by the fact that the half-life for [Gd(DOTA)]$^-$ in 0.1 M HCl is 60.2 h and 2000 years at pH=6.4 while the complex [Gd(DTPA)]$^{2-}$ having comparable thermodynamic stability decomposes rapidly under acidic conditions with a half-life of ~1.0 min. The highly preorganized macrocyclic framework of DOTA forces four acetate chelating arms to adopt such a conformation that the metal ion can be completely wrapped by an $N_4O_4$ donor set. At the same time, this also makes it more difficult for the coordinated acetate to be dissociated from the metal center. Therefore, preorganization should be an important factor in the design of new BFCs for the radiolabeling of biomolecules.

Generally, there are three possible approaches to attach a biomolecule to a DOTA-based chelant. In the first approach, the attachment is at one of the carbon atoms of the macrocyclic chelator backbone. In principle, this will result in formation of eight possible isomers when coordinated to the lanthanide metal ion. In the second approach, the linker is attached to the methylene-carbon atom of one of four acetate chelating arms, which may also result in formation of eight possible isomeric forms. In both approaches, the conjugation of the biomolecule does not lead to a significant change in the thermodynamic stability and kinetic inertness of the metal chelate as compared to those of the DOTA chelate. In the third approach, the biomolecule is conjugated to one of the four acetate groups via a CO—N amide bond. Compared to the carboxylate-O, the carbonyl-O is a relatively weak donor for yttrium and lanthanide metal ions. This often leads to the lower thermodynamic stability of the corresponding metal chelate. However, the kinetic inertness of its metal complex remains relatively unchanged.

In U.S. Pat. No. 4,678,667, Meares et al disclosed a copper chelate conjugate for diagnostic or therapeutic applications. The bifunctional macrocyclic chelants include substituted DOTA, TETA, TRITA, HETA. The linker is at least 8-atom in length and the attachment position of the linker is on the carbon atom of the polyamine macrocycle. In U.S. Pat. No. 5,428,156 disclosed a method of producing DOTA, TETA, DOTA-NHS(NHS=N-hydroxysuccinimide) and TETA-NHS esters for conjugation of biomolecule. Meares et al (WO 95/26206 and U.S. Pat. No. 5,958,374) also disclosed a method for preparing a radionuclide-labeled chelating agent complex. It specifically disclosed DOTA (Gly)$_3$-L-(p-isothiocyanato)-Phe-amide as the BFC. The pendant linkers also include —CH$_2$CO—(AA)m—(AA-Phe-Gly), where AA represents an amino acid diradical, more preferably the glycine diradical —NHCH$_2$CO—. Gansow et al (WO 89/11475, WO 91/14458, U.S. Pat. Nos. 4,923,985 and 5,428,154) disclosed a process of making 4-aminophenyl-DOTA and its use a BFC for the radiolabeling of biomolecules such as antibody. Parker et al (WO 87/05030, WO89/01476, EP 0382583B1 and EP 0382583A1) disclosed a series of DOTA analogs as BFCs, which are coupled with biomolecules such as a protein, especially antibodies, peptides or carbohydrates to form conjugate compounds. The linker and conjugation group is attached to either one of the four acetate chelating arms or one of the carbon atom of the macrocyclic backbone. Watson, et al (WO 90/12050 and WO93/06868) disclosed polychelants and their metal chelates useful in diagnostic imaging and in radiotherapy. The macrocyclic chelant moieties are linked to the backbone moiety (dendrimer or polylysine) via an amide-bond. In U.S. Pat. No. 5,053,053, Dean et al also disclosed a series of DOTA and DO3A analogs as BFCs. For DO3A-based BFCs, the conjugation group is connected to a linker attached to one of the four amine-nitrogen atoms. For DOTA derivatives, the linker group is connected to either one of carbon-atoms on the macrocyclic backbone or the methylene-carbon atom of one of the four acetate chelating arms. Tweedle, et al (EP 0292689 A2/A3; U.S. Pat. Nos. 4,885,363, 5,474,756, and 5,846,519) disclosed metal chelates, particularly those of neutral charge, for MRI contrast imaging. It also disclosed DO3A analogs as BFCs for the radiolabeling of biomolecules. Kruper et al (U.S. Pat. Nos. 5,310,535 and 5,739,323) disclosed the DOTA analogs as BFCs for the radiolabeling of proteins. The linker is connected to the acetate chelating arm and the conjugation group is on a benzene ring. It was shown that the DOTA monoamide has better kinetic inertness because of less bone uptake. Kubomura et al (AU9335519 and EP 0565930A1) disclosed the use of DO3A-CH$_2$CONHCH$_2$CH$_2$NH$_2$ as the BFC, and the metal chelates of BFC-BM conjugates as diagnostic or therapeutic pharmaceuticals. Gozzini et al (WO 97/32862) disclosed a new class of polychelants, their chelates with metal ions and their physiologically acceptable salts, which can be used, either as they are or in association or formulation with other components, for diagnostic imaging in general or specific contrast agents for specific tissues, organs or body compartments. It specifically discloses DOTA as the BFC, and a process of making these macrocyclic chelants with DO3A-

CH₂CONHCH₂CH₂CHO and poly(amino acids) as key intermediates. Wilson et al (U.S. Pat. No. 5,756,065) also disclosed DOTA analogs as BFCs. The conjugation group is attached to a benzene ring and the linker group is connected to one of the four acetate chelating arms. Almen et al. (U.S. Pat. No. 5,348,954) discloses heterocyclic chelating agents for use in heavy metal detoxification. Watson (U.S. Pat. No. 5,914,095) also discloses polychelants for use in metal detoxification.

SUMMARY OF THE INVENTION

The present invention provides macrocyclic chelants containing a substituted pyridinone moiety. These macrocyclic chelants are unique for several reasons. The hydroxy group of the pyridinone heterocycle has a higher pKa value than the carboxylic group and the hydroxy-O is a better donor atom than the corresponding carbonyl-O atom in a DOTA-biomolecule conjugate when bonded to "hard" trivalent lanthanide metal ions. These macrocyclic chelants will form anionic metal chelates with higher hydrophilicity, which is beneficial for improved pharmacokinetics. The pyridinone binding unit is bidentate, and is available to form a "pre-chelate" before the metal ion goes into the coordination cavity of the macrocycle. This, in return, will result in improved radiolabeling kinetics. Like DOTA, the macrocyclic chelants are expected to form stable complexes with trivalent metal ions such as $In^{3+}$, $Y^{3+}$, $Sm^{3+}$, $Gd^{3+}$, $Dy^{3+}$, $Ho^{3+}$, $Yb^{3+}$, and $Lu^{3+}$. Unlike phenols, the pyridinone ring is radiolytically stable, which is very important to maintain the solution stability of therapeutic radiopharmaceuticals.

The present invention also provides macrocyclic chelants containing a succinimide or phthalimide functional group. The succinimide or phthalimide group is connected to one of the four amine-nitrogen atoms of the macrocycle via a $C_1$–$C_3$ alkylene linker in such a way that the carbonyl-O atom of the succinamide or phthalimide group is available to coordinate the lanthanide metal ions to form 8- or 9-coordinated metal chelates. Unlike macrocyclic chelants with substituent(s) on the acetate chelating arm or macrocyclic backbone, macrocyclic chelants containing a succinimide or phthalimide group form metal chelates with only two isomers. Due to the presence of DO3A chelating unit, macrocyclic chelants containing a succinimide or phthalimide group will form lanthanide metal chelates with high thermodynamic stability and kinetic inertness.

The present invention also provides macrocyclic chelants containing a linker group, such as phosphotriester, phosphodiester, phosphodiestermonoamide-, and phosphomonoester-diamide. Like carbonyl-O and carboxylate-O atoms, the phosphonyl-O and phosphonate-O are also good donor atoms for "hard", trivalent lanthanide metal ions. These macrocyclic chelants form either neutral or anionic metal chelates with trivalent metal ions such as $In^{3+}$, $Y^{3+}$, $Sm^{3+}$, $Gd^{3+}$, $Dy^{3+}$, $Ho^{3+}$, $Yb^{3+}$, and $Lu^{3+}$.

DETAILED DESCRIPTION OF THE INVENTION

The present invention provides macrocyclic chelants that can rapidly form highly stable metal chelates useful as diagnostic or therapeutic metalloradiopharmaceuticals, or magnetic resonance imaging contrast agents, or X-ray or CT contrast agents. The macrocyclic chelants can also serve as bifunctional chelators (BFCs) for attaching metal ions to bio-directing groups including proteins, peptides, peptidomimetics, and non-peptides that bind in vivo to a receptor or enzyme that is expressed or up-regulated at a site or in a disease state. The target specific metallopharmaceuticals of the present invention are useful in the diagnosis of disease by MRI, X-ray, CT imaging or scintigraphy or in the treatment of disease by systemic radiotherapy.

[1] Thus, in a first embodiment, the present invention provides a novel compound of formula:

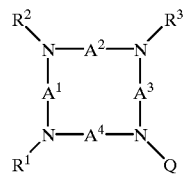

or pharmaceutically acceptable salts thereof, wherein:

$R^1$, $R^2$, and $R^3$ are independently selected from: $C_1$–$C_{10}$ alkyl substituted with 1–5 $R^4$, $C_1$–$C_{10}$ fluoroalkyl substituted with 1–5 $R^4$, $C_2$–$C_{10}$ alkenyl substituted with 1–5 $R^4$, $C_2$–$C_{10}$ fluoroalkenyl substituted with 1–5 $R^4$, and aryl substituted with 1–5 $R^4$, fluoroaryl substituted with 1–5 $R^4$;

$R^4$ is independently selected at each occurrence from: C(=O)$R^5$, S(O)$_2$O$R^5$, C(=O)O$R^5$, C(=O)N$R^6R^7$, PO(O$R^6$)(O$R^7$);

$R^5$, $R^6$ and $R^7$ are independently selected from: H, $C_1$–$C_{10}$ alkyl substituted with 0–5 $R^8$, $C_2$–$C_{10}$ alkenyl substituted with 0–5 $R^8$, $C_3$–$C_{10}$ cycloalkyl substituted with 0–5 $R^8$, $C_1$–$C_{10}$ fluoroalkyl substituted with 0–5 $R^8$, $C_2$–$C_{10}$ fluoroalkenyl substituted with 0–5 $R^8$, aryl substituted with 0–5 $R^8$, and fluoroaryl substituted with 0–3 $R^8$, said $C_1$–$C_{10}$ alkyl and $C_2$–$C_{10}$ alkenyl groups optionally interrupted with —O—, —S—, —NH—, —S(O)—, —S(O)$_2$-, —P(O)(O$R^9$)O—, —P(O)(NH$R^9$)O—, —C(O)NH—, —NHC(O)—, —NHC(O)NH—, or —NHC(S)NH—;

or alternatively, $R^6$ and $R^7$ may be taken together, with the atoms through which they are attached, to form a $C_3$–$C_{10}$ cycloalkyl substituted with 0–5 $R^8$, $C_3$–$C_{10}$ cycloalkenyl substituted with 0–5 $R^8$, aryl substituted with 0–5 $R^8$, or fluoroaryl substituted with 0–5 $R^8$; said $C_3$–$C_{10}$ alkyl and $C_3$–$C_{10}$ cycloalkenyl groups optionally interrupted with —O—, —S—, —N$R^9$—, —S(O)—, —S(O)$_2$-, —P(O)(O$R^9$)—, —P(O)(O$R^9$)O—, —P(O)(NH$R^9$)—, —P(O)(NH$R^9$)O—, —C(O)NH—, —NHC(O)—, —NHC(O)NH—, or —NHC(S)NH—;

$R^8$ is independently selected at each occurrence from: H, —OH, —NH$R^9$, —C(=O)$R^9$, —OC(=O)$R^9$, —OC(=O)O$R^9$, —C(=O)O$R^9$, —C(=O)N($R^9$)$_2$, —PO(O$R^9$)$_2$, —S$R^9$, —SO$R^9$, —SO$_2R^9$, —NHC(=O)$R^9$, —NHC(=O)NH$R^9$, —CH$_2$O$R^9$, and —NHC(=S)NH$R^9$;

$R^9$ is independently selected at each occurrence from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkenyl, $C_1$–$C_6$ fluoroalkenyl, benzyl, fluorobenzyl, phenyl, and fluorophenyl;

$A^1$, $A^2$, $A^3$, and $A^4$ are independently —(C$R^5R^5$)$_n$—, wherein n is 2 or 3.

Q is a functional group selected from:

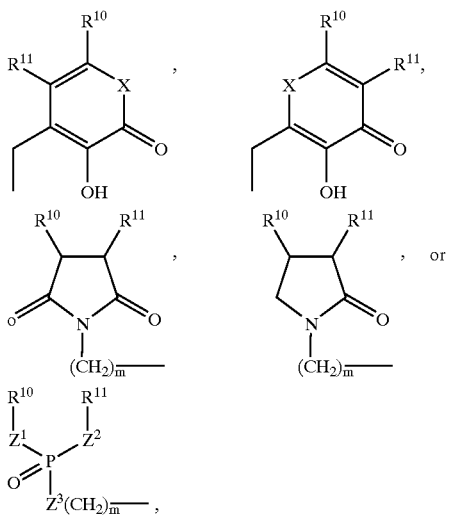

wherein $R^{10}$ and $R^{11}$ are independently selected at each occurrence from: H, $C_1$–$C_{10}$ alkyl substituted with 0–5 $R^{12}$, $C_3$–$C_{10}$ cycloalkyl substituted with 0–5 $R^{12}$, $C_1$–$C_{10}$ fluoroalkyl substituted with 0–5 $R^{12}$, $C_2$–$C_{10}$ alkenyl substituted with 0–5 $R^{12}$, $C_3$–$C_{10}$ cycloalkenyl substituted with 0–5 $R^{12}$, $C_2$–$C_{10}$ fluoroalkenyl substituted with 0–5 $R^{12}$, and aryl substituted with 0–5 $R^{12}$, or, alternatively, $R^{10}$ and $R^{11}$ may be taken together, with the atoms through which they are attached, to form a cyclic ring system, said ring system selected from: $C_3$–$C_{10}$ cycloalkyl substituted with 0–5 $R^{12}$, and aryl substituted with 0–3 $R^{12}$;

m is 1–3;

$R^{12}$ is independently selected at each occurrence from the group: $COR^{13}$, $C(=O)OR^{13}$, $C(=O)N(R^{13})_2$, $PO(OR^{13})_2$, $OR^{13}$, and $SO_2OR^{13}$, $R^{13}$ is independently selected at each occurrence from the group: H, and $C_1$–$C_6$ alkyl;

X is selected from O or $NR^5$; and $Z^1$, $Z^2$, and $Z^3$ are independently selected from: O, NH, $CH_2NH$, and a direct bond.

[2] A preferred embodiment of the present invention is a compound of embodiment [1], wherein:

$R^1$, $R^2$, and $R^3$ are independently selected from: $C_1$–$C_3$ alkyl substituted with 1–2 $R^4$, $C_1$–$C_3$ fluoroalkyl substituted with 1–2 $R^4$, aryl substituted with 1–2 $R^4$, and fluoroaryl substituted with 1–2 $R^4$;

$R^5$, $R^6$ and $R^7$ are independently selected from: H, $C_1$–$C_3$ alkyl substituted with 0–2 $R^8$, $C_3$–$C_6$ cycloalkyl substituted with 0–2 $R^8$, $C_1$–$C_3$ fluoroalkyl substituted with 0–2 $R^8$, and aryl substituted with 0–2 $R^8$;

or alternatively, $R^6$ and $R^7$ may be taken together, with the atoms through which they are attached, to form a $C_3$–$C_6$ cycloalkyl substituted with 0–2 $R^8$, $C_3$–$C_6$ cycloalkenyl substituted with 0–2 $R^8$, or an aryl substituted with 0–2 $R^8$;

$R^9$ is independently selected at each occurrence from: H, $C_1$–$C_3$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, and fluorophenyl;

$A^1$, $A^2$, $A^3$, and $A^4$ are —$(CR^5R^5)_2$—;

$R^{10}$ and $R^{11}$ are independently selected at each occurrence from: H, $C_1$–$C_3$ alkyl substituted with 0–2 $R^{12}$, $C_3$–$C_6$ cycloalkyl substituted with 0–2 $R^{12}$, $C_1$–$C_3$ fluoroalkyl substituted with 0–2 $R^{12}$, $C_2$–$C_3$ alkenyl substituted with 0–2 $R^{12}$, $C_3$–$C_6$ cycloalkenyl substituted with 0–2 $R^{12}$, $C_2$–$C_3$ fluoroalkenyl substituted with 0–2 $R^{12}$, and aryl substituted with 0–2 $R^{12}$, or, alternatively, $R^{10}$ and $R^{11}$ may be taken together, with the atoms through which they are attached, to form a $C_3$–$C_{10}$ cycloalkyl group substituted with 0–2 $R^{12}$, or aryl group sustituted with 0–2 $R^{12}$;

$R^{13}$ is H or $C_1$–$C_3$ alkyl; and $Z^1$, $Z^2$, and $Z^3$ are independently selected from: O, NH, and a direct bond.

[3] A more preferred embodiment of the present invention is a compound of embodiment [1] or [2], wherein:

$R^1$, $R^2$, and $R^3$ are —$CH_2R^4$;

$R^4$ is independently elected at each occurrence from: COOH, $PO_3H_2$, $SO_3H$, and $C(=O) NR^6R^7$;

$A^1$, $A^2$, and $A^3$ are —$(CH_2)_2$—; and

Q is a functional group of the formula:

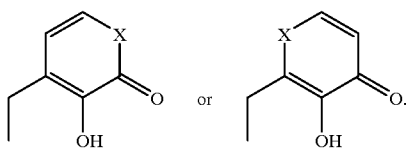

[4] Another more preferred embodiment of the present invention is a compound of embodiment [2], wherein:

$R^1$, $R^2$, and $R^3$ are —$CH_2R^4$;

$R^4$ is independently elected at each occurrence from: COOH, $PO_3H_2$, $SO_3H$, and $C(=O)NR^6R^7$;

$A^1$, $A^2$, $A^3$ and $A^4$ are —$(CH_2)_2$—; and

Q is a functional group of the formula:

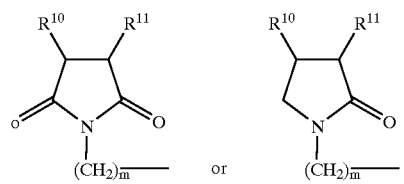

wherein $R^{10}$ and $R^{11}$ are taken together to form a phenyl group substituted with 0–2 $R^{12}$.

[5] Another more preferred embodiment of the present invention is a compound of embodiment [2], wherein:

$R^1$, $R^2$, and $R^3$ are —$CH_2R^4$;

$R^4$ is independently elected at each occurrence from: COOH, $PO_3H_2$, $SO_3H$, and $C(=O)NR^6R^7$;

$A^1$, $A^2$, $A^3$, and $A^4$ are —$(CH_2)_2$—; and

Q is a functional group of the formula:

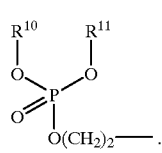

[6] A further preferred embodiment of the present invention is a compound of embodiment [2] of the formula:

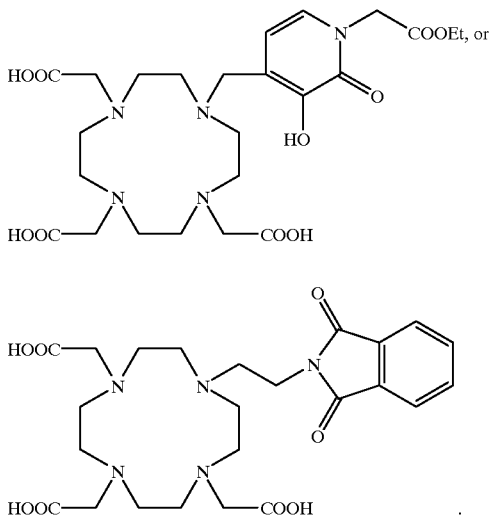

[7] In a second embodiment, the present invention provides a novel metal chelate complex comprising a compound according to any one of embodiments [1]-[6] complexed to a metal ion of atomic number 21–31, 39–49, 50, 56–80, 82, 83, 90.

[8] In another embodiment, the present invention provides a novel metal chelate complex comprising a compound according to any one of embodiments [1]-[6] complexed to a radionuclide selected from: $^{64}Cu$, $^{62}Cu$, $^{60}Cu$, $^{67}Cu$, $^{67}Ga$, $^{68}Ga$, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$, and $^{188}Re$.

[9] In another embodiment, the present invention provides a metal chelate complex according to embodiment [7] or [8] of the formula:

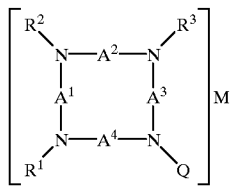

or pharmaceutically acceptable salts thereof, wherein:
M is X or $X^1$; wherein:
X is a radionuclide selected from: $^{64}Cu$, $^{62}Cu$, $^{60}Cu$, $^{67}Cu$, $^{67}Ga$, $^{68}Ga$, $^{99m}Tc$, $^{111}In$, $^{90}Y$, $^{149}Pr$, 153Sm, 159Gd, $^{166}Ho$, $^{169}Yb$, $^{177}Lu$, $^{186}Re$, and $^{188}Re$;
$X^1$ is a metal ion of atomic number 21–31, 39–49, 50, 56–80, 82, 83, 90; wherein:
$R^1$, $R^2$, and $R^3$ are independently selected from: $C_1$–$C_{10}$ alkyl substituted with 1–5 $R^4$, $C_1$–$C_{10}$ fluoroalkyl substituted with 1–5 $R^4$, $C_2$–$C_{10}$ alkenyl substituted with 1–5 $R^4$, $C_2$–$C_{10}$ fluoroalkenyl substituted with 1–5 $R^4$ and aryl substituted with 1–5 $R^4$, fluoroaryl substituted with 1–5 $R^4$;
$R^4$ is independently selected at each occurrence from: —C(=O) $R^5$, —S(O)$_2$O$R^5$—C(=O)O$R^5$—C(=O) N$R^6R^7$, —PO(O$R^6$) (O$R^7$);
$R^5$, $R^6$ and $R^7$ are independently selected from: H, $C_1$–$C_{10}$ alkyl substituted with 0–5 $R^8$, $C_2$–$C_{10}$ alkenyl substituted with 0–5 $R^8$, $C_3$–$C_{10}$ cycloalkyl substituted with 0–5 $R^8$, $C_1$–$C_{10}$ fluoroalkyl substituted with 0–5 $R^8$, $C_2$–$C_{10}$ fluoroalkenyl substituted with 0–5 $R^8$, aryl substituted with 0–5 $R^8$, and fluoroaryl substituted with 0–3 $R^8$, said $C_1$–$C_{10}$ alkyl and $C_2$–$C_{10}$ alkenyl groups optionally interrupted with —O—, —S—, —NH—, —S(O)—, —S(O)$_2$—, —P(O)(O$R^9$)O—, —P(O)(NH$R^9$)O—, —C(O) NH—, —NHC(O)—, —NHC(O)NH—, —NHC(S) NH—;

or alternatively, $R^6$ and $R^7$ may be taken together, with the atoms through which they are attached, to form a $C_3$–$C_{10}$ cycloalkyl substituted with 0–5 $R^8$, $C_3$–$C_{10}$ cycloalkenyl substituted with 0–5 $R^8$, aryl substituted with 0–5 $R^8$, or fluoroaryl substituted with 0–5 $R^8$; said $C_3$–$C_{10}$ alkyl and $C_3$–$C_{10}$ cycloalkenyl groups optionally interrupted with —O—, —S—, —N$R^9$—, —S(O)—, —S(O)$_2$—, —P(O) (O$R^9$)—, —P(O)(O$R^9$)O—, —P(O)(NH$R^9$)—, —P(O) (NH$R^9$)O—, —C(O)NH—, —NHC(O)—, —NHC(O) NH—, or —NHC(S)NH—;

$R^8$ is independently selected at each occurrence from: H, OH, NH$R^9$, C(=O)$R^9$, OC(=O)$R^9$, OC(=O)O$R^9$, C(=O)O$R^9$, C(=O)N($R^9$)$_2$, PO(O$R^9$)$_2$, S$R^9$, SO$R^9$, SO$_2R^9$, NHC(=O)$R^9$, NHC(=O)NH$R^9$, CH$_2$O$R^9$, and NHC(=S)NH$R^9$;

$R^9$ is independently selected at each occurrence from: H, $C_1$—$C_6$ alkyl, $C_3$—$C_6$ cycloalkyl, $C_1$—$C_6$ fluoroalkyl, $C_1$—$C_6$ alkenyl, $C_3$—$C_6$ cycloalkyl, $C_1$-$C_6$ fluoroalkenyl, benzyl, fluorobenzyl, phenyl, and fluorophenyl;

$A^1$, $A^2$, $A^3$, and $A^4$ are independently —(C$R^5R^5$)$_n$—, wherein n is 2 or 3.

Q is a functional group selected from:

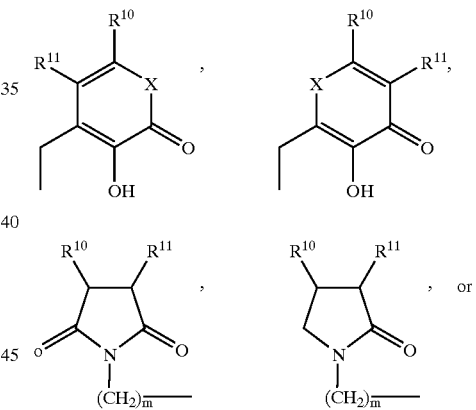

wherein $R^{10}$ and $R^{11}$ are independently selected at each occurrence from: H, $C_1$–$C_{10}$ alkyl substituted with 0–5 $R^{12}$, $C_3$–$C_{10}$ cycloalkyl substituted with 0–5 $R^{12}$, $C_1$–$C_{10}$ fluoroalkyl substituted with 0–5 $R^{12}$, $C_2$–$C_{10}$ alkenyl substituted with 0–5 $R^{12}$, $C_3$–$C_{10}$ cycloalkenyl substituted with 0–5 $R^{12}$, $C_2$–$C_{10}$ fluoroalkenyl substituted with 0–5 $R^{12}$, and aryl substituted with 0–5 $R^{12}$, or, alternatively, $R^{10}$ and $R^{11}$ may be taken together, with the atoms through which they are attached, to form a cyclic ring system, said ring system selected from: $C_3$–$C_{10}$ cycloalkyl substituted with 0–5 $R^{12}$ and aryl substituted with 0–3 $R^{12}$;

m is 1–3;

$R^{12}$ is independently selected at each occurrence from the group: —$COR^{13}$, —$C(=O)OR^{13}$, —$C(=O)N(R^{13})_2$, —$PO(OR^{13})_2$, —$OR^{13}$, and —$SO_2OR^{13}$;

$R^{13}$ is independently selected at each occurrence from the group: H, and $C_1$–$C_6$ alkyl;

X is selected from —O— or —$NR^5$—; and $Z^1$, $Z^2$, and $Z^3$ are independently selected from: —O—, —NH—, —$CH_2NH$—, and a direct bond.

[10] Another preferred embodiment of the present invention is a metal chelate complex of embodiment [9], wherein:

$R^1$, $R^2$, and $R^3$ are independently selected from: $C_1$–$C_3$ alkyl substituted with 1–2 $R^4$, $C_1$–$C_3$ fluoroalkyl substituted with 1–2 $R^4$, aryl substituted with 1–2 $R^4$, and fluoroaryl substituted with 1–2 $R^4$;

$R^5$, $R^6$ and $R^7$ are independently selected from: H, $C_1$–$C_3$ alkyl substituted with 0–2 $R^8$, $C_3$–$C_6$ cycloalkyl substituted with 0–2 $R^8$, $C_1$–$C_3$ fluoroalkyl substituted with 0–2 $R^8$, and aryl substituted with 0–2 $R^8$;

or alternatively, $R^6$ and $R^7$ may be taken together, with the atoms through which they are attached, to form a $C_3$–$C_6$ cycloalkyl substituted with 0–2 $R^8$, $C_3$–$C_6$ cycloalkenyl substituted with 0–2 $R^8$, or an aryl substituted with 0–2 $R^8$;

$R^9$ is independently selected at each occurrence from: H, $C_1$–$C_3$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, and fluorophenyl;

$A^1$, $A^2$, $A^3$, and $A^4$ are —$(CR^5R^5)_2$—;

$R^{10}$ and $R^{11}$ are independently selected at each occurrence from: H, $C_1$–$C_3$ alkyl substituted with 0–2 $R^{12}$, $C_3$–$C_6$ cycloalkyl substituted with 0–2 $R^{12}$, $C_1$–$C_3$ fluoroalkyl substituted with 0–2 $R^{12}$, $C_2$–$C_3$ alkenyl substituted with 0–2 $R^{12}$, $C_3$–$C_6$ cycloalkenyl substituted with 0–2 $R^{12}$, $C_2$–$C_3$ fluoroalkenyl substituted with 0–2 $R^{12}$, and aryl substituted with 0–2 $R^{12}$, or, alternatively, $R^{10}$ and $R^{11}$ may be taken together, with the atoms through which they are attached, to form a $C_3$–$C_{10}$ cycloalkyl group substituted with 0–2 $R^{12}$, or aryl group sustituted with 0–2 $R^{12}$;

$R^{13}$ is H or $C_1$–$C_3$ alkyl; and $Z^1$, $Z^2$, and $Z^3$ are independently selected from: O, NH, and a direct bond.

[11] Another more preferred embodiment of the present invention is a metal chelate complex of embodiment [10], wherein:

$R^1$, $R^2$, and $R^3$ are —$CH_2R^4$;

$R^4$ is independently elected at each occurrence from: COOH, —$PO_3H_2$, —$SO_3H$, and —$C(=O)NR^6R^7$;

$A^1$, $A^2$, $A^3$, and $A^4$ are —$(CH_2)_2$—; and

Q is a functional group of the formula:

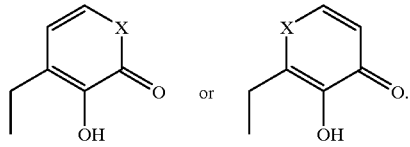

[12] Another more preferred embodiment of the present invention is a metal chelate complex of embodiment [10], wherein:

$R^1$, $R^2$, and $R^3$ are 13 $CH_2R^4$;

$R^4$ is independently elected at each occurrence from: —COOH, —$PO_3H_2$, —$SO_3H$, and —$C(=O)NR^6R^7$;

$A^1$, $A^2$, $A^3$, and $A^4$ are —$(CH_2)_2$—; and

Q is a functional group of the formula:

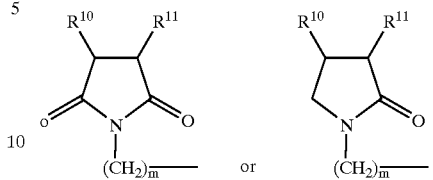

wherein $R^{10}$ and $R^{11}$ are taken together to form a phenyl group substituted with 0–2 $R^{12}$.

[13] Another more preferred embodiment of the present invention is a metal chelate complex of embodiment [10], wherein:

$R^1$ $R^2$ and $R^3$ are —$CH_2R^4$;

$R^4$ is independently elected at each occurrence from: COOH, $PO_3H_2$, $SO_3H$, and —$C(=O)NR^6R^7$;

$A^1$, $A^2$, $A^{3,}$ and $A^4$ are —$(CH_2)_2$—; and

Q is a functional group of the formula:

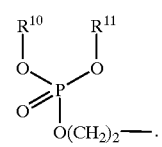

[14] Another further preferred embodiment of the present invention is a metal chelate complex of embodiment [10] that is:

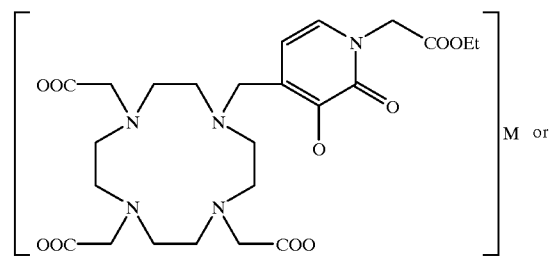

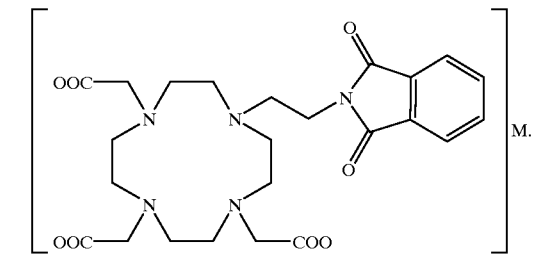

[15] Another further preferred embodiment of the present invention is a metal chelate complex of embodiment [10] selected from the group consisting of:

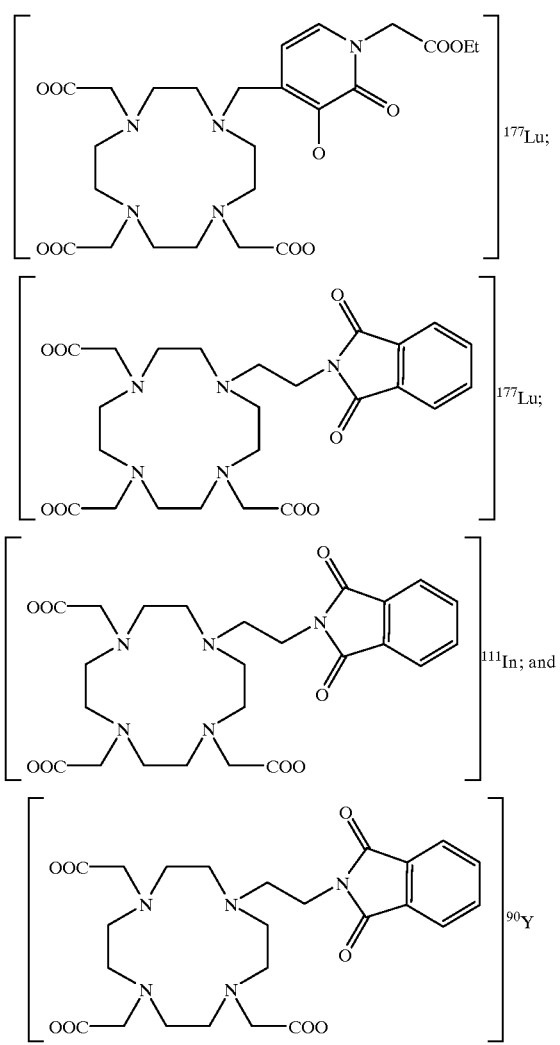

[16] A third embodiment of the present invention is a novel conjugate of the formula:

$$C_h\text{—}L_n\text{—}BM,$$

or pharmaceutically acceptable salts thereof, wherein, $C_h$ is a chelator of formula:

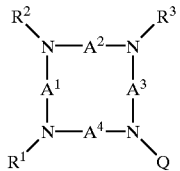

wherein:

$R^1$, $R^2$, and $R^3$ are independently selected from: $C_1$–$C_{10}$ alkyl substituted with 1–5 $R^4$, $C_1$–$C_{10}$ fluoroalkyl substituted with 1–5 $R^4$, $C_2$–$C_{10}$ alkenyl substituted with 1–5 $R^4$, $C_2$–$C_{10}$ fluoroalkenyl substituted with 1–5 $R^4$, and aryl substituted with 1–5 $R^4$, fluoroaryl substituted with 1–5 $R^4$;

$R^4$ is independently selected at each occurrence from: C(=O)$R^5$, S(O)$_2$O$R^5$, C(=O)O$R^5$, C(=O)N$R^6R^7$, PO(O$R^6$)(O$R^7$);

$R^5$, $R^6$ and $R^7$ are independently selected from: H, a direct bond to $L_n$, $C_1$–$C_{10}$ alkyl substituted with 0–5 $R^8$, $C_2$–$C_{10}$ alkenyl substituted with 0–5 $R^8$, $C_3$–$C_{10}$ cycloalkyl substituted with 0–5 $R^8$, $C_1$–$C_{10}$ fluoroalkyl substituted with 0–5 $R^8$, $C_2$–$C_{10}$ fluoroalkenyl substituted with 0–5 $R^8$, aryl substituted with 0–5 $R^8$, and fluoroaryl substituted with 0–3 $R^8$, said $C_1$–$C_{10}$ alkyl and $C_2$–$C_{10}$ alkenyl groups optionally interrupted with O, S, NH, S(O), S(O)$_2$, P(O)(O$R^9$)O, P(O)(NH$R^9$)O, C(O)NH, NHC(O), NHC(O)NH, NHC(S)NH;

or alternatively, $R^6$ and $R^7$ may be taken together, with the atoms through which they are attached, to form a $C_3$–$C_{10}$ cycloalkyl substituted with 0–5 R8, $C_3$–$C_{10}$ cycloalkenyl substituted with 0–5 $R^8$, aryl substituted with 0–5 $R^8$, or fluoroaryl substituted with 0–5 $R^8$; said $C_3$–$C_{10}$ alkyl and $C_3$–$C_{10}$ cycloalkenyl groups optionally interrupted with —O—, —S—, —N$R^9$—, —S(O)—, —S(O)$_2$—, —P(O)(O$R^9$)—, —P(O)(O$R^9$)O—, —P(O)(NH$R^9$)—, —P(O)(NH$R^9$)O—, —C(O)NH—, —NHC(O)—, —NHC(O)NH—, or —NHC(S)NH—;

$R^8$ is independently selected at each occurrence from: —H, —OH, —NH$R^9$, —C(=O)$R^9$, —OC(=O)$R^9$, —OC(=O)O$R^9$, —C(=O)O$R^9$, —C(=O)N($R^9$)$_2$, —PO(O$R^9$)$_2$, —S$R^9$, —SO$R^9$, —SO$_2R^9$, —NHC(=O)$R^9$, NHC(=O)NH$R^9$, —CH$_2$O$R^9$, —NHC(=S)NH$R^9$, and a direct bond to $L_n$;

$R^9$ is independently selected at each occurrence from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, fluorophenyl, and a direct bond to $L_n$;

$A^1$, $A^2$, $A^3$, and $A^4$ are independently —(C$R^5R^5$)$_n$—, wherein n is 2 or 3.

Q is a functional group selected from:

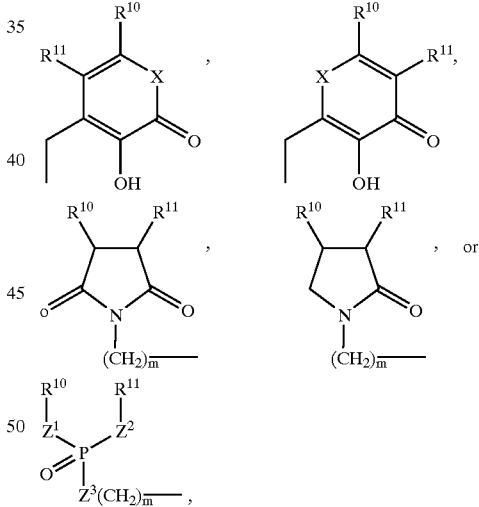

wherein:

$R^{10}$ and $R^{11}$ are independently selected at each occurrence from: H, $C_1$–$C_{10}$ alkyl substituted with 0–5 $R^{12}$, $C_3$–$C_{10}$ cycloalkyl substituted with 0–5 $R^{12}$, $C_1$–$C_{10}$ fluoroalkyl substituted with 0–5 $R^{12}$, $C_2$–$C_{10}$ alkenyl substituted with 0–5 $R^{12}$, $C_3$–$C_{10}$ cycloalkyl substituted with 0–5 $R^{12}$, $C_2$–$C_{10}$ fluoroalkenyl substituted with 0–5 $R^{12}$, aryl substituted with 0–5 $R^{12}$, and a direct bond to $L_n$;

or, alternatively, $R^{10}$ and $R^{11}$ may be taken together with the atoms through which they are attached, to form a cyclic ring system, said ring system selected from: $C_3$–$C_{10}$ cycloalkyl substituted with 0–5 $R^{12}$, and aryl substituted with 0–3 $R^{12}$;

m is 1–3;

R$^{12}$ is independently selected at each occurrence from the group: —COR$^{13}$, —C(=O)OR$^{13}$, —C(=O)N(R$^{13}$)$_2$, —PO(OR$^{13}$)$_2$, —OR$^{13}$, —SO$_2$OR$^{13}$, and a direct bond to L$_n$;

R$^{13}$ is independently selected at each occurrence from the group: H, C$_1$–C$_6$ alkyl, and a direct bond to L$_n$;

X is selected from O or NR$^5$;

Z$^1$, Z$^2$, and Z$^3$ are independently selected at each occurrence from: O, NH, CH$_2$NH, and a direct bond;

L$_n$ is a linking group of formula:

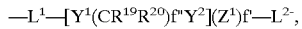

L$^1$ is —[(CH$_2$)$_g$Z$^1$]$_{g'}$-(CR$^{19}$R$^{20}$)$_{g''}$—;
L$^2$ is —(CR$^{19}$R$^{20}$)$_{g''}$-[Z$^1$(CH$_2$)$_g$]$_{g'}$—;
g is independently 0–10;
g' is independently 0–1;
g" is independently 0–10;
f is independently 0–10;
f' is independently 0–10;
f" is independently 0–1;

Y$^1$ and Y$^2$ are independently selected, at each occurrence, from: a direct bond, —O—, —NR$^{20}$—, —C(=O)—, —C(=O)O—, —OC(=O)O—, —C(=O)NH—, —C(=NR$^{20}$)—, —S—, —S(O)—, —S(O)$_2$—, —NHC(=O)—, —(NH)$_2$C(=O)—, and —(NH)$_2$C(=S)—;

R$^{19}$ and R$^{20}$ are independently selected at each occurrence from: H, a direct bond to BM, C$_1$–C$_{10}$ alkyl substituted with 0–5 R$^{21}$, and alkaryl wherein the aryl is substituted with 0–5 R$^{21}$;

R$^{21}$ is independently selected at each occurrence from the group: —NHR$^{22}$, —C(=O)R$^{22}$, —OC(=O)R$^{22}$, —OC(=O)OR$^{22}$, —C(=O)OR$^{22}$, —C(=O)NR$^{22}$, —CN, —SR$^{22}$, —S(O)R$^{22}$, —S(O)$_2$R$^{22}$, —NHC(=O)R$^{22}$, —NHC(=O)NHR$^{22}$, —NHC(=S)NHR$^{22}$, and a direct bond to BM;

R$^{22}$ is independently selected at each occurrence from the group: H, C$_1$–C$_6$ alkyl, benzyl, phenyl, and a direct bond to BM; and BM is a biologically active targeting molecule selected from the group: IIb/IIIa receptor ligands, fibrin binding peptides, leukocyte binding peptides, chemotactic peptides, LTB$_4$ receptor antagonists, somatostatin analogs, selectin binding peptides, vitronectin receptor antagonists, growth factor receptor antagonists, tyrosine kinase inhibitors, matrix metalloproteinase inhibitors, oligonucleotides, fatty acids, nitroimidazoles, and carbohydrates.

[17] Another preferred embodiment of the present invention is a conjugate of embodiment [16], wherein, R$^1$, R$^2$, and R$^3$ are independently selected from: C$_1$–C$_3$ alkyl substituted with 1–2 R$^4$, C$_1$–C$_3$ fluoroalkyl substituted with 1–2 R$^4$, aryl substituted with 1–2 R$^4$, and fluoroaryl substituted with 1–2 R$^4$;

R$^5$, R$^6$ and R$^7$ are independently selected from: H, a direct bond to L$_n$, C$_1$–C$_3$ alkyl substituted with 0–2 R$^8$, C$_3$–C$_6$ cycloalkyl substituted with 0–2 R$^8$, C$_1$–C$_3$ fluoroalkyl substituted with 0–2 R$^8$, and aryl substituted with 0–2 R$^8$;

or alternatively, R$^6$ and R$^7$ may be taken together, with the atoms through which they are attached, to form a C$_3$–C$_6$ cycloalkyl substituted with 0–2 R$^8$, C$_3$–C$_6$ cycloalkenyl substituted with 0–2 R$^8$, or aryl substituted with 0–2 R$^8$;

R$^9$ is independently selected at each occurrence from: H, a direct bond to L$_n$, C$_1$–C$_3$ alkyl, C$_3$–C$_6$ cycloalkyl, C$_1$–C$_6$ fluoroalkyl, C$_1$–C$_6$ alkenyl, C$_3$–C$_6$ cycloalkenyl, C$_1$–C$_6$ fluoroalkenyl, benzyl, fluorobenzyl, phenyl, and fluorophenyl;

A$^1$, A$^2$, A$^3$ and A$^4$ are —(CR$^5$R$^5$)$_2$—;

R$^{10}$ and R$^{11}$ are independently selected at each occurrence from: H, a direct bond to L$_n$, C$_1$–C$_3$ alkyl substituted with 0–2 R$^{12}$, C$_3$–C$_6$ cycloalkyl substituted with 0–2 R$^{12}$, C$_1$–C$_3$ fluoroalkyl substituted with 0–2 R$^{12}$, C$_2$–C$_3$ alkenyl substituted with 0–2 R$^{12}$, C$_3$–C$_6$ cycloalkenyl substituted with 0–2 R$^{12}$, C$_2$–C$_3$ fluoroalkenyl substituted with 0–2 R$^{12}$, and aryl substituted with 0–2 R$^{12}$, or, alternatively, R$^{10}$ and R$^{11}$ may be taken together to form a C$_3$–C$_{10}$ cycloalkyl group substituted with 0–2 R$^{12}$, or ortho-aryl group sustituted with 0–2 R$^{12}$;

R$^{13}$ is H or C$_1$–C$_3$ alkyl; and Z$^1$, Z$^2$, and Z$^3$ are independently selected from: O, NH, and a direct bond.

[18] Another more preferred embodiment of the present invention is a conjugate of embodiment [17], wherein:

R$^1$, R$^2$, and R$^3$ are CH$_2$R$^4$;
R$^4$ is independently elected at each occurrence from: —COOH, —PO$_3$H$_2$, —SO$_3$H, and —C(=O)NR$^6$R$^7$;
A$^1$, A$^2$, A$^3$, and A$^4$ are —(CH$_2$)$_2$—; and
Q is a functional group of the formula:

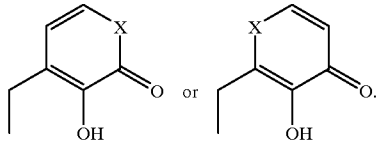

[19] Another more preferred embodiment of the present invention is a conjugate of embodiment [17], wherein:

R$^1$, R$^2$, and R$^3$ are —CH$_2$R$^4$;
R$^4$ is independently elected at each occurrence from: COOH, PO$_3$H$_2$, SO$_3$, and C(=O)NR$^6$R$^7$;
A$^1$, A$^2$, A$^3$ and A$^4$ are —(CH2)$_2$—; and
Q is a functional group of the formula:

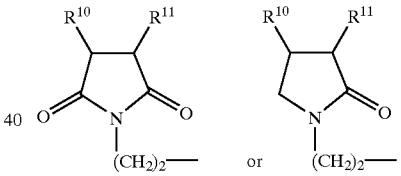

wherein:
R$^{10}$ and R$^{11}$ are taken together to form a phenyl group substituted with 0–2 R$^{12}$.

[20] Another more preferred embodiment of the present invention is a conjugate of embodiment [17], wherein:

R$^1$, R$^2$, and R$^3$ are CH$_2$R$^4$;
R$^4$ is independently elected at each occurrence from: —COOH, —PO$_3$H$_2$, —SO$_3$H, and —C(=O)NR$^6$R$^7$;
A$^1$, A$^2$, A$^3$, and A$^4$ are —(CH$_2$)$_2$-; and
Q is a functional group of the formula:

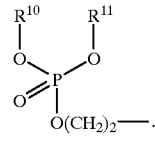

[21] A fourth embodiment of the present invention is a novel metallopharmaceutical comprising a conjugate according to embodiment [16] chelated with a radionuclide selected from: $^{64}$Cu, $^{62}$Cu, $^{60}$Cu, $^{67}$Cu, $^{67}$Ga, $^{68}$Ga, $^{99m}$Tc, $^{111}$In, $^{90}$Y, $^{149}$Pr, $^{153}$Sm, $^{159}$Gd, $^{166}$Ho, $^{169}$Yb, $^{177}$Lu, $^{186}$Re, and $^{188}$Re.

[22] A fourth embodiment of the present invention is a novel metallopharmaceutical comprising a cojugate according to embodiment [16] chelated with a metal ion of atomic number 21–31, 39–49, 50, 56–80, 82, 83, 90.

[23] A fourth embodiment of the present invention is a novel metallopharmaceutical according to embodiment [21] or [22] of the formula:

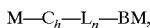

or pharmaceutically acceptable salts thereof, wherein:
M is X or $X^1$; wherein:
X is a radionuclide selected from: $^{64}$Cu, $^{62}$Cu, $^{60}$Cu, $^{67}$Cu, $^{67}$Ga, $^{68}$Ga, $^{99m}$TC, $^{111}$In, $^{90}$Y, $^{149}$Pr, $^{153}$Sm, $^{159}$Gd, $^{166}$Ho, $^{169}$Yb, $^{177}$Lu, $^{186}$Re, and $^{188}$Re;
$X^1$ is a metal ion of atomic number 21–31, 39–49, 50, 56–80, 82, 83, 90;
$C_h$ is a chelator of formula:

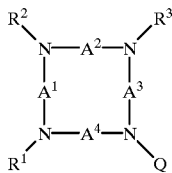

wherein:
$R^1$, $R^1$, and $R^3$ are independently selected from: $C_1$–$C_{10}$ alkyl substituted with 1–5 $R^4$, $C_1$–$C_{10}$ fluoroalkyl substituted with 1–5 $R^4$, $C_2$–$C_{10}$ alkenyl substituted with 1–5 $R^4$, $C_2$–$C_{10}$ fluoroalkenyl substituted with 1–5 $R^4$, and aryl substituted with 1–5 $R^4$, fluoroaryl substituted with 1–5 $R^4$;
$R^4$ is independently selected at each occurrence from:
—C(=O)$R^5$, S(O)$_2$O$R^5$, —C(=O)O$R^5$, —C(=O)N$R^6R^7$, PO(O$R^6$)(O$R^7$) $R^5$, $R^6$ and $R^7$ are independently selected from: H, a direct bond to $L_n$, $C_1$–$C_{10}$ alkyl substituted with 0–5 $R^8$, $C_2$–$C_{10}$ alkenyl substituted with 0–5 $R^8$, $C_3$–$C_{10}$ cycloalkyl substituted with 0–5 $R^8$, $C_1$–$C_{10}$ fluoroalkyl substituted with 0–5 $R^8$, $C_2$–$C_{10}$ fluoroalkenyl substituted with 0–5 $R^8$, aryl substituted with 0–5 $R^8$, and fluoroaryl substituted with 0–3 $R^8$, said $C_1$–$C_{10}$ alkyl and $C_2$–$C_{10}$ alkenyl groups optionally interrupted with —O—, —S—, —NH—, —S(O)—, —S(O)$_2$-, —P(O)(O$R^9$)O—, —P(O)(NH$R^9$)O—, —C(O)NH—, —NHC(O)—, —NHC(O)NH—, —NHC(S)NH—;
or alternatively, $R^6$ and $R^7$ may be taken together, with the atoms through which they are attached, to form a $C_3$–$C_{10}$ cycloalkyl substituted with 0–5 $R^8$, $C_3$–$C_{10}$ cycloalkenyl substituted with 0–5 $R^8$, aryl substituted with 0–5 $R^8$, or fluoroaryl substituted with 0–5 $R^8$; said $C_3$–$C_{10}$ alkyl and $C_3$–$C_{10}$ cycloalkenyl groups optionally interrupted with O, S, N$R^9$, S(O), S(O)$_2$, P (O) (O$R^9$), P(O) (O$R^9$)O, P(O)(NH$R^9$), P(O) (NH$R^9$)O, —C(O)NH, NH—C(O), NH—C(O)NH, NH—C(S)NH;
$R^8$ is independently selected at each occurrence from: H, OH, NH$R^9$, C(=O)$R^9$, OC(=O)$R^9$, OC(=O)O$R^9$, C(=O)O$R^9$, C(=O)N($R^9$)$_2$, PO(O$R^9$)$_2$, S$R^9$, SO$R^9$, SO$_2R^9$, NHC(=O)$R^9$, NHC(=O)NH$R^9$, CH$_2$O$R^9$, NHC(=S)NH$R^9$, and a direct bond to $L_n$;
$R^9$ is independently selected at each occurrence from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, fluorophenyl, and a direct bond to $L_n$;
$A^1$, $A^2$, $A^3$, and $A^4$ are independently —(C$R^5R^5$)$_n$—, wherein n is 2 or 3.

Q is a functional group of the formula:

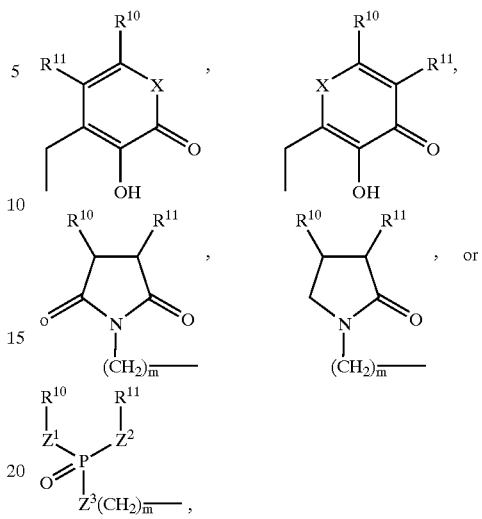

wherein:
$R^{10}$ and $R^{11}$ are independently selected at each occurrence from: H, $C_1$–$C_{10}$ alkyl substituted with 0–5 $R^{12}$, $C_3$–$C_{10}$ cycloalkyl substituted with 0–5 $R^{12}$, $C_1$–$C_{10}$ fluoroalkyl substituted with 0–5 $R^{12}$, $C_2$–$C_{10}$ alkenyl substituted with 0–5 $R^{12}$, $C_3$–$C_{10}$ cycloalkenyl substituted with 0–5 $R^{12}$, $C_2$–$C_{10}$ fluoroalkenyl substituted with 0–5 $R^{12}$, aryl substituted with 0–5 $R^{12}$, and a direct bond to $L_n$;
or, alternatively, $R^{10}$ and $R^{11}$ may be taken together, with the atoms through which they are attached, to form a cyclic ring system, said ring system selected from: $C_3$–$C_{10}$ cycloalkyl substituted with 0–5 $R^{12}$, and aryl substituted with 0–3 $R^{12}$;
m is 1–3;
$R^{12}$ is independently selected at each occurrence from the group: CO$R^{13}$, C(=O)O$R^{13}$, C(=O)N($R^{13}$)$_2$, PO(O$R^{13}$)$_2$, O$R^{13}$, SO$_2$O$R^{13}$, and a direct bond to $L_n$;
$R^{13}$ is independently selected at each occurrence from the group: H, $C_1$–$C_6$ alkyl, and a direct bond to $L_n$;
X is selected from O or N$R^5$;
$Z^1$, $Z^2$, and $Z^3$ are independently selected at each occurrence from: O, NH, CH$_2$NH, and a direct bond;
$L_n$, is a linking group of formula:

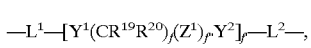

$L^1$ is —[(CH$_2$)$_gZ^1$]$_{g'}$—(C$R^{19}R^{20}$)$_{g''}$—;
$L^2$ is —(C$R^{19}R^{20}$)$_g$—[$Z^1$(CH$_2$)$_g$]$_{g'}$—;
g is independently 0–10;
g' is independently 0–1;
g" is independently 0–10;
f is independently 0–10;
f' is independently 0–10;
f" is independently 0–1;
$Y^1$ and $Y^2$ are independently selected at each occurrence from: a direct bond, —O—, —N$R^{20}$—, —C=O—, —C(=O)O—, —OC(=O)O—, —C(=O)NH—, —C(=N$R^{20}$)—, —S—, —S(O)—, —S(O)$_2$—, —NHC(=O)—, —(NH)$_2$C(=O)—, and —(NH)$_2$(C=S)—;
$R^{19}$ and $R^{20}$ are independently selected at each occurrence from: H, a direct bond to BM, $C_1$–$C_{10}$ alkyl substituted with 0–5 $R^{21}$, and alkaryl wherein the aryl is substituted with 0–5 $R^{21}$;
$R^{21}$ is independently selected at each occurrence from the group: —NH$R^{22}$, —C(=O)$R^{22}$, —OC(=O)$R^{22}$, —OC (=O)OR$^{22}$, —C(=O)OR$^{22}$, —C(=O)NR$_2^{22}$, —CN, —SR$^{22}$, —S(O)R$^{22}$, —S(O)$_2$R$^{22}$, —NHC(=O)R$^{22}$, —NHC(=O)NHR$^{22}$, —NHC(=S)NHR$^{22}$, and a direct bond to BM;

R$^{22}$ is independently selected at each occurrence from the group: H, C$_1$–C$_6$ alkyl, benzyl, phenyl, and a direct bond to BM; and BM is a biologically active targeting molecule selected from the group: IIb/IIIa receptor ligands, fibrin binding peptides, leukocyte binding peptides, chemotactic peptides, LTB$_4$ receptor antagonists, somatostatin analogs, selectin binding peptides, vitronectin receptor antagonists, growth factor receptor antagonists, tyrosine kinase inhibitors, matrix metalloproteinase inhibitors, oligonucleotides, fatty acids, nitroimidazoles, and carbohydrates.

[24] Another preferred embodiment of the present invention is a metallopharmaceutical of embodiment [23], wherein, R$^1$, R$^2$, and R$^3$ are independently selected from: C$_1$–C$_3$ alkyl substituted with 1–2 R$^4$, C$_1$–C$_3$ fluoroalkyl substituted with 1–2 R$^4$, aryl substituted with 1–2 R$^4$, and fluoroaryl substituted with 1–2 R$^4$;

R$^5$, R$^6$ and R$^7$ are independently selected from: H, a direct bond to L$_n$, C$_1$–C$_3$ alkyl substituted with 0–2 R$^8$, C$_3$–C$_6$ cycloalkyl substituted with 0–2 R$^8$, C$_1$–C$_3$ fluoroalkyl substituted with 0–2 R$^8$, and aryl substituted with 0–2 R$^8$;

or alternatively, R$^6$ and R$^7$ may be taken together, with the atoms through which they are attached, to form a C$_3$–C$_6$ cycloalkyl substituted with 0–2 R$^8$, C$_3$–C$_6$ cycloalkenyl substituted with 0–2 R$^8$, or aryl substituted with 0–2 R$^8$;

R$^9$ is independently selected at each occurrence from: H, a direct bond to L$_n$, C$_1$–C$_3$ alkyl, C$_3$–C$_6$ cycloalkyl, C$_1$–C$_6$ fluoroalkyl, C$_1$–C$_6$ alkenyl, C$_3$–C$_6$ cycloalkyl, C$_1$–C$_6$ fluoroalkenyl, benzyl, fluorobenzyl, phenyl, and fluorophenyl;

A$^1$, A$^2$, A$^3$, and A$^4$ are —(CR$^5$R$^5$)$_2$—;

R$^{10}$ and R$^{11}$ are independently selected at each occurrence from: H, a direct bond to L$_n$, C$_1$–C$_3$ alkyl substituted with 0–2 R$^{12}$, C$_3$–C$_6$ cycloalkyl substituted with 0–2 R$^{12}$, C$_1$–C$_3$ fluoroalkyl substituted with 0–2 R$^{12}$, C$_2$–C$_3$ alkenyl substituted with 0–2 R$^{12}$, C$_3$–C$_6$ cycloalkenyl substituted with 0–2 R$^{12}$, C$_2$–C$_3$ fluoroalkenyl substituted with 0–2 R$^{12}$, and aryl substituted with 0–2 R$^{12}$, or, alternatively, R$^{10}$ and R$^{11}$ may be taken together, with the atoms through which they are attached, to form a C$_3$–C$_{10}$ cycloalkyl group substituted with 0–2 R$^{12}$, or ortho-aryl group sustituted with 0–2 R$^{12}$;

R$^{13}$ is H or C$_1$–C$_3$ alkyl; and

Z$^1$, Z$^2$, and Z$^3$ are independently selected from: O, NH, and a direct bond.

[25] Another more preferred embodiment of the present invention is a metallopharmaceutical of embodiment [24], wherein:

R$^1$ R$^2$ and R$^3$ are CH$_2$R$^4$;

R$^4$ is independently elected at each occurrence from: —COOH, —PO$_3$H$_2$, —SO$_3$H, and —C(=O)NR$^6$R$^7$;

A$^1$, A$^2$, A$^3$, and A$^4$ are —(CH$_2$)$_2$—; and

Q is a functional group of the formula:

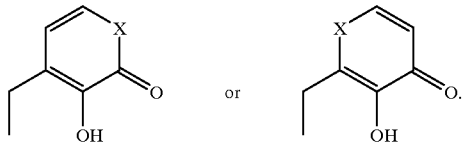

[26] Another more preferred embodiment of the present invention is a metallopharmaceutical of embodiment [24], wherein:

R$^1$, R$^2$, and R$^3$ are —CH$_2$R$^4$;

R$^4$ is independently elected at each occurrence from: —COOH, —PO$_3$H$_2$, —SO$_3$H, and —C(=O)NR$^6$R$^7$;

A$^1$, A$^2$, A$^3$, and A$^4$ are —(CH$_2$)$_2$—; and

Q is a functional group of the formula:

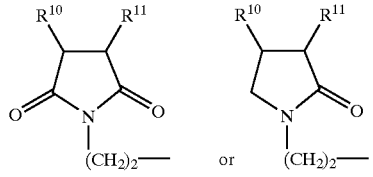

wherein R$^{10}$ and R$^{11}$ are taken together to form a phenyl group substituted with 0–2 R$^{12}$.

[27] Another more preferred embodiment of the present invention is a metallopharmaceutical of embodiment [24], wherein:

R$^1$, R$^2$, and R$^3$ are —CH$_2$R$^4$;

R$^4$ is independently elected at each occurrence from: COOH, PO$_3$H$_2$, SO$_3$H, and C(=O)NR$^6$R$^7$;

A$^1$, A$^2$, A$^3$, and A$^4$ are —(CH$_2$)$_2$—; and

Q is a functional group of the formula:

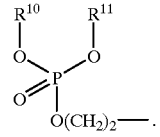

[28] Another preferred embodiment of the present invention is a radiopharmaceutical composition comprising a metallopharmaceutical of embodiment [21] and a pharmaceutically acceptable carrier.

[29] Another preferred embodiment of the present invention is a method of treating cancer in a patient comprising administering to a patient in need thereof a therapeutically effective amount of a radiopharmaceutical composition according to embodiment [28], wherein BM is a biologically active targeting molecule selected from the group: vitronectin receptor antagonists, growth factor receptor antagonists, matrix metalloproteinase inhibitors and tyrosine kinase inhibitors.

[30] Another preferred embodiment of the present invention is a method of diagnosing thromboembolic disorders or atherosclerosis in a patient, comprising:
  (i) administering to said patient a diagnostic effective amount of a metallopharmaceutical according to embodiment [23]; and
  (ii) generating a radioimage of at least a part of said patient's body;
wherein BM is a IIb/IIIa receptor ligand or fibrin binding peptide; and M is $^{62}$Cu, $^{60}$Cu, $^{67}$Ga, $^{68}$Ga, $^{99m}$Tc, or $^{111}$In.

[31] Another preferred embodiment of the present invention is a method of diagnosing thromboembolic disorders or atherosclerosis in a patient, comprising:
  (i) administering to said patient a diagnostic effective amount of a metallopharmaceutical according to embodiment [23]; and
  (ii) generating a MRI image of at least a part of said patient's body;
wherein BM is a IIb/IIIa receptor ligand or fibrin binding peptide; and
M is paramagnetic metal ion of atomic number 21–29, 42–44 or 58–70.

[32] Another preferred embodiment of the present invention is a method of diagnosing thromboembolic disorders or atherosclerosis in a patient, comprising:
  (i) administering to said patient a diagnostic effective amount of a metallopharmaceutical according to embodiment [23]; and
  (ii) generating an X-ray or CT image of at least a part of said patient's body;
wherein BM is a IIb/IIIa receptor ligand or fibrin binding peptide; and
M is heavy metal ion of atomic number 21–31, 39–49, 50, 56–80, 82, 83, 90.

[33] Another preferred embodiment of the present invention is a method of diagnosing infection, inflammation or transplant rejection in a patient, comprising:
  (i) administering to said patient a diagnostic effective amount of a metallopharmaceutical according to embodiment [23]; and
  (ii) generating a radioimage of at least a part of said patient's body;
wherein BM is selected from the group consisting of a leukocyte binding peptide, a chemotactic peptide, and a LTB$_4$ receptor antagonist; and
M is $^{62}$Cu, $^{60}$Cu, $^{67}$Ga, $^{68}$Ga, $^{99m}$Tc, or $^{111}$In.

[34] Another preferred embodiment of the present invention is a method of diagnosing infection, inflammation or transplant rejection in a patient, comprising:
  (i) administering to said patient a diagnostic effective amount of a metallopharmaceutical according to embodiment [23]; and
  (ii) generating a MRI image of at least a part of said patient's body;
wherein BM is selected from the group consisting of a leukocyte binding peptide, a chemotactic peptide, and a LTB$_4$ receptor antagonist; and
M is paramagnetic metal ion of atomic number 21–29, 42–44 or 58–70.

[35] Another preferred embodiment of the present invention is a method of diagnosing infection, inflammation or transplant rejection in a patient, comprising:
  (i) administering to said patient a diagnostic effective amount of a metallopharmaceutical according to embodiment [23]; and
  (ii) generating an X-ray or CT image of at least a part of said patient's body;
wherein BM is selected from the group consisting of a leukocyte binding peptide, a chemotactic peptide, and a LTB$_4$ receptor antagonist; and
M is heavy metal ion of atomic number 21–31, 39–49, 50, 56–80, 82, 83, 90.

[36] Another preferred embodiment of the present invention is a method of detecting new angiogenic vasculature in a patient, comprising:
  (i) administering to said patient a diagnostic effective amount of a metallopharmaceutical according to embodiment [23]; and
  (ii) generating a radioimage of at least a part of said patient's body;
wherein BM is a vitronectin receptor antagonist, a somatostatin analog, or a growth factor receptor antagonist; and
M is $^{62}$Cu, $^{60}$Cu, $^{67}$Ga, $^{68}$Ga, $^{99m}$Tc, or $^{111}$In.

[37] Another preferred embodiment of the present invention is a method of detecting new angiogenic vasculature in a patient, comprising:
  (i) administering to said patient a diagnostic effective amount of a metallopharmaceutical according to embodiment [23]; and
  (ii) generating a MRI image of at least a part of said patient's body;
wherein BM is a vitronectin receptor antagonist, a somatostatin analog, or a growth factor receptor antagonist; and
M is paramagnetic metal ion of atomic number 21–29, 42–44 or 58–70.

[38] Another preferred embodiment of the present invention is a method of detecting new angiogenic vasculature in a patient, comprising:
  (i) administering to said patient a diagnostic effective amount of a metallopharmaceutical according to embodiment [23]; and
  (ii) generating an X-ray or CT image of at least a part of said patient's body;
wherein BM is a vitronectin receptor antagonist, a somatostatin analog, or a growth factor receptor antagonist; and
M is heavy metal ion of atomic number 21–31, 39–49, 50, 56–80, 82, 83, 90.

[39] Another preferred embodiment of the present invention is a method of metal detoxification in a patient comprising administering to a patient in need thereof a detoxifying amount of a compound according to embodiment [1], or a weak chelate complex or salt form thereof, with a pharmaceutically acceptable counterion.

[40] Another preferred embodiment of the present invention is a kit for preparing a metallopharmaceutical composition, comprising the following ingredients:
  (i) a conjugate of embodiment [16];
  (ii) a pharmaceutically acceptable carrier, a formulating agent, or an adjuvant;
  (iii) a solution of a salt of a metal, or chelate of a metal; and
  (iv) instructions for reacting the ingredients present in the kit;
wherein the metal is selected from the group consisting of a metal ion of atomic number 21–31, 39–49, 50, 56–80, 82, 83, or 90.

[41] Another preferred embodiment of the present invention is a kit for forming a radiopharmaceutical complex comprising the following components:
  (i) a conjugate of embodiment [16];
  (ii) optionally a reducing agent; and
  (iii) instructions for reacting the components of said kit with a radionuclide solution.

It is appreciated that certain features of the invention, which are, for clarity, described in the context of separate embodiments, may also be provided in combination in a single embodiment. Conversely, various features of the invention which are for brevity, described in the context of a single embodiment, may also be provided separately or in any subcombination.

DEFINITIONS

The term "direct bond" as used herein, means a chemical bond.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The term "alkyl", as used herein, is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl.

The term "alkaryl", mean an -arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "haloalkyl", as used herein, is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl.

The term "alkoxy", as used herein, represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy.

The term "cycloalkyl" as used herein, means a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" as used herein, means a non-aromatic mono- or multicyclic ring system of about 3 to about 10 carbon atoms, preferably of about 5 to about 10 carbon atoms, and which contains at least one carbon—carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, means an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "fluorobenzyl" as used herein, means a benzyl group wherein the phenyl moiety is substituted with one or more fluorine atoms.

The term "alkenyl", as used herein, is intended to include hydrocarbon chains of either a straight or branched configuration and one or more unsaturated carbon—carbon bonds which may occur in any stable point along the chain, such as ethenyl and propenyl.

The term "alkynyl" as used herein, is intended to include hydrocarbon chains of either a straight or branched configuration and one or more triple carbon—carbon bonds which may occur in any stable point along the chain, such as ethynyl and propynyl.

The term "Halo" or "halogen" as used herein, refers to fluoro, chloro, bromo, and iodo; and "counterion" is used to represent a small, negatively charged species such as chloride, bromide, hydroxide, acetate, and sulfate.

The term "carbocycle" or "carbocyclic residue" as used herein, is intended to mean any stable 3- to 7-membered monocyclic or bicyclic or 7-to 13-membered bicyclic or tricyclic, any of which may be saturated (i.e. a cycloalkyl moiety), partially unsaturated saturated (i.e. a cycloalkenyl moiety), or aromatic (i.e. an aryl moiety). Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0] bicyclononane, [4.4.0]bicyclodecane, [2.2.2]bicyclooctane, fluorenyl, phenyl, naphthyl, indanyl, adamantyl, and tetrahydronaphthyl.

The term "heterocycle" or "heterocyclic system" as used herein, is intended to mean a stable 5-to 7-membered monocyclic or bicyclic or 7-to 10-membered bicyclic heterocyclic ring which is a saturated heterocyclic ring (i.e. a heterocyclyl moiety), a partially unsaturated heterocyclic ring (i.e. a heterocyclenyl moiety), or an unsaturated heterocyclic ring (i.e. a heteroaryl moiety), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The term "aromatic heterocyclic system" or "heteroaryl" as used herein, means an aromatic monocyclic or multicyclic ring system of about 5 to about 14 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The designation of the aza, oxa or thia as a prefix before heteroaryl define that at least a nitrogen, oxygen or sulfur atom is present respectively as a ring atom. It is preferred that the total number of S and O atoms in the aromatic heterocycle is not more than 1. A nitrogen atom of an heteroaryl may be a basic nitrogen atom and may also be optionally oxidized to the corresponding N-oxide. Heteroaryl as used herein includes by way of example and not limitation those described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc. ", 82:5566 (1960). Exemplary heteroaryl and substituted heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl.

The term "heterocyclenyl" as used herein, means a non-aromatic monocyclic or multicyclic hydrocarbon ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur atoms, and which contains at least one carbon—carbon double bond or carbon-nitrogen double bond. It is preferred that the total number of S and O atoms in the heterocyclenyl is not more than 1. Preferred ring sizes of rings of the ring system include about 5 to about 6 ring atoms. The designation of the aza, oxa or thia as a prefix before heterocyclenyl define that at least a nitrogen, oxygen or sulfur atom is present respectively as a ring atom. The nitrogen atom of an heterocyclenyl may be a basic nitrogen atom. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc. ", 82:5566 (1960). Exemplary monocyclic azaheterocyclenyl groups include 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include 3,4-dihydro-2H-pyran, dihydrofuranyl, and fluorodihydrofuranyl. Preferred is dihydrofuranyl. An exemplary multicyclic oxaheterocyclenyl group is 7-oxabicyclo[2.2.1]heptenyl. Preferred monocyclic thiaheterocycleny rings include dihydrothiophenyl and dihydrothiopyranyl; more preferred is dihydrothiophenyl.

The term "heterocyclyl" as used herein, means a non-aromatic saturated monocyclic or multicyclic ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur. It is preferred that the total number of S and O atoms in the aromatic heterocycle is not more than 1. Preferred ring sizes of rings of the ring system include about 5 to about 6 ring atoms. The designation of the aza, oxa or thia as a prefix before heterocyclyl define that at least a nitrogen, oxygen or sulfur atom is present respectively as a ring atom. The nitrogen atom of an heterocyclyl may be a basic nitrogen atom. The nitrogen or sulphur atom of the heterocyclyl may also be optionally oxidized to the corresponding N-oxide, S-oxide or S,S-dioxide. "Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4—(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "peptide" as used herein means a linear compound that consists of two or more amino acids (as defined herein) that are linked by means of a peptide bond. A "peptide" as used in the presently claimed invention is intended to refer to a moiety with a molecular weight of less than 10,000 Daltons, preferable less than 5,000 Daltons, and more preferably less than 2,500 Daltons. The term "peptide" also includes compounds containing both peptide and non-peptide components, such as pseudopeptide or peptidomimetic residues or other non-amino acid components. Such a compound containing both peptide and non-peptide components may also be referred to as a "peptide analog".

The term "pseudopeptide" or "peptidomimetic" as used herein, is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue. A "pseudopeptide residue" means that portion of an pseudopeptide or peptidomimetic that is present in a peptide.

The term "peptide bond" as used herein, means a covalent amide linkage formed by loss of a molecule of water between the carboxyl group of one amino acid and the amino group of a second amino acid.

The term "pseudopeptide bonds" as used herein, includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

The term "non-peptide" as used herein, refers to a compound in comprised of preferably less than three amide bonds in the backbone core compound or preferably less than three amino acids or amino acid mimetics.

The phrase "pharmaceutically acceptable" as used herein, is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" as used herein, refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

A thorough discussion of prodrugs is provided in the following: Design of Prodrugs, H. Bundgaard, ed., Elsevier, 1985; Methods in Enzymology, K. Widder et al, Ed., Academic Press, 42, p. 309–396, 1985; A Textbook of Drug Design and Development, Krogsgaard-Larsen and H. Bundgaard, ed., Chapter 5; "Design and Applications of Prodrugs" p. 113–191, 1991; Advanced Drug Delivery Reviews, H. Bundgard, 8, p. 1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference. "Stable compound" and "stable structure" are meant to indicate a compound that is sufficiently robust to survive isolation to a useful degree of purity from a reaction mixture, and formulation into an efficacious therapeutic agent.

The coordination sphere of the radionuclide includes all the ligands or groups bound to the radionuclide. For a transition metal radionuclide, $M_r$, to be stable it typically has a coordination number (number of donor atoms) comprised of an integer greater than or equal to 4 and less than or equal to 9; that is there are 4 to 9 atoms bound to the metal and it is said to have a complete coordination sphere. The requisite coordination number for a stable radionuclide complex is determined by the identity of the radionuclide, its oxidation state, and the type of donor atoms.

Lyophilization aids useful in the preparation of diagnostic kits useful for the preparation of radiopharmaceuticals include but are not limited to mannitol, lactose, sorbitol, dextran, Ficoll, and polyvinylpyrrolidine (PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits useful for the preparation of said radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^9$) occurs more than one time in any constituent or formula for a compound, its definition at each occurrence is independent of its definition at every other occurrence. Thus, for example, if a group is shown to be substituted with 0–2 $R^9$, then said group may optionally be substituted with up to two $R^9$ groups and $R^9$ at each occurrence is selected independently from the definition of $R^9$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc. . . . ) the compounds of the present invention may be delivered in prodrug form. Thus, the present invention is intended to cover prodrugs of the presently claimed compounds, methods of delivering the same and compositions containing the same.

SYNTHESIS OF NEW MACROCYCLES

Hydroxypyridinones are monobasic and form stable metal complexes with hard trivalent metal ions, such as $Fe^{3+}$, $In^{3+}$ and $Ln^{3+}$. Compared to catechols and hydroxymates, hydroxy-pyridinones have relatively low pKa values (5–9). Hydroxypyridinones also have high selectivity in bonding to trivalent metal ions. As a result, chelators based on hydroxy-pyridinones have been used for Fe detoxification. In the present invention, the hydroxypyridinone moiety is used as a part of a macrocyclic chelant using the hydroxy-oxygen and amine-nitrogen for metal bonding.

Macrocyclic Chelants Containing a Substituted 3-Hydroxy-2(1H)-Pyridinone Group One aspect of this invention involves synthesis of macrocyclic chelants containing a substituted 3-hydroxy-2-(1H)-pyridinone group, and their potential use as BFCs for the radiolabeling of biomolecules or their lanthanide complexes as NMR or X-ray contrast agents. Recently, Taylor and coworkers (Patel, M. K., Fox, R., and Taylor, P. D. *Tetrahedron* 1996, 52, 1835–1840) reported a Mannich reaction of a secondary amine with 3-hydroxy-2-(1H)-pyridinone in the presence of formaldehyde. It was found that the Mannich base obtained from 3-hydroxy-2-(1H)-pyridinone is aminomethylated at C4 (the ortho-position of the hydroxy group) and not at C6 position of the pyridinone ring. The C4 mono-substituted Mannich base is formed even at the room temperature. In the present invention, the same approach (Scheme I) was used to prepare macrocyclic chelants containing 3-hydroxy-2-(1H)-pyridinone groups.

The key step is the preparation of the hydroxypyridinone intermediate. For example, 1-[(ethylox-carbonyl) methyl]-3-hydroxy-2(1H)-pyridinone (HPE) was prepared according to the literature procedure (Streater, M. et al, *J. Med. Chem.* 1990, 33, 1749–1755).

Scheme I

Synthesis of Macrocyclic Chelants Containing Substituted 3-Hydroxy-2-(1H)-Pyridinone Moiety

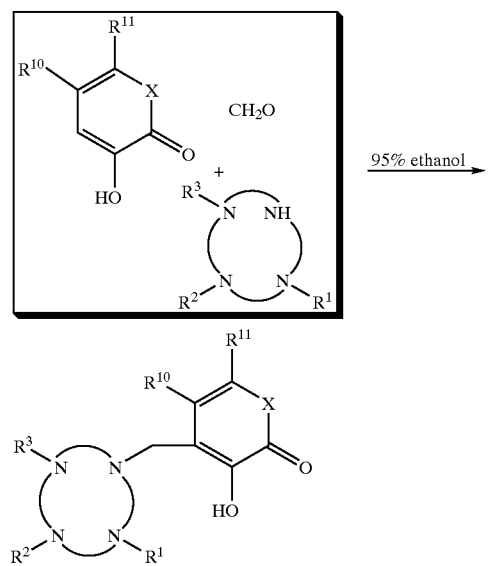

Macrocyclic chelants containing a 3-hydroxy-2-(1H)-pyridinone group are of particular interest as BFCs for the radiolabeling of biomolecules. The biomolecule can be attached to the pyridinone-nitrogen via a direct bond or a linker. It can also be attached to the functional groups ($R^{10}$ and $R^{11}$). The advantage of using these macrocyclic chelants as BFCs is that the attachment of biomolecule does not create any extra chiral center on the chelants themselves. The biomolecules include antibodies, peptides, peptidomimetics, and non-peptide receptor ligands.

Macrocyclic Chelants Containing Substituted 3-Hydroxy-4-(1H)-Pyridinone Groups

Another aspect of this invention involves synthesis of macrocyclic chelants containing a substituted 3-hydroxy-4-(1H)-pyridinone group, and their potential use as BFCs for the radiolabeling of biomolecules or their lanthanide complexes as NMR or X-ray contrast agents. Like 3-hyrdoxy-2-(1H)-pyridinones, 3-hyrdoxy-4-(1H)-pyridinone analogs can also undergo the Mannich reaction with a secondary amine in the presence of formaldehyde. The position of aminomethylation is expected to be at C2 (the ortho-position of the hydroxy group). Scheme II shows the general scheme for the synthesis of macrocyclic chelants containing a substituted 3-hyrdoxy-4-(1H)-pyridinone moiety. Preparation of the substituted 3-hyrdoxy-4-(1H)-pyridinone intermediates can be accomplished by following procedures described in prior literature (Molenda, J. J. et at. *J. Med. Chem.* 1994, 37, 93–98).

Scheme II

Synthesis of Macrocyclic Chelants Containing Substituted 3-Hydroxy-4-(1H)-Pyridinone Moiety

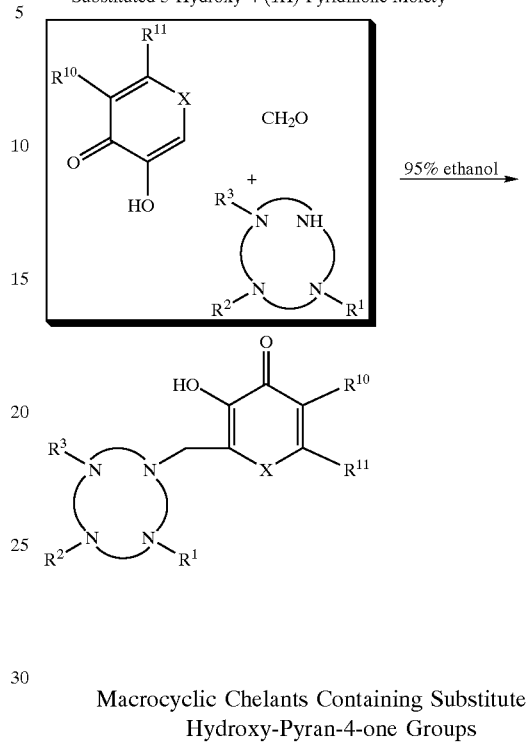

Macrocyclic Chelants Containing Substituted 3-Hydroxy-Pyran-4-one Groups

Another aspect of this invention involves synthesis of macrocyclic chelants containing a substituted 3-hydroxy-pyran-4-one group, and their potential use as BFCs for the radiolabeling of biomolecules or their lanthanide complexes as NMR or X-ray contrast agents. Taylor and coworkers (Fox, R. C. and Taylor, P. D. *Synth. Commun.* 1998, 28, 3983–3989) also reported a Mannich reaction of a peperazine with kojic acid (5-hydroxy-2-hydroxymethyl-pyran-4-one) in the presence of formaldehyde. The reaction was performed at room temperature. Using the same approach, macrocyclic chelants containing a 3-hydroxy-pyran-4-one group can be synthesized by reacting 3-hydroxy-pyran-4-one with the tri-substituted macrocyclic tetraamine in the presence of formaldehyde according to Scheme III.

Scheme III

Synthesis of Macrocyclic Chelants Containing Substituted 3-Hydroxy-Pyran-4-one Moiety

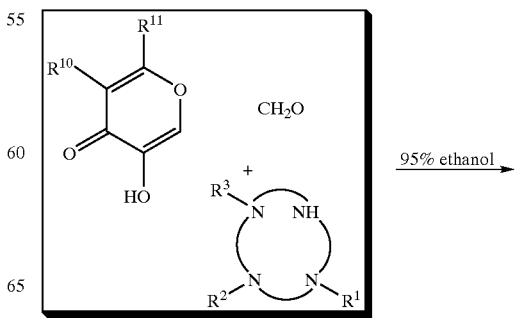

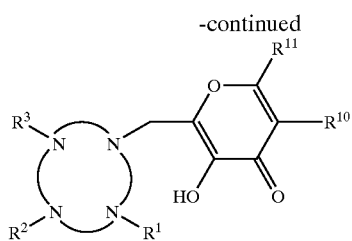

Macrocyclic Chelants Containing Substituted Succinimide or Phthalimide Groups.

Another aspect of this invention involves synthesis of macrocyclic chelants containing a substituted succinimide or phthalimide group, and their potential use as BFCs for the radiolabeling of biomolecules or their lanthanide complexes as NMR or X-ray contrast agents. In these macrocyclic chelants, the succinimide or phthalimide moiety is connected to one of the four amine-nitrogen atoms of the macrocycle via a $C_1-C_3$ alkylene linker in such a way that the carbonyl-O atom of the succinamide or phthalimide group is expected to coordinate the lanthanide metal ions to form 8- or 9-coordinated metal chelates. Due to the presence of DO3A chelating unit, these macrocyclic chelants will form lanthanide metal chelates with high thermodynamic stability and kinetic inertness. Scheme IV shows a general procedure for the synthesis of macrocyclic chelants containing a succinimide or phthalimide group. The tri-substituted tetraamine reacts with a N-(bromoalkyl) succinimide or N-(bromoalkyl)phthalimide in the presence of a base such as potassium carbonate or triethylamine to give the expected product. If these macrocyclic chelants are used as BFCs for the radiolabeling of biomolecules, the biomolecule can be attached to the 5-membered succinimide ring via a direct bond or a linker. It can also be attached to the functional groups ($R^{10}$ and $R^{11}$). The attachment of biomolecule does not create any extra chiral center on the chelants. The biomolecules include antibodies, antibody fragments, peptides, peptidomimetics, and non-peptide receptor ligands.

Scheme IV
Synthesis of Macrocyclic Chelants Containing a Succinimide or Phthalimide group.

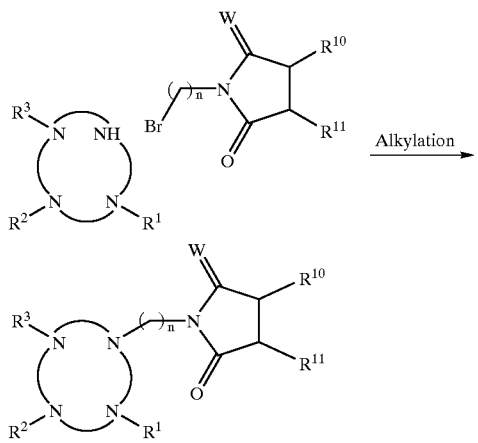

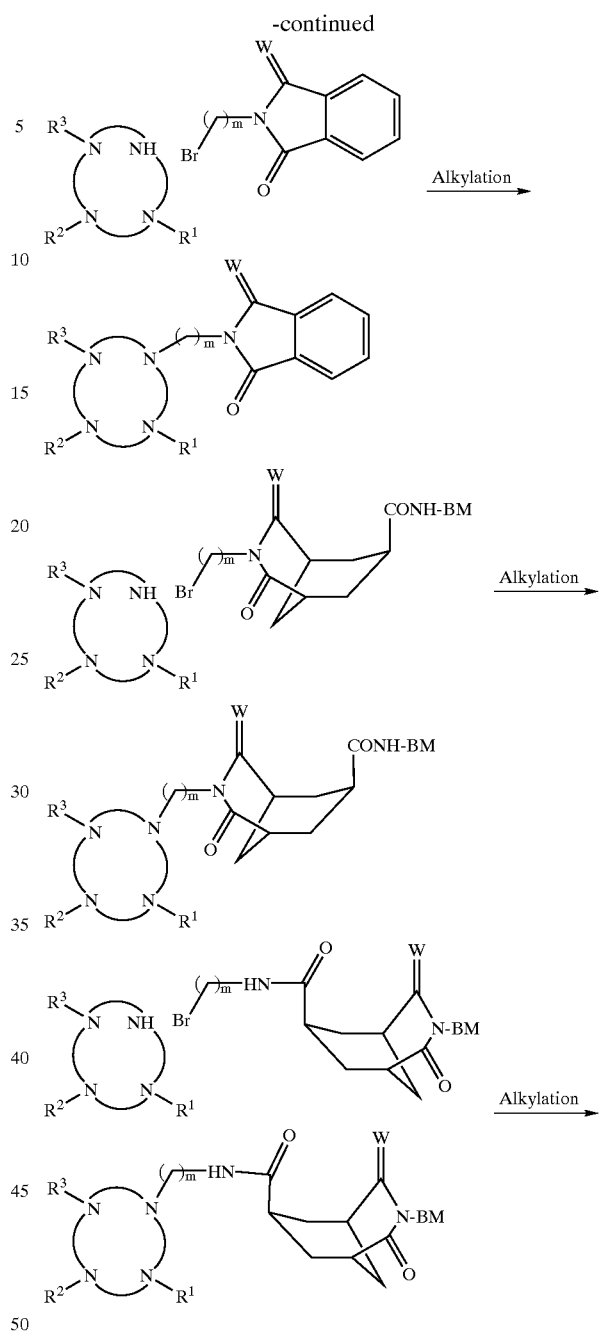

Macrocyclic Chelants Detrivatized from Tris (hydroxy-methyl) phosine

Another aspect of this invention involves synthesis of macrocyclic chelants derivatized from tris(hydroxymethyl) phosphine (THP) and their potential use as BFCs for the radiolabeling of biomolecules or their lanthanide complexes as NMR or X-ray contrast agents. It is known that hydroxymethylphosophines undergo the Mannich reactions with primary and secondary amines (Märkl, V. G., et al. *Tetrhedron Letters*, 1980, 21, 1409–1412). Mannich reactions have been extensively reviewed (Tramotini, M. and Angiolini, L. *Tetrahedron, 1990, 1791–1823;* Tramotini, M. *SYNTHESIS*, 1976, 703–775). Recently, Mannich reactions of hydroxymethylphosphines with amines, amino acids, and peptides (Katti, K. V. et al, *J. Am. Chem. Soc.* 1999, 121, 1658–1664) were reported. In the present invention, the Mannich reaction (Scheme V) of hydroxymethylphosphine with one equivalent of a secondary diamine at pH 3–5 is used to produce new macrocyclic chelants. Oxidation of the phosphine(III) atom of the macrocyclic chelant results in macrocyclic chelants phosphine-oxo group.

Scheme V

Synthesis of Macrocyclic Chelants Derivatized from Tris (hydroxymethyl) phosphine.

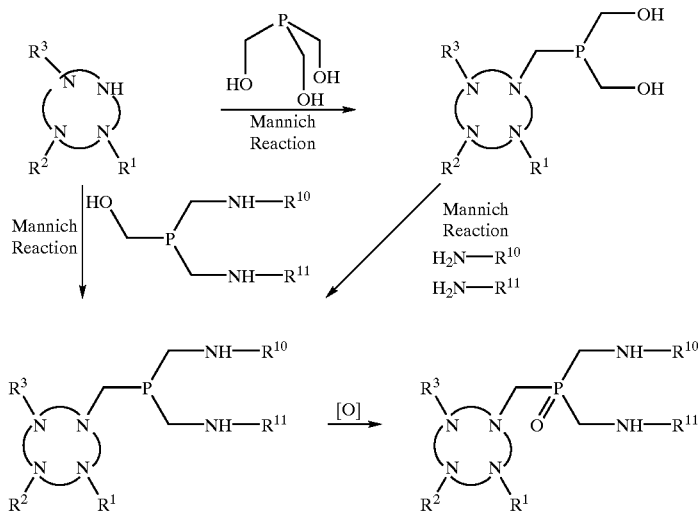

Macrocyclic chelants containing a phosphine-oxo group are of interest because phosphine-oxo oxygen can coordinate the lanthanide metal ions to form 8- or 9-coordinated metal chelates. These macrocyclic chelants are expected to form metal chelates with high thermodynamic stability and kinetic inertness. They can also be used as BFCs for the radiolabeling of biomolecules. The biomolecule can be attached to the functional groups ($R^{10}$ and $R^{11}$). The biomolecules include antibodies, antibody fragments, peptides, peptidomimetics, and non-peptide receptor ligands.

Scheme VI

Synthesis of Macrocyclic Chelants Derivatized from Phosphoric Triesters.

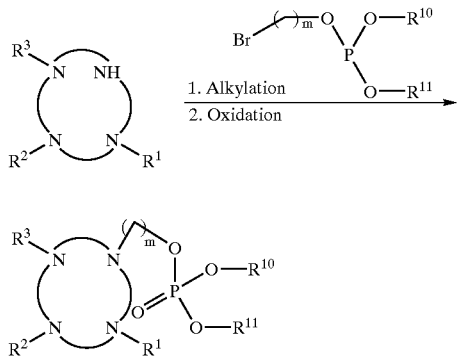

-continued

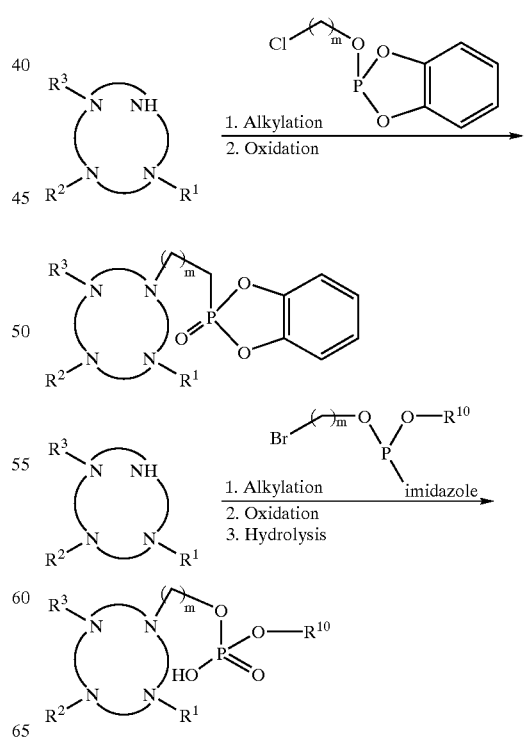

Macrocyclic Chelants Derivatized from Phosphoric Triester

Another aspect of this invention involves synthesis of macrocyclic chelants derivatized from phosphoric triesters, and their potential use as BFCs for the radiolabeling of biomolecules or their lanthanide complexes as NMR or X-ray contrast agents. Synthesis of macrocyclic chelants can be achieved by reacting the tri-substituted macrocyclic tetraamine with bromoalkylphosphite in the presence of a base, such as triethylamine, followed by oxidation of the phosphite to give the corresponding phosphoric triester. The chloro- or bromoalkylphosphite can be obtained from commercial sources or prepared according to procedures described in prior arts (U.S. Pat. No. 5,919,967).

Scheme VII

Synthesis of Macrocyclic Chelants Derivatized from Phosphonic Acid Diesters.

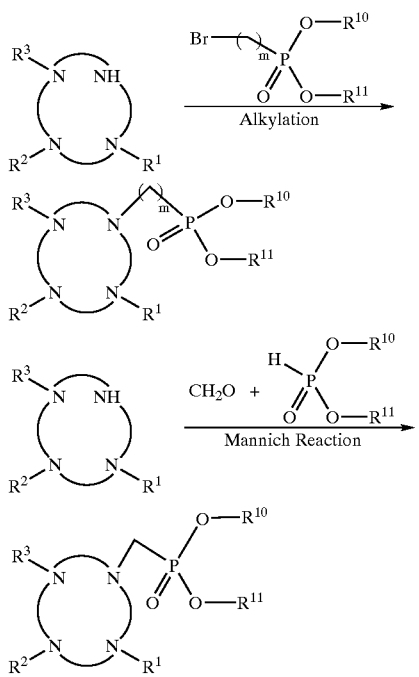

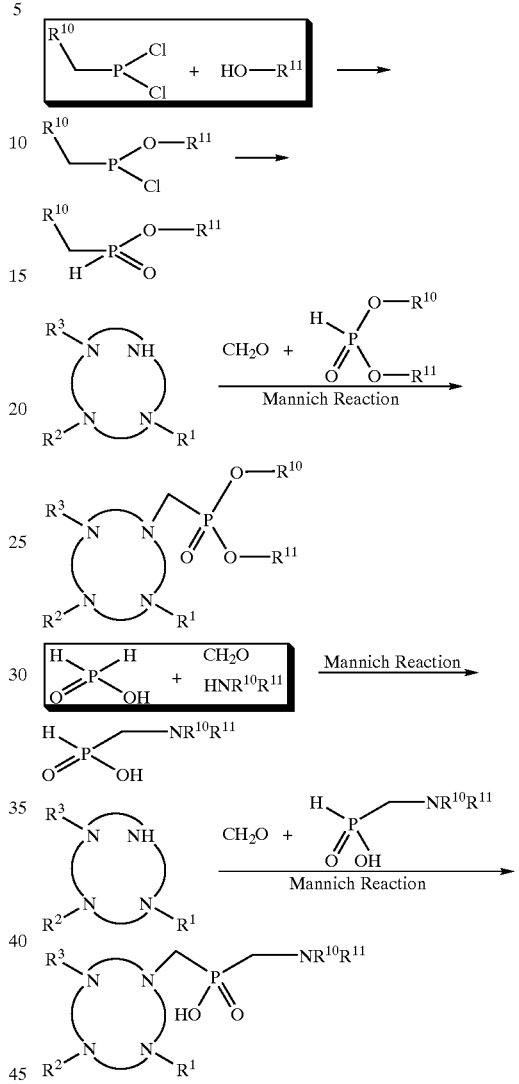

Scheme VIII

Synthesis of Macrcocyclic Chelants Derivatized from Phosphinic Esters.

Macrocyclic Chelants Derivatized from Phosphonic Acid Diester

Another aspect of this invention involves synthesis of macrocyclic chelants derivatized from phosphonic acid diesters, and their potential use as BFCs for the radiolabeling of biomolecules or their lanthanide complexes as NMR or X-ray contrast agents. Synthesis (Scheme VII) of macrocyclic chelants can be achieved by the reaction of the tri-substituted macrocyclic tetraamine with bromoalkylphosphonic acid diester in the presence of a base, such as triethylamine. Some macrocyclic chelants can be prepared by a Mannich reaction (Scheme VII) of the tri-substituted macrocyclic tetraamine with phosphonic acid diester in the presence of formaldehyde. The bromoalkylphosphonic acid diester or phosphonic acid diester can be obtained from commercial sources or prepared according to procedures described in prior arts (examples include Lamande, L, et al *Phosphorus Sulfur and Silicon* 1999, 144, 529–532; Grevy, J.-M., et al *SYNLETT.* 1997, 555–556).

Macrocyclic Chelants Derivatized from Phosphinic Esters

Another aspect of this invention involves synthesis of macrocyclic chelants derivatized from phosphinic esters, and their potential use as BFCs for the radiolabeling of biomolecules or their lanthanide complexes as NMR or X-ray contrast agents. Synthesis (Scheme VIII) of macrocyclic chelants can be achieved by a Mannich reaction of the tri-substituted macrocyclic tetraamine with phosphinic acid ester in the presence of formaldehyde. Some macrocyclic chelant can be prepared by reacting the tri-substituted macrocyclic tetraamine with one equivalent of a semi-Mannich base in the presence of formaldehyde. Phosphinic acid and its esters can be obtained either from commercial sources or prepared according to published procedures.

Macrocyclic chelants containing a phosphinic acid or phosphinic ester are of interest because phosphinyl-oxygen or phosphinate-oxygen can coordinate the lanthanide metal ions to form 8- or 9-coordinated metal chelates with high thermodynamic stability and kinetic inertness. They can also be used as BFCs for the radiolabeling of biomolecules. The biomolecule can be attached to the functional groups ($R^{10}$ and $R^{11}$). The biomolecules include antibodies, antibody fragments, peptides, peptidomimetics, and non-peptide receptor ligands.

The bio-targeted pharmaceuticals of the present invention have the formulae, $(BM)_d—L_n—(C_h—X)$, and $(BM)_d—L_n—(C_h—X^1)_{d'}$, wherein BM represents a peptide, polypeptide, peptidomimetic, or non-peptide that binds to a receptor or enzyme expressed or up-regulated in an organ or disease state, d is 1–10, $L_n$ represents an optional linking group, $C_h$ represents a novel metal chelator of the present invention, d' is 1–100, X represents a radioisotope, and $X^1$ represents a metal ion of atomic number 21–31, 39–49, 50, 56–80, 82, 83 or 90.

The pharmaceuticals of the present invention can be synthesized by several approaches. One approach involves the synthesis of the targeting peptide, polypeptide, peptidomimetic or non-peptide moiety, BM, and direct attachment of one or more moieties, BM, to one or more metal chelators, $C_h$. Another approach involves the attachment of one or more moieties, BM, to the linking group, $L_n$, which is then attached to one or more metal chelators, $C_h$. Another approach, useful in the synthesis of pharmaceuticals wherein d is 1, involves the synthesis of the moiety, BM-$L_n$, together, by incorporating a group bearing $L_n$ into the synthesis of the peptide, polypeptide, peptidomimetic, or non-peptide. The resulting moiety, BM-$L_n$, is then attached to one or more metal chelators, $C_h$. Another approach involves the synthesis of a peptide, polypeptide, peptidomimetic, or non-peptide, BM, bearing a fragment of the linking group, $L_n$, one or more of which are then attached to the remainder of the linking group and then to one or more metal chelators, $C_h$.

The peptides, polypeptides, peptidomimetics and non-peptides, BM, optionally bearing a linking group, $L_n$, or a fragment of the linking group, can be synthesized using standard synthetic methods known to those skilled in the art. Preferred methods include but are not limited to those methods described below.

Generally, peptides, polypeptides, and peptidomimetics are elongated by deprotecting the alpha-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield (J. Am. Chem. Soc. 1963 85, 2149–2154), the disclosure of which is hereby incorporated by reference.

The peptides, polypeptides and peptidomimetics may also be synthesized using automated synthesizing equipment. In addition to the foregoing, procedures for peptide, polypeptide and peptidomimetic synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Synthesis" Springer-Verlag, New York (1984), the disclosures of which are hereby incorporated by reference.

The coupling between two amino acid derivatives, an amino acid and a peptide, polypeptide or peptidomimetic, two peptide, polypeptide or peptidomimetic fragments, or the cyclization of a peptide, polypeptide or peptidomimetic can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids or amino acid mimetics must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Synthesis, Biology, Vol. 3, Academic Press, New York (1981), the disclosure of which is hereby incorporated by reference.

The alpha-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) J. Org. Chem. 45, 1295–1300) chloro or bromomethyl resin, hydroxymethyl resin, and aminomethyl resin. Many of these resins are commercially available with the desired C-terminal amino acid already incorporated.

The alpha-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methyl-ethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkyl-silane such as trimethylsilane; and 7) thiol containing types such as phenylthiocarbonyl and dithiasuccinoyl. The preferred alpha-amino protecting group is either Boc or Fmoc. Many amino acid or amino acid mimetic derivatives suitably protected for peptide synthesis are commercially available.

The alpha-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids or amino acid mimetics bearing side chain functionalities must be protected during the preparation of the peptide using any of the above-identified groups. Those skilled in the art will appreciate that the selection and use of appropriate protecting groups for these side chain functionalities will depend upon the amino acid or amino acid mimetic and presence of other protecting groups in the peptide, polypeptide or peptidomimetic. The selection of such a protecting group is important in that it must not be removed during the deprotection and coupling of the alpha-amino group.

For example, when Boc is chosen for the alpha-amine protection the following protecting groups are acceptable: p-toluenesulfonyl (tosyl) moieties and nitro for arginine; benzyloxycarbonyl, substituted benzyloxycarbonyls, tosyl or trifluoroacetyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the alpha-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation of the peptide, polypeptide or peptidomimetic, or the elongation and cyclization of a cyclic peptide or peptidomimetic is completed all of the protecting groups are removed. For the liquid phase synthesis the protecting groups are removed in whatever manner as dictated by the choice of protecting groups. These procedures are well known to those skilled in the art.

When a solid phase synthesis is used to synthesize a cyclic peptide or peptidomimetic, the peptide or peptidomimetic should be removed from the resin without simultaneously removing protecting groups from functional groups that might interfere with the cyclization process. Thus, if the peptide or peptidomimetic is to be cyclized in solution, the cleavage conditions need to be chosen such that a free α-carboxylate and a free α-amino group are generated without simultaneously removing other protecting groups. Alternatively, the peptide or peptidomimetic may be removed from the resin by hydrazinolysis, and then coupled by the azide method. Another very convenient method involves the synthesis of peptides or peptidomimetics on an oxime resin, followed by intramolecular nucleophilic displacement from the resin, which generates a cyclic peptide or peptidomimetic (Osapay, Profit, and Taylor (1990) *Tetrahedron Letters* 43, 6121–6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0° C. The cleavage of the peptide or peptidomimetic can also be accomplished by other acid reagents such as trifluoromethanesulfonic acid/trifluoroacetic acid mixtures.

Unusual amino acids used in this invention can be synthesized by standard methods familiar to those skilled in the art ("The Peptides: Analysis, Synthesis, Biology, Vol. 5, pp. 342–449, Academic Press, New York (1981)). N-Alkyl amino acids can be prepared using procedures described in previously (Cheung et al., (1977) *Can. J. Chem.* 55, 906; Freidinger et al., (1982) *J. Org. Chem.* 48, 77 (1982)), which are incorporated herein by reference.

Additional synthetic procedures that can be used by one of skill in the art to synthesize the peptides, polypeptides and peptidomimetics targeting moieties are described in U.S. Pat. No. 5,879,657, the contents of which are herein incorporated by reference.

The attachment of linking groups, $L_n$, to the peptides, polypeptides, peptidomimetics and non-peptide, BM; chelators, $C_h$, to the peptides, polypeptides, peptidomimetics, and non-peptides, BM, or to the linking groups, $L_n$; and peptides, polypeptides, peptidomimetics, and non-peptides bearing a fragment of the linking group to the remainder of the linking group, in combination forming the moiety, $(BM)_d$—$L_n$, and then to the moiety $C_h$; can all be performed by standard techniques. These include, but are not limited to, amidation, esterification, alkylation, and the formation of ureas or thioureas. Procedures for performing these attachments can be found in Brinkley, M., *Bioconjugate Chemistry* 1992, 3(1), which is incorporated herein by reference.

The linking group $L_n$ can serve several roles. First it provides a spacing group between the metal chelator, and the one or more of the peptides, polypeptides, peptidomimetics, or non-peptides, BM, so as to minimize the possibility that the moieties $C_h$—X, $C_h$—$X^1$, will interfere with the interaction of the recognition sequences of BM with the target receptors. The necessity of incorporating a linking group in a reagent is dependent on the identity of BM, $C_h$—X, and $C_h$—$X^1$. If $C_h$—X, and $C_h$—$X^1$, cannot be attached to BM without substantially diminishing its affinity for the receptors, then a linking group is used. A linking group also provides a means of independently attaching multiple peptides, polypeptides, peptidomimetics, and non-peptides, BM, to one group that is attached to $C_h$—X, or $C_h$—$X^1$.

The linking group also provides a means of incorporating a pharmacokinetic modifier into the pharmaceuticals of the present invention. The pharmacokinetic modifier serves to direct the biodistribution of the injected pharmaceutical other than by the interaction of the targeting moieties, BM, with the target receptors. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood clearance. The modifiers can also be used to direct the route of elimination of the pharmaceuticals. Preferred pharmacokinetic modifiers are those that result in moderate to fast blood clearance and enhanced renal excretion.

For the diagnosis of thromboembolic disorders or atherosclerosis, BM is selected from the group including the cyclic IIb/IIIa receptor antagonist compounds described in U.S. Pat. No. 5,879,657; the RGD containing peptides described in U.S. Pat. Nos. 4,578,079, 4,792,525, the applications PCT US88/04403, PCT US89/01742, PCT US90/03788, PCT US91/02356 and by Ojima et. al., 204th Meeting of the Amer. Chem. Soc., 1992, Abstract 44; the peptides that are fibrinogen receptor antagonists described in European Patent Applications 90/202015.5, 90/202030.4, 90/202032.2, 90/202032.0, 90/311148.2, 90/311151.6, 90/311537.6, the specific binding peptides and polypeptides described as IIb/IIIa receptor ligands, ligands for the polymerization site of fibrin, laminin derivatives, ligands for fibrinogen, or thrombin ligands in PCT WO 93/23085 (excluding the technetium binding groups); the oligopeptides that correspond to the IIIa protein described in PCT WO90/00178; the hirudin-based peptides described in PCT WO90/03391; the IIb/IIIa receptor ligands described in PCT WO90/15818; the thrombus, platelet binding or atherosclerotic plaque binding peptides described in PCT WO92/13572 (excluding the technetium binding group) or GB 9313965.7; the fibrin binding peptides described in U.S. Pat. Nos. 427,646 and 5,270,030; the hirudin-based peptides described in U.S. Pat. No. 5,279,812; or the fibrin binding proteins described in U.S. Pat. No. 5,217,705; the guanine derivatives that bind to the IIb/IIIa receptor described in U.S. Pat. No. 5,086,069; or the tyrosine derivatives described in European Patent Application 0478328A1, and by Hartman et. al., J. Med. Chem., 1992, 35, 4640; or oxidized low density lipoprotein (LDL).

For the diagnosis of infection, inflammation or transplant rejection, BM is selected from the group including the leukocyte binding peptides described in PCT WO93/17719 (excluding the technetium binding group), PCT WO92/13572 (excluding the technetium binding group) or U.S. Ser. No. 08-140000; the chemotactic peptides described in Eur. Pat. Appl. 90/108734.6 or A. Fischman et. al., Semin. Nuc. Med., 1994, 24, 154; the leukostimulatory agents described in U.S. Pat. No. 5,277,892; or the LTB4 antagonists described in PCT publication no. WO98/15295.

For the diagnosis of cancer, BM is selected from the group of somatostatin analogs described in UK Application 8927255.3 or PCT WO94/00489, the selectin binding peptides described in PCT WO94/05269, the biological-function domains described in PCT WO93/12819, Platelet Factor 4 or the growth factors (PDGF, VEGF, EGF, FGF, TNF MCSF or the interleukins III-8).

BM may also be a compound that binds a receptor that is expressed or upregulated in angiogenic tumor vasculature. For targeting the VEGF receptors, Flk-1/KDR, Flt-1, and neuropilin-1, the targeting moieties are comprised of peptides, polypeptides or peptidomimetics that bind with high affinity to the receptors. For example, peptides comprised of a 23 amino acid portion of the C-terminal domain of VEGF have been synthesized which competitively inhibit binding of VEGF to VEGFR (Soker, et. al., J. Biol. Chem., 1997, 272, 31582–8). Linear peptides of 11 to 23 amino acid residues that bind to the basic FGF receptor (bFGFR) are described by Cosic et. al., Mol. and Cell. Biochem., 1994, 130, 1–9. A preferred linear peptide antagonist of the bFGFR is the 16 amino acid peptide, Met-Trp-Tyr-Arg-Pro-Asp-Leu-Asp-Glu-Arg-Lys-Gln-Gln-Lys-Arg-Glu. Gho et. al. (Cancer Research, 1997, 57, 3733–40) describe the identification of small peptides that bind with high affinity to the angiogenin receptor on the surface of endothelial cells. A preferred peptide is Ala-Gln-Leu-Ala-Gly-Glu-Cys-Arg-Glu-Asn-Val-Cys-Met-Gly-Ile-Glu-Gly-Arg, in which the two Cys residues form an intramolecular disulfide bond. Yayon et. al. (Proc. Natl. Acad. Sci, USA, 1993, 90, 10643–7) describe other linear peptide antagonists of FGFR, identified from a random phage-displayed peptide library. Two linear octapeptides, Ala-Pro-Ser-Gly-His-Tyr-Lys-Gly and Lys-Arg-Thr-Gly-Gln-Tyr-Lys-Leu are preferred for inhibiting binding of bFGF to it receptor.

Targeting moieties for integrins expressed in tumor vasculature include peptides, polypeptides and peptidomimetics that bind to $\alpha v\beta 3$, $\alpha v\beta 5$, $\alpha 5\beta 1$, $\alpha 4\beta 1$, $\alpha 1\beta 1$, and $\alpha 2\beta 2$. Pierschbacher and Rouslahti (J. Biol. Chem., 1987, 262, 17294–8) describe peptides that bind selectively to $\alpha 5\beta 1$ and $\alpha v\beta 3$. U.S. Pat. No. 5,536,814 describe peptides that bind with high affinity to the integrin $\alpha 5\beta 1$. Burgess and Lim (J. Med. Chem., 1996, 39, 4520–6) disclose the synthesis three peptides that bind with high affinity to $\alpha v\beta 3$: cyclo [Arg-Gly-Asp-Arg-Gly-Asp], cyclo[Arg-Gly-Asp-Arg-Gly-D-Asp] and the linear peptide Arg-Gly-Asp-Arg-Gly-Asp. U.S. Pat. Nos. 5,770,565 and 5,766,591 disclose peptides that bind with high affinity to $\alpha v\beta 3$. U.S. Pat. Nos. 5,767, 071 and 5,780,426, disclose cyclic peptides that have an exocyclic Arg amino acid that have high affinity for $\alpha v\beta 3$. Srivatsa et. al., (Cardiovascular Res., 1997, 36, 408–28) describe the cyclic peptide antagonist for $\alpha v\beta 3$, cyclo[Ala-Arg-Gly-Asp-Mamb]. Tran et. al., (Bioorg. Med. Chem. Lett., 1997, 7, 997–1002) disclose the cyclic peptide cyclo [Arg-Gly-Asp-Val-Gly-Ser-BTD-Ser-Gly-Val-Ala] that binds with high affinity to $\alpha v\beta 3$. Arap et. al. (Science, 1998, 279, 377–80) describe cyclic peptides that bind to $\alpha v\beta 3$ and $\alpha v\beta 5$, Cys-Asp-Cys-Arg-Gly-Asp-Cys-Phe-Cys, and cyclo [Cys-Asn-Gly-Asp-Cys]. Corbett et. al. (Biorg. Med. Chem. Lett., 1997, 7, 1371–6) describe a series of $\alpha v\beta 3$ selective peptidomimetics. And Haubner et. al., (Angew. Chem. Int. Ed. Engl., 1997, 36, 1374–89) disclose peptides and peptidomimetic $\alpha v\beta 3$ antagonists obtained from peptide libraries.

Alternative targeting moieties for tumor vasculature include compounds that interact with receptor tyrosine kinases. Receptor tyrosine kinases (TKs) are membrane proteins, which play a key role in the transduction of mitogenic signals across the cell to the nucleus (Rewcastle, G. W. et al J. Med. Chem. 1995, 38, 3482–3487; Thompson, A. M. et al J. Med. Chem. 1997, 40, 3915–3925). Of the many TKs that have been identified and characterized, those of the epidermal growth factor receptor (EGFR) family are particularly important, and have been implicated in a variety of ectopic cell proliferative processes. The over-expression of human EGF receptor is greatly amplified in several human tumors (Fry, D. W. Exp. Opin. Invest. Drugs 1994, 3, 577–595; Jardines, L. et al Pathobiology 1993, 61, 268–282), accompanied by an overphosphorylation of their protein targets. This increased phosphorylation of substrate tyrosine residues by oncogenic TK proteins is an essential step in the neoplastic transformation. Consequently, there has been great interest in developing inhibitors of TKs (TKIs) as anticancer drugs (Burke, T. R. Jr. Drugs Future 1992 17, 119–131; Chang, C. J. and Geahlen, R. J. Nat. Prod. 1992, 55, 1529–1560). The over-expression of EGF receptors in tumor cells also provides the foundation for the development of diagnostic and therapeutic radiopharmaceuticals by attaching a chelator and a radionuclide onto the TK receptor ligand (tyrosine kinase inhibitor).

BM may also represent proteins, antibodies, antibody fragments, peptides, polypeptides, or peptidomimetics that bind to receptors or binding sites on other tissues, organs, enzymes or fluids. Examples include the β-amyloid proteins that have been demonstrated to accumulate in patients with Alzheimer's disease, atrial naturetic factor derived peptides that bind to myocardial and renal receptors, antimyosin antibodies that bind to areas of infarcted tissues, or nitroimidazole derivatives that localize in hypoxic areas in vivo.

A conjugate of the invention may be used for the detoxification of heavy metals by using a corresponding salt form of the conjugate with a pharmaceutically acceptable counterion, e.g. sodium, calcium, ammonium, or zinc.

Other features of the invention will become apparent in the course of the following descriptions of exemplary embodiments which are given for illustration of the invention and are not intended to be limiting thereof.

EXAMPLES

3-Hydroxy-2(1H)-pyridinone, paraformaldehyde were purchased from Aldrich. 1-[(Ethyloxcarbonyl)methyl]-3-hydroxy-2(1H)-pyridinone (HPE) was prepared according to the literature procedure (*J. Med. Chem.* 1990, 33, 1749–1755).

Instruments $^1$H NMR spectra were recorded on a 600 MHz Bruker spectrometer. The $^1$H NMR data were reported as δ (ppm) relative to TMS. Electrospray MS analyses were performed using a VG Quattro mass spectrometer. LC-MS spectra were collected using a HP1100 LC/MSD system with API-electrospray interface. The high-performance liquid HPLC methods used a Hewlett Packard Model 1090 instrument with radiometric detector using a sodium iodide probe.

Example I

Synthesis of 1,4,7,10-tetraazacyclododecane-1-{1-[(Ethyloxcarbonyl) methyl]-3-hydroxy-2(1H)-pyridinone-4-methyl}-4,7,10-triacetic acid (DO3A-HPE).

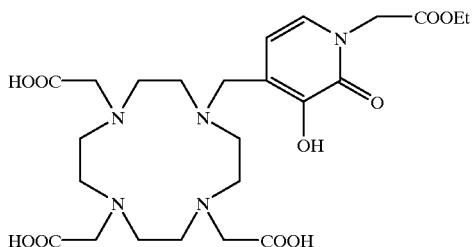

To a solution of tributyl ester of DO3A (160 mg, 0.312 mmol) in 95% ethanol (45 mL) was added HPE (68 mg, 0.342 mmol) and paraformaldehyde (20 mg, 0.67 mmol). The resulting mixture was stirred at room temperature for 48 hours. Solvents were removed under reduced pressure to give a brownish gummy liquid, which was re-dissolved in dichloromethane (15 mL) and anhydrous TFA (10 mL). The mixture was stirred at room temperature overnight. Solvents were removed under reduced pressure. The residue was dissolved in methanol (1.5–2.0 mL). Upon addition of acetone (10 mL) and diethyl ether (50 mL), an off-white solid was formed. The solid was separated by filtration, washed with diethyl ether, and dried in air. The crude product was purified by HPLC with the following method:

| | |
|---|---|
| Solvent A: | 0.1% TFA |
| Solvent B: | acetonitrile |
| Column: | Zorbax C18 reversed phase semi-prep column |
| Flow rate: | 3 mL/min |
| Temperature: | ambient |
| Gradient: | Solvent B from 5% to 10% over 20 min. |

The fractions at retension times of 10–12.5 min were collected. The collected fractions were combined. Sovents were removed on a rotary evaporator. The residue was dissolved in 1 mL of water, and was re-purified using a slightly different gradient:

Solvent B was isocratic (5% B) for the first 5 minutes, and then went from 5% to 20% over the next 15 min. The fractions at 13–17 min were collected. The collected fractions were combined, and lyophilized to give a white powder. The yield was 15 mg. Electrospray MS: M/z=556.3 for $[C_{24}H_{37}N_5O_{10}]^+$, 278.6 for $[C_{24}H_{38}N_5O_{10}]^{2+}$. $^1$H NMR (600 MHz, in $D_2O$, chemical shift in ppm relatinve to TMS): 1.52 (t, 4H, $CH_3$); 3.51–3.59 (m, 16H, $CH_2$ cyclen); 3.86 (m, 4H, $CH_2$ acetate); 4.05 (s, 2H, $CH_2$ acetate); 4.50 (m, 4H, $CH_2$/ethyl and $CH_2$/methylenepyridinone); 5.06 (s, 2H, $NCH_2$, acetate); 6.82 (d, 1H, pyridinone); and 7.41 (d, 1H, pyridinone).

Example II

Synthesis of $^{177}$Lu Complex of DO3A-HPE.

To a shielded 5 mL vial was added 0.5 mL of DO3A-HPE solution (100 μg/mL in 0.5 M ammonium acetate buffer, pH=7.0), followed by 50 μL of sodium gentisate solution (10 mg/mL in 0.5 M ammonium acetate buffer, pH=7.0), and 10 □L of $^{177}LuCl_3$ solution (100 mCi/mL in 0.05 N HCl). The total volume was 560 μL and the pH of the reaction mixture was ~6.5. The mixture was heated at 100° C. for 30 min, and then was analyzed by HPLC with the following method:

| | |
|---|---|
| Solvent A: | 25 mM phosphate buffer, pH = 6.0 |
| Solvent B: | Acetonitrile |
| Column: | Zorbax C18 reversed phase analytical column |
| Flow rate: | 1 mL/min |
| Gradient: | Solvent B from 5% to 10% over 20 min. min. |

The retention time for the complex $^{177}$Lu-DO3A-HPE was 14.5 min, and the radiolabeling yield was ~80%.

Example III

Synthesis of 1,4,7,10-tetraazacyclododecane-1-[N-(phthalimide) ethyl]-4,7,10-triacetic Acid (DO3A-EP).

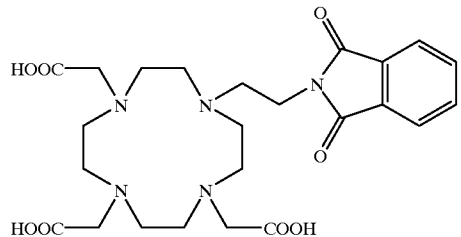

To a solution of tributyl ester of DO3A (160 mg, 0.312 mmole) in anhydrous acetonitrile (50 mL) were added N(2-bromoethyl)phthalimide (68 mg, 0.342 mmole) and triethylamine (20 mg, 0.67 mmole). The resulting mixture was stirred at room temperature for 48 hours. Solvents were removed under the reduced pressure. The residue was extracted with dichloromethane (2×50 mL), washed with water (2×30 mL), dried over anhydrous sodium sulfate. After removal of solvent, the residue was dissolved in a mixture of dichloromethane (15 mL) and anhydrous TFA (15 mL). The mixture was stirred at room temperature overnight. Solvents were removed under reduced pressure. To the residue was added water (3–5 mL) and the resulting mixture was filtered. The filtrate was concentrate to ~2 mL, and the crude product was purified by HPLC with the following method:

| | |
|---|---|
| Solvent A: | 0.1% TFA |
| Solvent B: | acetonitrile |
| Column: | Zorbax C18 reversed phase semi-prep column |
| Flow rate: | 3 mL/min |
| Gradient: | Solvent B from 5% to 20% over 20 min. |

The fractions at retension times of 10–12.5 min were collected. The collected fractions were combined. Solvents were removed on a rotary evaporator. The residue was dissolved in 1 mL of water, and was re-purified using a slightly different gradient: Solvent B was isocratic (5%) for the first 5 minutes, and then went from 5% to 20% over the next 15 min. The fractions at 13–17 min were collected. The collected fractions were combined, and lyophilized to give a white powder. The yield was 15 mg. LC-MS: M/z=520.5 for $[C_{24}H_{34}N_5O_8]^+$, 261.2 for $[C_{24}H_{35}N_5O_8]^{2+}$.

Example IV

Synthesis of $^{111}$In Complex of DO3A-EP.

To a clean 5 mL vial containing 0.6 mL of DO3A-EP solution (200 μg/mL in 0.5 M NH$_4$OAc, pH=7.5) was added 50 μL of $^{111}$InCl$_3$ solution (~0.5 mCi) in 0.05 N HCl. The reaction mixture was heated at 50° C. for 15 min. After cooling to room temperature, the resulting solution was analyzed by an ITLC method using Gelman Sciences silicon gel paper strip, and a 50:50 mixture of saline and acetone as mobile phase. Using this method, $^{111}$InCl$_3$ and [$^{111}$In] acetate remain at the origin while the radiolabeled DO3A-EP mirates to the solvent front. The yield was 85%.

Example V

Synthesis of $^{177}$Lu Complex Of DO3A-EP.

To a clean 5 mL vial containing 0.6 mL of DO3A-EP solution (200 μg/mL in 0.5 M NH$_4$OAc, pH=7.5) was added 5 μL of $^{177}$LuCl$_3$ solution (~4 mCi) in 0.05 N HCl. The reaction mixture was heated at 50° C. for 15 min. After cooling to room temperature, the resulting solution was analyzed by an HPLC method. The retention time was 19 min and the radiolabeling yield was 85%.

| HP-1100 HPLC System | | | | | | | |
|---|---|---|---|---|---|---|---|
| Detector: | IN-US β-Detector | | | | | | |
| Column: | Zorbax C$_{18}$ reverse phase column (25 cm × 4.6 mm) | | | | | | |
| Flow Rate: | 1.0 mL/min | | | | | | |
| Solvent A: | 25 mM ammonium acetate buffer (pH 6.8) | | | | | | |
| Solvent B: | 100% CH$_3$CN | | | | | | |
| Gradient: | Time (min) | 0 | 18 | 19 | 25 | 26 | 32 |
| | % B | 0 | 20 | 60 | 60 | 0 | 0 |
| | % A | 100 | 80 | 40 | 40 | 100 | 100 |

Example IV

Synthesis of $^{90}$Y Complex of DO3A-EP.

To a clean 5 mL vial containing 0.6 mL of DO3A-EP solution (200 μg/mL in 0.5 M NH$_4$OAc, pH=7.5) was added 5 μL of $^{90}$YCl$_3$ solution (~3 mCi) in 0.05 N HCl. The reaction mixture was heated at 50° C. for 15 min. After cooling to room temperature, the resulting solution was analyzed by an HPLC method. The retention time was 19.2 min and the radiolabeling yield was 83%.

| HP-1100 HPLC System | | | | | | | |
|---|---|---|---|---|---|---|---|
| Detector: | IN-US β-Detector | | | | | | |
| Column: | Zorbax C$_{18}$ reverse phase column (25 cm × 4.6 mm) | | | | | | |
| Flow Rate: | 1.0 mL/min | | | | | | |
| Solvent A: | 25 mN ammonium acetate buffer (pH 6.8) | | | | | | |
| Solvent B: | 100% CH$_3$CN | | | | | | |
| Gradient: | Time (min) | 0 | 18 | 19 | 25 | 26 | 32 |
| | % B | 0 | 20 | 60 | 60 | 0 | 0 |
| | % A | 100 | 80 | 40 | 40 | 100 | 100 |

Utility

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

The magnetic resonance imaging contrast agents of the present invention may be used in a similar manner as other MRI agents as described in U.S. Pat. Nos. 5,155,215; 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging from 0.01 to 1.0 mmoles per kg body weight.

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

The pharmaceuticals of the present invention are useful for imaging hypoxia, apoptosis, cardiac ischemia, thrombosis, infection, inflammation, cancer, restenosis, atherosclerosis, diabetic retinopathy, macular degeneration, wound healing, and reperfusion injury, in a patient. The imaging radiopharmaceuticals of the present invention comprised of a gamma ray or positron emitting isotope. The radiopharmaceuticals of the present invention comprised of a beta, alpha or Auger electron emitting isotope are useful for treatment of pathological processes including cancer, rstenosis, diabetic retinopathy, and macular degeneration, by delivering a cytotoxic dose of radiation to the locus of expression of the receptor or enzyme with which the BM interacts (targets). The treatment of cancer is affected by the systemic administration of the radiopharmaceuticals resulting in a cytotoxic radiation dose to tumors.

The compounds of the present invention comprised of one or more paramagnetic metal ions selected from gadolinium, dysprosium, iron, and manganese, are useful as contrast agents for magnetic resonance imaging (MRI) of hypoxia, apoptosis, cardiac ischemia, thrombosis, infection, inflammation, cancer, restenosis, atherosclerosis, diabetic retinopathy, macular degeneration, wound healing, and reperfusion injury.

The compounds of the present invention comprised of one or more heavy atoms with atomic number of 20 or greater are useful as X-ray contrast agents for X-ray imaging of hypoxia, apoptosis, cardiac ischemia, thrombosis, infection, inflammation, cancer, restenosis, atherosclerosis, diabetic retinopathy, macular degeneration, wound healing, and reperfusion injury.

Biochemical assays and in vivo models for testing the pharmaceuticals of the present invention are described in U.S. Pat. No. 5,879,657, PCT Application WO 98/15295, and PCT Application WO 99/51628.

Obviously, numerous modifications and variations of the present invention are possible in light of the above teachings. It is therefore to be understood that within the scope of the appended claims, the invention may be practiced otherwise that as specifically described herein.

All publications, patents, and patent documents are incorporated by reference herein, in their entirety, as though individually incorporated by reference.

What is claimed is:

1. A compound of formula:

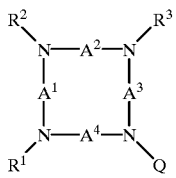

or pharmaceutically acceptable salts thereof, wherein:

$R^1$, $R^2$, and $R^3$ are independently selected from: $C_1$–$C_{10}$ alkyl substituted with 1–5 $R^4$, $C_1$–$C_{10}$ fluoroalkyl substituted with 1–5 R4, $C_2$–$C_{10}$ alkenyl substituted with 1–5 $R^4$, $C_2$–$C_{10}$ fluoroalkenyl substituted with 1–5 $R^4$, and aryl substituted with 1–5 $R^4$, fluoroaryl substituted with 1–5 $R^4$;

$R^4$ is independently selected at each occurrence from: $C(=O)R^5$, $S(O)_2OR^5$, $C(=O)OR^5$, $C(=O)NR^6R^7$, $PO(OR^6)(OR^7)$;

$R^5$, $R^6$ and $R^7$ are independently selected from: H, $C_1$–$C_{10}$ alkyl substituted with 0–5 $R^8$, $C_2$–$C_{10}$ alkenyl substituted with 0–5 $R^8$, $C_3$–$C_{10}$ cycloalkyl substituted with 0–5 $R^8$, $C_1$–$C_{10}$ fluoroalkyl substituted with 0–5 $R^8$, $C_2$–$C_{10}$ fluoroalkenyl substituted with 0–5 $R^8$, aryl substituted with 0–5 $R^8$, and fluoroaryl substituted with 0–3 $R^8$, said $C_1$–$C_{10}$ alkyl and $C_2$–$C_{10}$ alkenyl groups optionally interrupted with —O—, —S—, —NH—, —S(O)—, —S(O)$_2$—, —P(O)(OR$^9$)O—, —P(O)(NHR$^9$)O—, —C(O)NH—, —NHC(O)—, —NHC(O)NH—, or —NHC(S)NH—;

or alternatively, $R^6$ and $R^7$ may be taken together, with the atoms through which they are attached, to form a $C_3$–$C_{10}$ cycloalkyl substituted with 0–5 $R^8$, $C_3$–$C_{10}$ cycloalkenyl substituted with 0–5 $R^8$, aryl substituted with 0–5 $R^8$, or fluoroaryl substituted with 0–5 $R^8$; said $C_3$–$C_{10}$ alkyl and $C_3$–$C_{10}$ cycloalkenyl groups optionally interrupted with —O—, —S—, —NR$^9$—, —S(O)—, —S(O)$_2$—, —P(O)(OR$^9$)—, —P(O)(OR$^9$)O—, —P(O)(NHR$^9$)—, —P(O)(NHR$^9$)O—, —C(O)NH—, —NHC(O)—, —NHC(O)NH—, or —NHC(S)NH—;

$R^8$ is independently selected at each occurrence from: H, —OH, —NHR$^9$, —C(=O)R$^9$, —OC(=O)R$^9$, —OC(=O)OR$^9$, —C(=O)OR$^9$, —C(=O)N(R$^9$)$_2$, —PO(OR$^9$)$_2$, —SR$^9$, —SOR$^9$, —SO$_2$R$^9$, —NHC(=O)R$^9$, —NHC(=O)NHR$^9$, —CH$_2$OR$^9$, and —NHC(=S)NHR$^9$;

$R^9$ is independently selected at each occurrence from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, and fluorophenyl;

$A^1$, $A^2$, $A^3$, and $A^4$ are independently —$(CR^5R^5)_n$—, wherein n is 2 or 3;

Q is a functional group selected from:

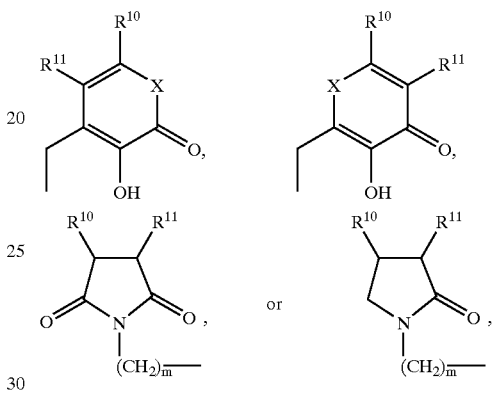

wherein $R^{10}$ and $R^{11}$ are independently selected at each occurrence from: H, $C_1$–$C_{10}$ alkyl substituted with 0–5 $R^{12}$, $C_3$–$C_{10}$ cycloalkyl substituted with 0–5 $R^{12}$, $C_1$–$C_{10}$ fluoroalkyl substituted with 0–5 $R^{12}$, $C_2$–$C_{10}$ alkenyl substituted with 0–5 $R^{12}$, $C_3$–$C_{10}$ cycloalkyl substituted with 0–5 $R^{12}$, $C_2$–$C_{10}$ fluoroalkenyl substituted with 0–5 $R^{12}$, and aryl substituted with 0–5 $R^{12}$, or, alternatively, $R^{10}$ and $R^{11}$ may be taken together, with the atoms through which they are attached, to form a cyclic ring system, said ring system selected from: $C_3$–$C_{10}$ cycloalkyl substituted with 0–5 $R^{12}$, and aryl substituted with 0–3 $R^{12}$;

m is 1–3;

$R^{12}$ is independently selected at each occurrence from the group: $COR^{13}$, $C(=O)OR^{13}$, $C(=O)N(R^{13})_2$, $PO(OR^{13})_2$, $OR^{13}$, and $SO_2OR^{13}$;

$R^{13}$ is independently selected at each occurrence from the group: H, and $C_1$–$C_6$ alkyl;

X is selected from O or NR$^5$; and $Z^1$, $Z^2$, and $Z^3$ are independently selected from: O, NH, CH$_2$NH, and a direct bond.

2. A compound of claim 1, wherein:

$R^1$, $R^2$, and $R^3$ are independently selected from: $C_1$–$C_3$ alkyl substituted with 1–2 $R^4$, $C_1$–$C_3$ fluoroalkyl substituted with 1–2 $R^4$, aryl substituted with 1–2 $R^4$, and fluoroaryl substituted with 1–2 $R^4$;

$R^5$, $R^6$ and $R^7$ are independently selected from: H, $C_1$–$C_3$ alkyl substituted with 0–2 $R^8$, $C_3$–$C_6$ cycloalkyl substituted with 0–2 $R^8$, $C_1$–$C_3$ fluoroalkyl substituted with 0–2 $R^8$, and aryl substituted with 0–2 $R^8$;

or alternatively, $R^6$ and $R^7$ may be taken together, with the atoms through which they are attached, to form a $C_3$–$C_6$ cycloalkyl substituted with 0–2 $R^8$, $C_3$–$C_6$ cycloalkenyl substituted with 0–2 $R^8$, or an aryl substituted with 0–2 $R^8$;

$R^9$ is independently selected at each occurrence from: H, $C_1$–$C_3$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, and fluorophenyl;

$A^1$, $A^2$, $A^3$, and $A^4$ are —$(CR^5R^5)_2$—;

$R^{10}$ and $R^{11}$ are independently selected at each occurrence from: H, $C_1$–$C_3$ alkyl substituted with 0–2 $R^{12}$, $C_3$–$C_6$ cycloalkyl substituted with 0–2 $R^{12}$, $C_1$–$C_3$ fluoroalkyl substituted with 0–2 $R^{12}$, $C_2$–$C_3$ alkenyl substituted with 0–2 $R^{12}$, $C_3$–$C_6$ cycloalkenyl substituted with 0–2 $R^{12}$, $C_2$–$C_3$ fluoroalkenyl substituted with 0–2 $R^{12}$, and aryl substituted with 0–2 $R^{12}$, or, alternatively, $R^{10}$ and $R^{11}$ may be taken together, with the atoms through which they are attached, to form a $C_3$–$C_{10}$ cycloalkyl group substituted with 0–2 $R^{12}$, or aryl group sustituted with 0–2 $R^{12}$;

$R^{13}$ is H or $C_1$–$C_3$ alkyl; and $Z^1$, $Z^2$, and $Z^3$ are independently selected from: O, NH, and a direct bond.

3. A compound of claim 1, wherein:

$R^1$, $R^2$ and $R^3$ are —$CH_2R^4$;

$R^4$ is independently elected at each occurrence from: COOH, $PO_3H_2$, $SO_3H$, and C(=O) $NR^6R^7$;

$A^1$, $A^2$, and $A^3$ are —$(CH_2)_2$—; and

Q is a functional group of the formula:

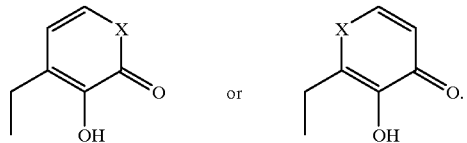

4. A compound of claim 1, wherein:

$R^1$, $R^2$, and $R^3$ are $CH_2R^4$;

$R^4$ is independently elected at each occurrence from: COOH, $PO_3H_2$, $SO_3H$, and C(=O)$NR^6R^7$;

$A^1$, $A^2$, $A^3$ and $A^4$ are —$(CH_2)_2$—; and

Q is a functional group of the formula:

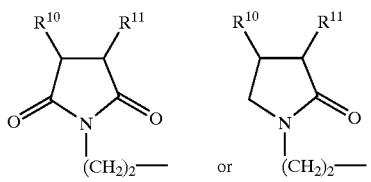

wherein $R^{10}$ and $R^{11}$ are taken together to form a phenyl group substituted with 0–2 $R^{12}$.

5. A compound of claim 1, wherein:

$R^1$, $R^2$ and $R^3$ are —$CH_2R^4$;

$R^4$ is independently elected at each occurrence from: COOH, $PO_3H_2$, $SO_3H$, and C(=O)$NR^6R^7$;

$A^1$, $A^2$, $A^3$, and $A^4$ are —$(CH_2)_2$—; and

Q is a functional group of the formula:

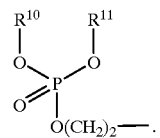

6. A compound of claim 1 of the formula:

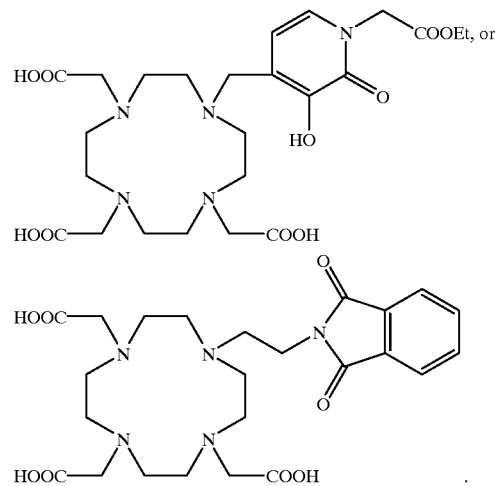

7. A metal chelate complex comprising a compound according to claim 1 complexed to a metal ion of atomic number 21–31, 39–49, 50, 56–80, 82, 83, 90, or alternatively, the compound is complexed to a radionuclide selected from: $^{64}Cu$, $^{62}Cu$, $^{60}Cu$, $^{67}Cu$, $^{67}Ga$, $^{68}Ga$, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$, and $^{188}Re$.

8. A metal chelate complex according to claim 7 of the formula:

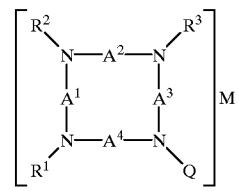

or pharmaceutically acceptable salts thereof,
wherein:

M is X or $X^1$;

X is a radionuclide selected from: $^{64}Cu$, $^{62}Cu$, $^{60}Cu$, $^{67}Cu$, $^{67}Ga$, $^{68}Ga$, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$, and $^{188}Re$;

$X^1$ is a metal ion of atomic number 21–31, 39–49, 50, 56–80, 82, 83, 90;
wherein:

$R^1$, $R^2$, and $R^3$ are independently selected from: $C_1$–$C_{10}$ alkyl substituted with 1–5 $R^4$, $C_1$–$C_{10}$ fluoroalkyl substituted with 1–5 $R^4$, $C_2$–$C_{10}$ alkenyl substituted with 1–5 $R^4$, $C_2$–$C_{10}$ fluoroalkenyl substituted with 1–5 $R^4$, and aryl substituted with 1–5 $R^4$, fluoroaryl substituted with 1–5 $R^4$;

$R^4$ is independently selected at each occurrence from: —C(=O)$R^5$, —S(O)$_2OR^5$, —C(=O)$OR^5$, —C(=O)$NR^6R^7$, —PO($OR^6$)($OR^7$);

$R^5$, $R^6$ and $R^7$ are independently selected from: H, $C_1$–$C_{10}$ alkyl substituted with 0–5 $R^8$, $C_2$–$C_{10}$ alkenyl substituted with 0–5 $R^8$, $C_3$–$C_{10}$ cycloalkyl substituted with 0–5 $R^8$, $C_1$–$C_{10}$ fluoroalkyl substituted with 0–5 $R^8$, $C_2$–$C_{10}$ fluoroalkenyl substituted with 0–5 $R^8$, aryl substituted with 0–5 $R^8$, and fluoroaryl substituted with 0–3 $R^8$, said $C_1$–$C_{10}$ alkyl and $C_2$–$C_{10}$ alkenyl groups optionally interrupted with —O—, —S—, —NH—, —S(O)—, —S(O)$_2$—, —P(O)(OR$^9$)O—, —P(O)(NHR$^9$)O—, —C(O)NH—, —NHC(O)—, —NHC(O)NH—, —NHC(S)NH—;

or alternatively, $R^6$ and $R^7$ may be taken together, with the atoms through which they are attached, to form a $C_3$–$C_{10}$ cycloalkyl substituted with 0–5 $R^8$, $C_3$–$C_{10}$ cycloalkenyl substituted with 0–5 $R^8$, aryl substituted with 0–5 $R^8$, or fluoroaryl substituted with 0–5 $R^8$; said $C_3$–$C_{10}$ alkyl and $C_3$–$C_{10}$ cycloalkenyl groups optionally interrupted with —O—, —S—, —NR$^9$—, —S(O)—, —S(O)$_2$—, —P(O)(OR$^9$)—, —P(O)(OR$^9$)O—, —P(O)(NHR$^9$)—, —P(O)(NHR$^9$)O—, —C(O)NH—, —NHC(O)—, —NHC(O)NH—, or —NHC(S)NH—;

$R^8$ is independently selected at each occurrence from: H, OH, NHR$^9$, C(=O)R$^9$, OC(=O)R$^9$, OC(=O)OR$^9$, C(=O)OR$^9$, C(=O)N(R$^9$)$_2$, PO(OR$^9$)$_2$, SR$^9$, SOR$^9$, SO$_2$R$^9$, NHC(=O)R$^9$, NHC(=O)NHR$^9$, CH$_2$OR$^9$, and NHC(=S)NHR$^9$;

$R^9$ is independently selected at each occurrence from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, and fluorophenyl;

$A^1$, $A^2$, $A^3$, and $A^4$ are independently —(CR$^5$R$^5$)$_n$—, wherein n is 2 or 3;

Q is a functional group selected from:

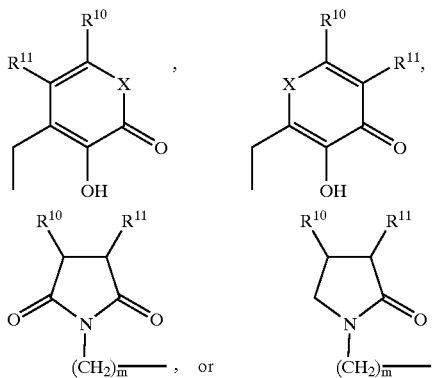

wherein $R^{10}$ and $R^{11}$ are independently selected at each occurrence from: H, $C_1$–$C_{10}$ alkyl substituted with 0–5 $R^{12}$, $C_3$–$C_{10}$ cycloalkyl substituted with 0–5 $R^{12}$, $C_1$–$C_{10}$ fluoroalkyl substituted with 0–5 $R^{12}$, $C_2$–$C_{10}$ alkenyl substituted with 0–5 $R^{12}$, $C_3$–$C_{10}$ cycloalkenyl substituted with 0–5 $R^{12}$, $C_2$–$C_{10}$ fluoroalkenyl substituted with 0–5 $R^{12}$, and aryl substituted with 0–5 $R^{12}$, or, alternatively, $R^{10}$ and $R^{11}$ may be taken together, with the atoms through which they are attached, to form a cyclic ring system, said ring system selected from: $C_3$–$C_{10}$ cycloalkyl substituted with 0–5 $R^{12}$ and aryl substituted with 0–3 $R^{12}$;

m is 1–3;

$R^{12}$ is independently selected at each occurrence from the group: —COR$^{13}$, —C(=O)OR$^{13}$, —C(=O)N(R$^{13}$)$_2$, —PO(OR$^{13}$)$_2$, —OR$^{13}$, and —SO$_2$OR$^{13}$;

$R^{13}$ is independently selected at each occurrence from the group: H, and $C_1$–$C_6$ alkyl;

X is selected from —O— or —NR$^5$—; and $Z^1$, $Z^2$, and $Z^3$ are independently selected from: —O—, —NH—, —CH$_2$NH—, and a direct bond.

9. A metal chelate complex of claim 8, wherein:

$R^1$, $R^2$, and $R^3$ are independently selected from: $C_1$–$C_3$ alkyl substituted with 1–2 $R^4$, $C_1$–$C_3$ fluoroalkyl substituted with 1–2 $R^4$, aryl substituted with 1–2 $R^4$, and fluoroaryl substituted with 1–2 $R^4$;

$R^5$, $R^6$ and $R^7$ are independently selected from: H, $C_1$–$C_3$ alkyl substituted with 0–2 $R^8$, $C_3$–$C_6$ cycloalkyl substituted with 0–2 $R^8$, $C_1$–$C_3$ fluoroalkyl substituted with 0–2 $R^8$, and aryl substituted with 0–2 $R^8$;

or alternatively, $R^6$ and $R^7$ may be taken together, with the atoms through which they are attached, to form a $C_3$–$C_6$ cycloalkyl substituted with 0–2 $R^8$, $C_3$–$C_6$ cycloalkenyl substituted with 0–2 $R^8$, or an aryl substituted with 0–2 $R^8$;

$R^9$ is independently selected at each occurrence from: H, $C_1$–$C_3$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, and fluorophenyl;

$A^1$, $A^2$, $A^3$, and $A^4$ are —(CR$^5$R$^5$)$_2$—;

$R^{10}$ and $R^{11}$ are independently selected at each occurrence from: H, $C_1$–$C_3$ alkyl substituted with 0–2 $R^{12}$, $C_3$–$C_6$ cycloalkyl substituted with 0–2 $R^{12}$, $C_1$–$C_3$ fluoroalkyl substituted with 0–2 $R^{12}$, $C_2$–$C_3$ alkenyl substituted with 0–2 $R^{12}$, $C_3$–$C_6$ cycloalkenyl substituted with 0–2 $R^{12}$, $C_2$–$C_3$ fluoroalkenyl substituted with 0–2 $R^{12}$, and aryl substituted with 0–2 $R^{12}$, or, alternatively, $R^{10}$ and $R^{11}$ may be taken together, with the atoms through which they are attached, to form a $C_3$–$C_{10}$cycloalkyl group substituted with 0–2 $R^{12}$, or aryl group sustituted with 0–2 $R^{12}$;

$R^{13}$ is H or $C_1$–$C_3$ alkyl; and $Z^1$, $Z^2$, and $Z^3$ are independently selected from: O, NH, and a direct bond.

10. A metal chelate complex of claim 8, wherein:

$R^1$, $R^2$, and $R^3$ are CH$_2$R$^4$;

$R^4$ is independently elected at each occurrence from: —COOH, —PO$_3$H$_2$, —SO$_3$H, and —C(=O)NR$^6$R$^7$;

$A^1$, $A^2$, $A^3$, and $A^4$ are —(CH$_2$)$_2$—; and

Q is a functional group of the formula:

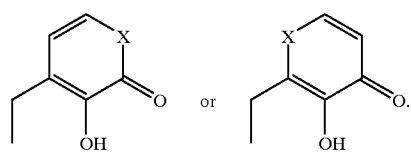

11. A metal chelate complex of claim 8, wherein:

$R^1$, $R^2$, and $R^3$ are —CH$_2$R$^4$;

$R^4$ is independently elected at each occurrence from: —COOH, —PO$_3$H$_2$, —SO$_3$H, and —C(=O)NR$^6$R$^7$;

$A^1$, $A^2$, $A^3$, and $A^4$ are —(CH$_2$)$_2$—; and

Q is a functional group of the formula:

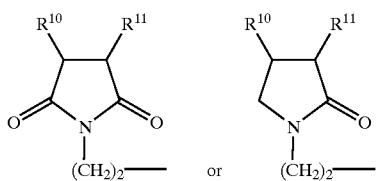

wherein R¹⁰ and R¹¹ are taken together to form a phenyl group substituted with 0–2 R¹².

12. A metal chelate complex of claim 8, wherein:

$R^1$, $R^2$, and $R^3$ are —CH$_2$R$^4$;

$R^4$ is independently elected at each occurrence from: COOH, PO$_3$H$_2$, SO$_3$H, and C(=O)NR$^6$R$^7$;

$A^1$, $A^2$, $A^3$, and $A^4$ are —(CH$_2$)$_2$—; and

Q is a functional group of the formula:

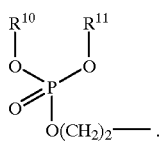

13. A metal chelate complex of claim 8 that is:

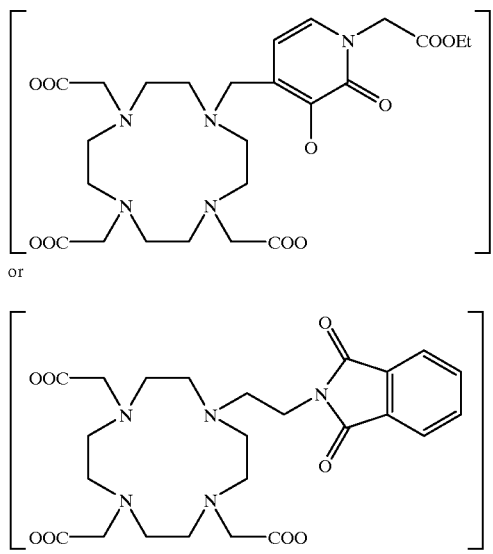

14. A metal chelate complex of claim 8 selected from the group consisting of:

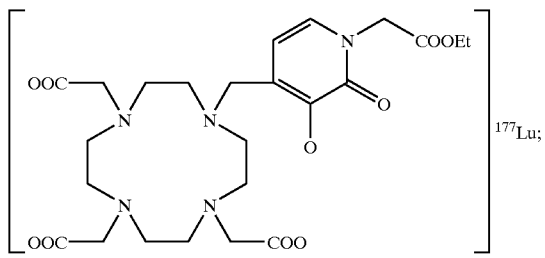

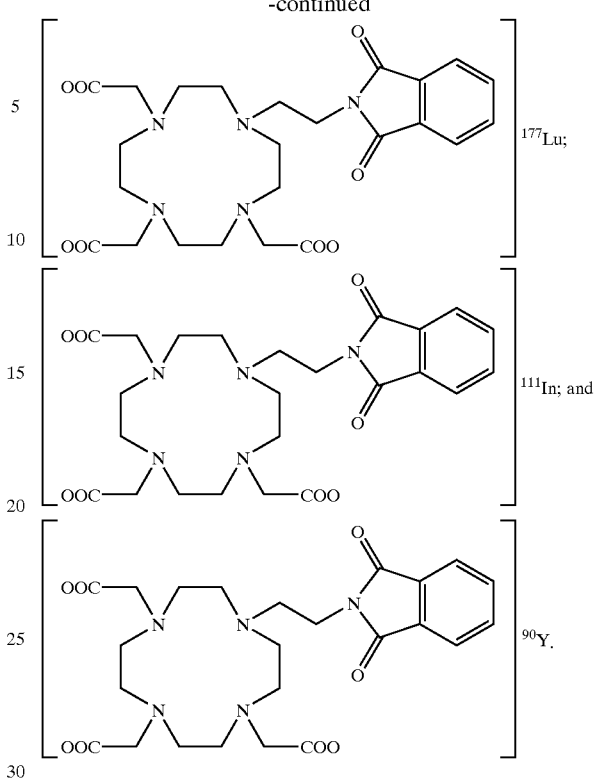

15. A novel conjugate of the formula:

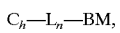

or pharmaceutically acceptable salts thereof, wherein, $C_h$ is a chelator of formula:

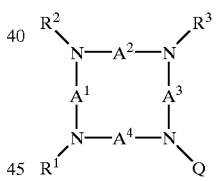

wherein:

$R^1$, $R^2$, and $R^3$ are independently selected from: C$_1$–C$_{10}$ alkyl substituted with 1–5 R$^4$, C$_1$–C$_{10}$ fluoroalkyl substituted with 1–5 R$^4$, C$_2$–C$_{10}$ alkenyl substituted with 1–5 R$^4$, C$_2$–C$_{10}$ fluoroalkenyl substituted with 1–5 R$^4$, and aryl substituted with 1–5 R$^4$, fluoroaryl substituted with 1–5 R$^4$;

$R^4$ independently selected at each occurrence from: C(=O)R$^5$, S(O)$_2$OR$^5$, C(=O)OR$^5$, C(=O)NR$^6$R$^7$, PO(OR$^6$)(OR$^7$);

$R^5$, $R^6$ and $R^7$ are independently selected from: H, a direct bond to L$_n$, C$_1$–C$_{10}$ alkyl substituted with 0–5 R$^8$, C$_2$–C$_{10}$ alkenyl substituted with 0–5 R$^8$, C$_3$–C$_{10}$ cycloalkyl substituted with 0–5 R$^8$, C$_1$–C$_{10}$ fluoroalkyl substituted with 0–5 R$^8$, C$_2$–C$_{10}$ fluoroalkenyl substituted with 0–5 R$^8$, aryl substituted with 0–5 R$^8$, and fluoroaryl substituted with 0–3 R$^8$, said C$_1$–C$_{10}$ alkyl and C$_2$–C$_{10}$ alkenyl groups optionally interrupted with O, S, NH, S(O), S(O)$_2$, P(O)(OR$^9$)O, P(O)(NHR$^9$)O, C(O)NH, NHC(O), NHC(O)NH, NHC(S)NH;

or alternatively, $R^6$ and $R^7$ may be taken together, with the atoms through which they are attached, to form a $C_3$–$C_{10}$ cycloalkyl substituted with 0–5 $R^8$, $C_3$–$C_{10}$ cycloalkenyl substituted with 0–5 $R^8$, aryl substituted with 0–5 $R^8$, or fluoroaryl substituted with 0–5 $R^8$; said $C_3$–$C_{10}$ alkyl and $C_3$–$C_{10}$ cycloalkenyl groups optionally interrupted with —O—, —S—, —$NR^9$—, —S(O)—, —S(O)$_2$—, —P(O)(O$R^9$)—, —P(O)(O$R^9$)O—, —P(O)(NH$R^9$)—, —P(O)(NH$R^9$)O—, —C(O)NH—, —NHC(O)—, —NHC(O)NH—, or —NHC(S)NH—;

$R^8$ is independently selected at each occurrence from: —H, —OH, —NH$R^9$, —C(O)$R^9$, —OC(=O)$R^9$, —OC(=O)O$R^9$, —C(=O)O$R^9$, —C(=O)N($R^9$)$_2$, —PO(O$R^9$)$_2$, —S$R^9$, —SO$R^9$, —SO$_2R^9$, —NHC(=O)$R^9$, NHC(=O)NH$R^9$, —CH$_2$O$R^9$, —NHC(=S)NH$R^9$, and a direct bond to $L_n$;

$R^9$ is independently selected at each occurrence from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, ifluorophenyl, and a direct bond to $L_n$;

$A^1$, $A^2$, $A^3$, and $A^4$ are independently —(C$R^5R^5$)$_n$—, wherein n is 2 or 3;

Q is a functional group selected from:

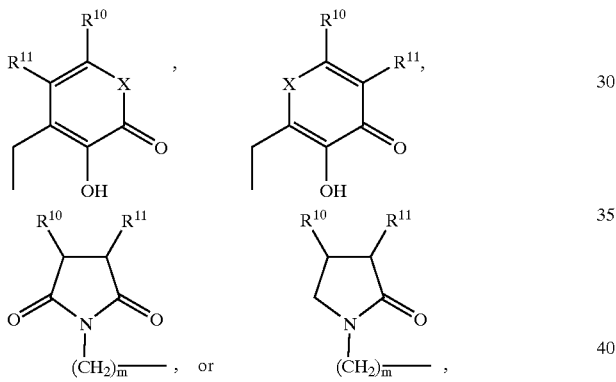

wherein:

$R^{10}$ and $R^{11}$ are independently selected at each occurrence from: H, $C_1$–$C_{10}$ alkyl substituted with 0–5 $R^{12}$, $C_3$–$C_{10}$ cycloalkyl substituted with 0–5 $R^{12}$, $C_1$–$C_{10}$ fluoroalkyl substituted with 0–5 $R^{12}$, $C_2$–$C_{10}$ alkenyl substituted with 0–5 $R^{12}$, $C_3$–$C_{10}$ cycloalkenyl substituted with 0–5 $R^{12}$, $C_2$–$C_{10}$ fluoroalkenyl substituted with 0–5 $R^{12}$, aryl substituted with 0–5 $R^{12}$, and a direct bond to $L_n$;

or, alternatively, $R^{10}$ and $R^{11}$ may be taken together with the atoms through which they are attached, to form a cyclic ring system, said ring system selected from: $C_3$–$C_{10}$ cycloalkyl substituted with 0–5 $R^{12}$, and aryl substituted with 0–3 $R^{12}$;

m is 1–3;

$R^{12}$ independently selected at each occurrence from the group: —CO$R^{13}$, —C(=O)O$R^{13}$, —C(=O)N($R^{13}$)$_2$, —PO(O$R^{13}$)$_2$, —O$R^{13}$, —SO$_2$O$R^{13}$, and a direct bond to $L_n$;

$R^{13}$ is independently selected at each occurrence from the group: H, $C_1$–$C_6$ alkyl, and a direct bond to $L_n$;

X is selected from O or N$R^5$;

$Z^1$, $Z^2$, and $Z^3$ are independently selected at each occurrence from: O, NH, CH$_2$NH, and a direct bond;

$L_n$ is a linking group of formula:

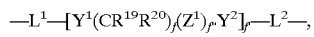

$L^1$ is —[(CH$_2$)$_g Z^1$]$_g$—(C$R^{19}R^{20}$)$_{g''}$—;

$L^2$ is —(C$R^{19}R^{20}$)$_{g''}$—[$Z^1$(CH$_2$)$_g$]$_{g'}$—;

g is independently 0–10;

g' is independently 0–1;

g" is independently 0–10;

f is independently 0–10;

f' is independently 0–10;

f" is independently 0–1;

$Y^1$ and $Y^2$ are independently selected, at each occurrence, from: a direct bond, —O—, —N$R^{20}$—, —C(=O)—, —C(=O)O—, —OC(=O)O—, —C(=O)NH—, —C(=N$R^{20}$), —S—, —S(O)—, —S(O)$_2$—, —NHC(=O)—, —(NH)$_2$C(=O)—, and —(NH)$_2$C(=S)—;

$R^{19}$ and $R^{20}$ are independently selected at each occurrence from: H, a direct bond to BM, $C_1$–$C_{10}$ alkyl substituted with 0–5 $R^{21}$, and alkaryl wherein the aryl is substituted with 0–5 $R^{21}$;

$R^{21}$ is independently selected at each occurrence from the group: —NH$R^{22}$, —C(=O)$R^{22}$, —OC(=O)$R^{22}$, —OC(=O)O$R^{22}$, —C(=O)O$R^{22}$, —C(=O)N$R_2^{22}$, —CN, —S$R^{22}$, —S(O)$R^{22}$, —S(O)$_2R^{22}$, —NHC(=O)$R^{22}$, —NHC(=O)NH$R^{22}$, —NHC(S)NH$R^{22}$, and a direct bond to BM;

$R^{22}$ is independently selected at each occurrence from the group: H, $C_1$–$C_6$ alkyl, benzyl, phenyl, and a direct bond to BM; and BM is a biologically active targeting molecule selected from the group: IIb/IIIa receptor ligands, fibrin binding peptides, leukocyte binding peptides, chemotactic peptides, LTB$_4$ receptor antagonists, somatostatin analogs, selectin binding peptides, vitronectin receptor antagonists, growth factor receptor antagonists, tyrosine kinase inhibitors, matrix metalloproteinase inhibitors, oligonucleotides, fatty acids, nitroimidazoles, and carbohydrates.

16. A conjugate of claim 15, wherein, $R^1$, $R^2$, and $R^3$ are independently selected from: $C_1$–$C_3$ alkyl substituted with 1–2 $R^4$, $C_1$–$C_3$ fluoroalkyl substituted with 1–2 $R^4$, aryl substituted with 1–2 $R^4$, and fluoroaryl substituted with 1–2 $R^4$;

$R^5$, $R^6$ and $R^7$ are independently selected from: H, a direct bond to $L_n$, $C_1$–$C_3$ alkyl substituted with 0–2 $R^8$, $C_3$–$C_6$ cycloalkyl substituted with 0–2 $R^8$, $C_1$–$C_3$ fluoroalkyl substituted with 0–2 $R^8$, and aryl substituted with 0–2 $R^8$;

or alternatively, $R^6$ and $R^7$ may be taken together, with the atoms through which they are attached, to form a $C_3$–$C_6$ cycloalkyl substituted with 0–2 $R^8$, $C_3$–$C_6$ cycloalkenyl substituted with 0–2 $R^8$, or aryl substituted with 0–2 $R^8$;

$R^9$ is independently selected at each occurrence from: H, a direct bond to $L_n$, $C_1$–$C_3$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, and fluorophenyl;

$A^1$, $A^2$, $A^3$, and $A^4$ are —(C$R^5R^5$)$_2$—;

$R^{10}$ and $R^{11}$ are independently selected at each occurrence from: H, a direct bond to $L_n$, $C_1$–$C_3$ alkyl substituted with 0–2 $R^{12}$, $C_3$–$C_6$ cycloalkyl substituted with 0–2 $R^{12}$, $C_1$–$C_3$ fluoroalkyl substituted with 0–2 $R^{12}$, $C_2$–$C_3$ alkenyl substituted with 0–2 $R^{12}$, $C_3$–$C_6$ cycloalkenyl substituted with 0–2 $R^{12}$, $C_2$–$C_3$ fluoroalkenyl substituted with 0–2 $R^{12}$, and aryl substituted with 0–2 $R^{12}$, or, alternatively, $R^{10}$ and $R^{11}$ may be taken together to form a $C_3$–$C_{10}$ cycloalkyl group substituted with 0–2 $R^{12}$, or ortho-aryl group sustituted with 0–2 $R^{12}$;

$R^{13}$ is H or $C_1$–$C_3$ alkyl; and $Z^1$, $Z^2$, and $Z^3$ are independently selected from: O, NH, and a direct bond.

17. A conjugate of claim 15, wherein:

$R^1$, $R^2$, and $R^3$ are —$CH_2R^4$;

$R^4$ is independently elected at each occurrence from: —COOH, —$PO_3H_2$, —$SO_3H$, and —C(=O)$NR^6R^7$;

$A^1$, $A^2$, $A^3$, and $A^4$ are —$(CH_2)_2$—; and

Q is a functional group of the formula:

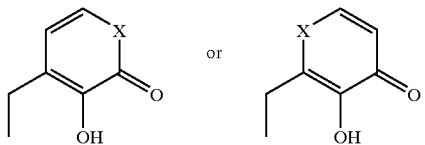 or .

18. A conjugate of claim 15, wherein:

$R^1$, $R^2$, and $R^3$ are —$CH_2R^4$;

$R^4$ is independently elected at each occurrence from: COOH, $PO_3H_2$, $SO_3H$, and C(=O)$NR^6R^7$;

$A^1$, $A^2$, $A^3$ and $A^4$ are —$(CH_2)_2$—; and

Q is a functional group of the formula:

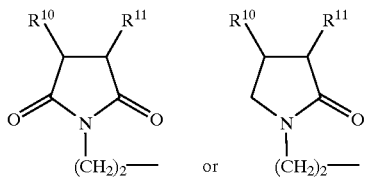

wherein:

$R^{10}$ and $R^{11}$ are taken together to form a phenyl group substituted with 0–2 $R^{12}$.

19. A conjugate of claim 15, wherein:

$R^1$, $R^2$, and $R^3$ are $CH_2R^4$;

$R^4$ is independently elected at each occurrence from: —COOH, —$PO_3H_2$, —$SO_3H$, and —C(=O)$NR^6R^7$;

$A^1$, $A^2$, $A^3$, and $A^4$ are —$(CH_2)_2$—; and

Q is a functional group of the formula:

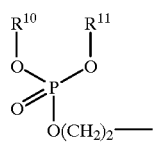

20. A novel metallopharmaceutical comprising a conjugate according to claim 15 chelated with a radionuclide selected from: $^{64}Cu$, $^{62}Cu$, $^{60}Cu$, $^{67}Cu$, $^{67}Ga$, $^{68}Ga$, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$, and $^{188}Re$, or alternatively the conjugate is chelated with a metal ion of atomic number 21–31, 39–49, 50, 56–80, 82, 83, 90.

21. A novel metallopharmaceutical according to claim 20 of the formula:

M—$C_h$—$L_n$—BM, or pharmaceutically acceptable salts thereof, wherein:

M is X or $X^1$;

wherein:

X is a radionuclide selected from: $^{64}Cu$, $^{62}Cu$, $^{60}Cu$, $^{67}Cu$, $^{67}Ga$, $^{68}Ga$, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$, and $^{188}Re$;

$X^1$ is a metal ion of atomic number 21–31, 39–49, 50, 56–80, 82, 83, 90;

$C_h$ is a chelator of formula:

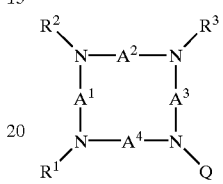

wherein:

$R^1$, $R^2$, and $R^3$ are independently selected from: $C_1$–$C_{10}$ alkyl substituted with 1–5 $R^4$, $C_1$–$C_{10}$ fluoroalkyl substituted with 1–5 $R^4$, $C_2$–$C_{10}$ alkenyl substituted with 1–5 $R^4$, $C_2$–$C_{10}$ fluoroalkenyl substituted with 1–5 $R^4$, and aryl substituted with 1–5 $R^4$, fluoroaryl substituted with 1–5 $R^4$;

$R^4$ independently selected at each occurrence from: C(=O)$R^5$, S(O)$_2OR^5$, C(=O)$OR^5$, C(=O)$NR^6R^7$, PO($OR^6$)($OR^7$);

$R^5$, $R^6$ and $R^7$ are independently selected from: H, a direct bond to $L_n$, $C_1$–$C_{10}$ alkyl substituted with 0–5 $R^8$, $C_2$–$C_{10}$ alkenyl substituted with 0–5 $R^8$, $C_3$–$C_{10}$ cycloalkyl substituted with 0–5 $R^8$, $C_1$–$C_{10}$ fluoroalkyl substituted with 0–5 $R^8$, $C_2$–$C_{10}$ fluoroalkenyl substituted with 0–5 $R^8$, aryl substituted with 0–5 $R^8$, and fluoroaryl substituted with 0–3 $R^8$ said $C_1$–$C_{10}$ alkyl and $C_2$–$C_{10}$ alkenyl groups optionally interrupted with —O—, —S—, —NH—, —S(O)—, —S(O)$_2$, —P(O)(OR$^9$)O—, —P(O)(NHR$^9$)O—, —C(O)NH—, —NHC(O)—, —NHC(O)NH—, —NHC(S)NH—;

or alternatively, $R^6$ and $R^7$ may be taken together, with the atoms through which they are attached, to form a $C_3$–$C_{10}$ cycloalkyl substituted with 0–5 $R^8$, $C_3$–$C_{10}$ cycloalkenyl substituted with 0–5 $R^8$, aryl substituted with 0–5 $R^8$, or fluoroaryl substituted with 05–8; said $C_3$–$C_{10}$ alkyl and $C_3$–$C_{10}$ cycloalkenyl groups optionally interrupted with O, S, $NR^9$, S(O), S(O)$_2$, P(O)(OR$^9$), P(O)(OR$^9$)O, P(O)(NHR$^9$), P(O)(NHR$^9$)O, C(O)NH, NHC(O), NHC(O)NH, NHC(S)NH;

$R^8$ independently selected at each occurrence from: H, OH, NHR$^9$, C(=O)R$^9$, OC(=O)R$^9$, OC(=O)OR$^9$, C(=O)OR$^9$, C(=O)N(R$^9$)$_2$, PO(OR$^9$)$_2$, SR$^9$, SOR$^9$, SO$^2$R$^9$, NHC(=O)R$^9$, NHC(=O)NHR$^9$, CH$_2$OR$^9$, NHC(=S)NHR$^9$, and a direct bond to $L_n$;

$R^9$ is independently selected at each occurrence from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, fluorophenyl, and a direct bond to $L_n$;

$A^1$, $A^2$, $A^3$, and $A^4$ are independently —(CR$^5$R$^5$)$_n$—, wherein n is 2 or 3;

Q is a functional group selected from:

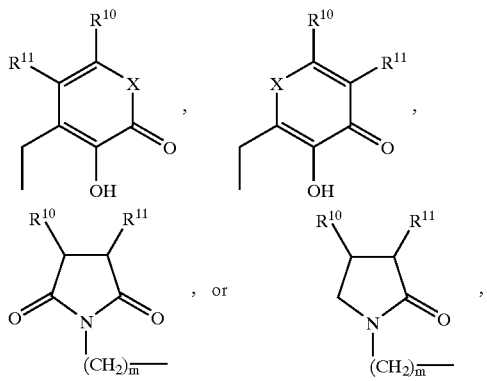

wherein:
R$^{10}$ and R$^{11}$ are independently selected at each occurrence from: H, C$_1$–C$_{10}$ alkyl substituted with 0–5 R$^{12}$, C$_3$–C$_{10}$ cycloalkyl substituted with 0–5 R$^{12}$, C$_1$–C$_{10}$ fluoroalkyl substituted with 0–5 R$^{12}$, C$_2$–C$_{10}$ alkenyl substituted with 0–5 R$^{12}$, C$_3$–C$_{10}$ cycloalkenyl substituted with 0–5 R$^{12}$, C$_2$–C$_{10}$ fluoroalkenyl substituted with 0–5 R$^{12}$, aryl substituted with 0–5 R$^{12}$, and a direct bond to L$_n$;

or, alternatively, R$^{10}$ and R$^{11}$ may be taken together, with the atoms through which they are attached, to form a cyclic ring system, said ring system selected from: C$_3$–C$_{10}$ cycloalkyl substituted with 0–5 R$^{12}$ and aryl substituted with 0–3 R$^{12}$;

m is 1–3;

R$^{12}$ is independently selected at each occurrence from the group: COR$^{13}$, C(=O)OR$^{13}$, C(O)N(R$^{13}$)$_2$, PO(OR$^{13}$)$_2$, OR$^{13}$, SO$_2$OR$^{13}$, and a direct bond to L$_n$;

R$^{13}$ is independently selected at each occurrence from the group: H, C$_1$–C$_6$ alkyl, and a direct bond to L$_n$;

X is selected from O or NR$^5$;

Z$^1$, Z$^2$, and Z$^3$ are independently selected at each occurrence from: O, NH, CH$_2$NH, and a direct bond;

L$_n$ is a linking group of formula:

L$^1$ is —[(CH$_2$)$_g$Z$^1$]$_{g'}$—(CR$^{19}$R$^{20}$)$_{g''}$—;
L$^2$ is —(CR$^{19}$R$^{20}$)$_{g''}$—[Z$^1$(CH$^2$)$_g$]$_{g'}$—;
g is independently 0–10;
g' is independently 0–1;
g'' is independently 0–10;
f is independently 0–10;
f' is independently 0–10;
f'' is independently 0–1;
Y$^1$ and Y$^2$ are independently selected at each occurrence from: a direct bond, —O—, —NR$^{20}$—, —C=O—, —C(=O)O—, —OC(=O)O—, —C(=O)NH—, —C(=NR$^{20}$)—, —S—, —S(O)—, —S(O)$_2$—, —NHC(=O)—, —(NH)$_2$C(=O)—, and —(NH)$_2$(C=S)—;

R$^{19}$ and R$^{20}$ are independently selected at each occurrence from: H, a direct bond to BM, C$_1$–C$_{10}$ alkyl substituted with 0–5 R$^{21}$, and alkaryl wherein the aryl is substituted with 0–5 R$^{21}$;

R$^{21}$ is independently selected at each occurrence from the group: —NHR$^{22}$, —C(=O)R$^{22}$, —OC(=O)R$^{22}$, —OC(=O)OR$^{22}$, —C(=O)OR$^{22}$, —C(=O)NR$_2^{22}$, —CN, —SR$_{22}$, —S(O)R$^{22}$, —S(O)$_2$R$^{22}$, —NHC(=O)R$^{22}$, —NHC(=O)NHR$^{22}$, —NHC(=S)NHR$^{22}$, and a direct bond to BM;

R$^{22}$ is independently selected at each occurrence from the group: H, C$_1$–C$_6$ alkyl, benzyl, phenyl, and a direct bond to BM; and BM is a biologically active targeting molecule selected from the group: IIb/IIIa receptor ligands, fibrin binding peptides, leukocyte binding peptides, chemotactic peptides, LTB$_4$ receptor antagonists, somatostatin analogs, selectin binding peptides, vitronectin receptor antagonists, growth factor receptor antagonists, tyrosine kinase inhibitors, matrix metalloproteinase inhibitors, oligonucleotides, fatty acids, nitroimidazoles, and carbohydrates.

22. A metallopharmaceutical of claim 21, wherein,

R$^1$, R$^2$, and R$^3$ are independently selected from: C$_1$–C$_3$ alkyl substituted with 1–2 R$^4$, C$_1$–C$_3$ fluoroalkyl substituted with 1–2 R$^4$, aryl substituted with 1–2 R$^4$, and fluoroaryl substituted with 1–2 R$^4$;

R$^5$, R$^6$ and R$^7$ are independently selected from: H, a direct bond to L$_n$, C$_1$–C$_3$ alkyl substituted with 0–2 R$^8$, C$_3$–C$_6$ cycloalkyl substituted with 0–2 R$^8$, C$_1$–C$_3$ fluoroalkyl substituted with 0–2 R$^8$, and aryl substituted with 0–2 R$^8$;

or alternatively, R$^6$ and R$^7$ may be taken together, with the atoms through which they are attached, to form a C$_3$–C$_6$ cycloalkyl substituted with 0–2 R$^8$, C$_3$–C$_6$ cycloalkenyl substituted with 0–2 R$^8$, or aryl substituted with 0–2 R$^8$;

R$^9$ is independently selected at each occurrence from: H, a direct bond to L$_n$, C$_1$–C$_3$ alkyl, C$_3$–C$_6$ cycloalkyl, C$_1$–C$_6$ fluoroalkyl, C$_1$–C$_6$ alkenyl, C$_3$–C$_6$ cycloalkyl, C$_1$–C$_6$ fluoroalkenyl, benzyl, fluorobenzyl, phenyl, and fluorophenyl;

A$^1$, A$^2$, A$^3$, and A$^4$ are —(CR$^5$R$^5$)$_2$—;

R$^{10}$ and R$^{11}$ are independently selected at each occurrence from: H, a direct bond to L$_n$, C$_1$–C$_3$ alkyl substituted with 0–2 R$^{12}$, C$_3$–C$_6$ cycloalkyl substituted with 0–2 R$^{12}$, C$_1$–C$_3$ fluoroalkyl substituted with 0–2 R$^{12}$, C$_2$–C$_3$ alkenyl substituted with 0–2 R$^{12}$, C$_3$–C$_6$ cycloalkenyl substituted with 0–2 R$^{12}$, C$_2$–C$_3$ fluoroalkenyl substituted with 0–2 R$^{12}$, and aryl substituted with 0–2 R$^{12}$, or, alternatively, R$^{10}$ and R$^{11}$ may be taken together, with the atoms through which they are attached, to form a C$_3$–C$_{10}$ cycloalkyl group substituted with 0–2 R$^{12}$, or ortho-aryl group sustituted with 0–2 R$^{12}$;

R$^{13}$ is H or C$_1$–C$_3$ alkyl; and

Z$^1$, Z$^2$, and Z$^3$ are independently selected from: O, NH, and a direct bond.

23. A metallopharmaceutical of claim 21, wherein:

R$^1$, R$^2$, and R$^3$ are —CH$_2$R$^4$;

R$^4$ is independently elected at each occurrence from: COOH, —PO$_3$H$_2$, —SO$_3$H, and —C(=O)NR$^6$R$^7$;

A$^1$, A$^2$, A$^{3,}$ and A$^4$ are —(CH$_2$)$_2$—; and

Q is a functional group of the formula:

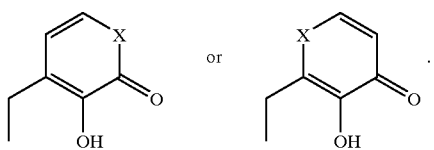

24. A metallopharmaceutical of claim 21, wherein:
$R^1$, $R^2$, and $R^3$ are $—CH_2R^4$;
$R^4$ is independently elected at each occurrence from: $—COOH$, $—PO_3H_2$, $—SO_3H$, and $—C(O)NR^6R^7$;
$A^1$, $A^2$, $A^3$, and $A^4$ are $—(CH_2)_2—$; and
Q is a functional group of the formula:

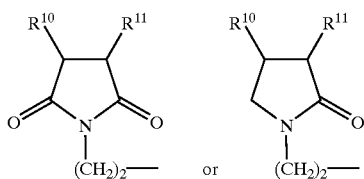

wherein $R^{10}$ and $R^{11}$ are taken together to form a phenyl group substituted with 0–2 $R_{12}$.

25. A metallopharmaceutical of claim 21, wherein:
$R^1$, $R^2$, and $R^3$ are $—CH_2R^4$;
$R^4$ is independently elected at each occurrence from: $COOH$, $PO_3H_2$, $SO_3H$, and $C(=O)NR^6R^7$;
$A^1$, $A^2$, $A^3$, and $A^4$ are $—(CH_2)_2—$; and
Q is a functional group of the formula:

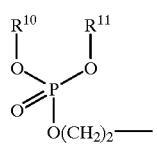

26. A metallopharmaceutical composition comprising a metallopharmaceutical of claim 20 and a pharmaceutically acceptable carrier.

27. A method of treating cancer in a patient comprising administering to a patient in need thereof a therapeutically effective amount of a metallopharmaceutical composition of claim 26, wherein: BM is a biologically active targeting molecule selected from the group: vitronectin receptor antagonists, growth factor receptor antagonists, matrix metalloproteinase inhibitors and tyrosine kinase inhibitors; and the metal is a radionuclide selected from the group consisiting of radionuclide selected from: $^{64}Cu$, $^{62}Cu$, $^{60}Cu$, $^{67}Cu$, $^{67}Ga$, $^{68}Ga$, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$, and $^{188}Re$.

28. A method of diagnosing thromboembolic disorders or atherosclerosis in a patient, comprising:
(i) administering to said patient a diagnostic effective amount of a metallopharmaceutical of claim 21; and
(ii) generating a radioimage of at least a part of said patient's body;
wherein BM is a IIb/IIIa receptor ligand or fibrin binding peptide; and
M is $^{62}Cu$, $^{60}Cu$, $^{67}Ga$, $^{68}Ga$, $^{99m}Tc$, or $^{111}In$.

29. A method of diagnosing thromboembolic disorders or atherosclerosis in a patient, comprising:
(i) administering to said patient a diagnostic effective amount of a metallopharmaceutical of claim 21; and
(ii) generating a MRI image of at least a part of said patient's body;
wherein BM is a IIb/IIIa receptor ligand or fibrin binding peptide; and
M is paramagnetic metal ion of atomic number 21–29, 42–44 or 58–70.

30. A method of diagnosing thromboembolic disorders or atherosclerosis in a patient, comprising:
(i) administering to said patient a diagnostic effective amount of a metallopharmaceutical of claim 21; and
(ii) generating an X-ray or CT image of at least a part of said patient's body;
wherein BM is a IIb/IIIa receptor ligand or fibrin binding peptide; and
M is heavy metal ion of atomic number 21–31, 39–49, 50, 56–80, 82, 83, 90.

31. A method of diagnosing infection, inflammation or transplant rejection in a patient, comprising:
(i) administering to said patient a diagnostic effective amount of a metallopharmaceutical of claim 21; and
(ii) generating a radioimage of at least a part of said patient's body;
wherein BM is selected from the group consisting of a leukocyte binding peptide, a chemotactic peptide, and a $LTB_4$ receptor antagonist; and
M is $^{62}Cu$, $^{60}Cu$, $^{67}Ga$, $^{68}Ga$, $^{99m}Tc$, or $^{111}In$.

32. A method of diagnosing infection, inflammation or transplant rejection in a patient, comprising:
(i) administering to said patient a diagnostic effective amount of a metallopharmaceutical of claim 21; and
(ii) generating a MRI image of at least a part of said patient's body;
wherein BM is selected from the group consisting of a leukocyte binding peptide, a chemotactic peptide, and a $LTB_4$ receptor antagonist; and
M is paramagnetic metal ion of atomic number 21–29, 42–44 or 58–70.

33. A method of diagnosing infection, inflammation or transplant rejection in a patient, comprising:
(i) administering to said patient a diagnostic effective amount of a metallopharmaceutical of claim 21; and
(ii) generating an X-ray or CT image of at least a part of said patient's body;
wherein BM is selected from the group consisting of a leukocyte binding peptide, a chemotactic peptide, and a $LTB_4$ receptor antagonist; and
M is heavy metal ion of atomic number 21–31, 39–49, 50, 56–80, 82, 83, 90.

34. A method of detecting new angiogenic vasculature in a patient, comprising:
(i) administering to said patient a diagnostic effective amount of a metallopharmaceutical of claim 21; and
(ii) generating a radioimage of at least a part of said patient's body;
wherein BM is a vitronectin receptor antagonist, a somatostatin analog, or a growth factor receptor antagonist; and
M is $^{62}Cu$, $^{60}Cu$, $^{67}Ga$, $^{68}Ga$, $^{99m}Tc$, or $^{111}In$.

35. A method of detecting new angiogenic vasculature in a patient, comprising:
(i) administering to said patient a diagnostic effective amount of a metallopharmaceutical of claim 21; and (ii) generating a MRI image of at least a part of said patient's body;
wherein BM is a vitronectin receptor antagonist, a somatostatin analog, or a growth factor receptor antagonist; and M is paramagnetic metal ion of atomic number 21–29, 42–44 or 58–70.

36. A method of detecting new angiogenic vasculature in a patient, comprising:
(i) administering to said patient a diagnostic effective amount of a metallopharmaceutical of claim 21; and
(ii) generating an X-ray or CT image of at least a part of said patient's body;
wherein BM is a vitronectin receptor antagonist, a somatostatin analog, or a growth factor receptor antagonist; and M is heavy metal ion of atomic number 21–31, 39–49, 50, 56–80, 82, 83, 90.

37. A method of metal detoxification in a patient comprising administering to a patient in need thereof a detoxifying amount of a compound according to claim 1, or a weak chelate complex or salt form thereof, with a pharmaceutically acceptable counterion.

38. A kit for preparing a metallopharmaceutical composition, comprising the following components:
(i) a conjugate of claim 15;
(ii) a pharmaceutically acceptable carrier, a formulating agent, or an adjuvant;
(iii) a solution of a salt of a metal, or chelate of a metal; and
(iv) instructions for reacting the components present in the kit;
wherein the metal is selected from the group consisting of a metal ion of atomic number 21–31, 39–49, 50, 56–80, 82, 83, or 90.

39. A kit for forming a radiopharmaceutical complex comprising the following components:
(i) a conjugate of claim 15;
(ii) optionally a reducing agent; and
(iii) instructions for reacting the components of said kit with a radionuclide solution.

40. (Added) A compound of formula:

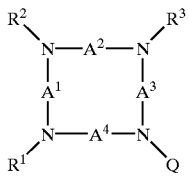

or pharmaceutically acceptable salts thereof
wherein:
$R^1$, $R^2$, and $R^3$ are independently selected from: $C_1$–$C_{10}$ alkyl substituted with 1–5 $R^4$, $C_1$–$C_{10}$ fluoroalkyl substituted with 1–5 $R^4$, $C_2$–$C_{10}$ alkenyl substituted with 1–5 $R^4$, $C_2$–$C_{10}$ fluoroalkenyl substituted with 1–5 $R^4$, and aryl substituted with 1–5 $R^4$, fluoroaryl substituted with 1–5 $R^4$;

$R^4$ is independently selected at each occurrence from: $C(=O)R^5$, $S(O)_2OR^5$, $C(=O)OR^5$, $C(=O)NR^6R^7$, $PO(OR^6)(OR^7)$;

$R^5$, $R^6$ and $R^7$ are independently selected from: H, $C_1$–$C_{10}$ alkyl substituted with 0–5 $R^8$, $C_2$–$C_{10}$ alkenyl substituted with 0–5 $R^8$, $C_3$–$C_{10}$ cycloalkyl substituted with 0–5 $R^8$, $C_1$–$C_{10}$ fluoroalkyl substituted with 0–5 $R^8$, $C_2$–$C_{10}$ fluoroalkenyl substituted with 0–5 $R^8$, aryl substituted with 0–5 $R^8$, and fluoroaryl substituted with 0–3 $R^8$ and groups, said $C_1$–$C_{10}$ alkyl $C_2$–$C_{10}$ alkenyl optionally interrupted with —O—, —S—, —NH—, —S(O)—, =S(O)$_2$—, —P(O)(OR$^9$)O—, —P(O)(NHR$^9$)O—, —C(O)NH—, —NHC(O)—, —NHC(O)NH—, or —NHC(S)NH—;

or alternatively, $R^6$ and $R^7$ may be taken together, with the atoms through which they are attached, to form a $C_3$–$C_{10}$ cycloalkyl substituted with 0–5 $R^8$, $C_3$–$C_{10}$ cycloalkenyl substituted with 0–5 $R^8$, aryl substituted with 0–5 $R^8$, or fluoroaryl substituted with 0–5 $R^8$; said $C_3$–$C_{10}$ alkyl and $C_3$–$C_{10}$ cycloalkenyl groups optionally interrupted with —O—, —S—, —NR$^9$—, —S(O)—, —S(O)$_2$—, —P(O)(OR$^9$)—, —P(O)(OR$^9$)O—, —P(O)(NHR$^9$)—, —P(O)(NHR$^9$)O—, —C(O)NH—, —NHC(O)—, —NHC(O)NH—, or —NHC(S)NH—;

$R^8$ independently selected at each occurrence from: H, —OH, —NHR$^9$, —C(=O)R$^9$, —OC(=O)R$^9$, —OC(=O)OR$^9$, —C(=O)OR$^9$, —C(=O)N(R$^9$)$_2$, —PO(OR$^9$)$_2$, —SR$^9$, —SOR$^9$, —SO$_2$R$^9$, —NHC(=O)R$^9$, —NHC(=O)NHR$^9$, —CH$_2$OR$^9$, and —NHC(=S)NHR$^9$;

$R^9$ is independently selected at each occurrence from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, and fluorophenyl;

$A^1$, $A^2$, $A^3$, and $A^4$ are independently —(CR$^5$R$^5$)$_n$—, wherein n is 2 or 3.

Q is a functional group:

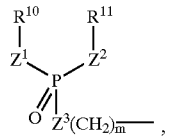

wherein $R^{10}$ and $R^{11}$ are independently selected at each occurrence from: H, $C_1$–$C_{10}$ alkyl substituted with 0–5 $R^{12}$, $C_3$–$C_{10}$ cycloalkyl substituted with 0–5 $R^{12}$, $C_1$–$C_{10}$ fluoroalkyl substituted with 0–5 $R^{12}$, $C_2$–$C_{10}$ alkenyl substituted with 0–5 $R^{12}$, $C_3$–$C_{10}$ cycloalkenyl substituted with 0–5 $R^{12}$, $C_2$–$C_{10}$ fluoroalkenyl substituted with 0–5 $R^{12}$, and aryl substituted with 0–5 $R^{12}$, or, alternatively, $R^{10}$ and $R^{11}$ may be taken together, with the atoms through which they are attached, to form a cyclic ring system, said ring system selected from: $C_3$–$C_{10}$ cycloalkyl substituted with 0–5 $R^{12}$, and aryl substituted with 0–3 $R^{12}$;

m is 1–3;

$R^{12}$ is independently selected at each occurrence from the group: COR$^{13}$, C(=O)OR$^{13}$, C(=O)N(R$^{13}$)$_2$, PO(OR$^{13}$)$_2$, OR$^{13}$, and SO$_2$OR$^{13}$;

$R^{13}$ is independently selected at each occurrence from the group: H, and $C_1$–$C_6$ *alkyl*;

X is selected from O or NR$^5$; and $Z^1$, $Z^2$, and $Z^3$ are independently selected from: O, NH, CH$_2$NH, and a direct bond, with the proviso that when $Z^3$ is a direct bond at least one of $Z^1$ and $Z^2$ is NH or CH$_2$NH.

41. A metal chelate complex comprising a compound according to claim 40 complexed to a metal ion of atomic number 21–31, 39–49, 50, 56–80, 82, 83, 90, or alternatively, the compound is complexed to a radionuclide selected from: $^{64}$Cu, $^{62}$Cu, $^{60}$Cu, $^{67}$Cu, $^{67}$Ga, $^{68}$Ga, $^{99m}$Tc, $^{111}$In, $^{90}$Y, $^{149}$Pr, $^{153}$Sm, $^{159}$Gd, $^{166}$Lu, $^{169}$Yb, $^{177}$Lu, $^{186}$Re, and $^{188}$Re.

42. A novel conjugate of the formula:

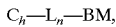

or pharmaceutically acceptable salts thereof,
wherein,
$C_h$ is a chelator of formula:

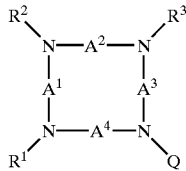

wherein:
- $R^1$, $R^2$, and $R^3$ are independently selected from: $C_1$–$C_{10}$ alkyl substituted with 1–5 $R^4$, $C_1$–$C_{10}$ fluoroalkyl substituted with 1–5 $R^4$, $C_2$–$C_{10}$ alkenyl substituted with 1–5 $R^4$, $C_2$–$C_{10}$ fluoroalkenyl substituted with 1–5 $R^4$, and aryl substituted with 1–5 $R^4$, fluoroaryl substituted with 1–5 $R^4$;
- $R^4$ is independently selected at each occurrence from: $C(=O)R^5$, $S(O)_2OR^5$, $C(=O)OR^5$, $C(=O)NR^6R^7$, $PO(OR^6)(R^7)$;
- $R^5$, $R^6$ and $R^7$ are independently selected from: H, a direct bond to $L_n$, $C_1$–$C_{10}$ alkyl substituted with 0–5 $R^8$, $C_2$–$C_{10}$ alkenyl substituted with 0–5 $R^8$, $C_3$–$C_{10}$ cycloalkyl substituted with 0–5 $R^8$, $C_1$–$C_{10}$ fluoroalkyl substituted with 0–5 $R^8$, $C_2$–$C_{10}$ fluoroalkenyl substituted with 0–5 $R^8$, aryl substituted with 0–5 $R^8$, and fluoroaryl substituted with 0–3 $R^8$, said $C_1$–$C_{10}$ alkyl and $C_2$–$C_{10}$ alkenyl groups optionally interrupted with O, S, NH, S(O), S(O)$_2$, P(O)(OR$^9$), P(O)(NHR$^9$)O, C(O)NH, NHC(O), NHC(O)NH, NHC(S)NH;
- or alternatively, $R^6$ and $R^7$ may be taken together, with the atoms through which they are attached, to form a $C_3$–$C_{10}$ cycloalkyl substituted with 0–5 $R^8$, $C_3$–$C_{10}$ cycloalkenyl substituted with 0–5 $R^8$, aryl substituted with 0–5 $R^8$ or fluoroaryl substituted with 0–5 $R^8$; said $C_3$–$C_{10}$ alkyl and $C_3$–$C_{10}$ cycloalkenyl groups optionally interrupted with —O—, —S—, —NR$^9$—, —S(O)—, —S(O)$_2$—, —P(O)(OR$^9$)—, —P(O)(OR$^9$)O—, —P(O)(NHR$^9$)—, —P(O)(NHR$^9$)O—, —C(O)NH—, —NHC(O)—, —NHC(O)NH—, or —NHC(S)NH—;
- $R^8$ is independently selected at each occurrence from: —H, —OH, —NHR$^9$, —C(O)R$^9$, —OC(=O)R$^9$, —OC(=O)OR$^9$, —C(=O)OR$^9$, —C(=O)N(R$^9$)$_2$, —PO(OR$^9$)$_2$, —SR$^9$, —SOR$^9$, —SO$_2$R$^9$, —NHC(=O)R$^9$, NHC(=O)NHR$^9$, —CH$_2$OR$^9$, —NHC(=S)NHR$^9$, and a direct bond to $L_n$;
- $R^9$ is independently selected at each occurrence from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl, fluorophenyl, and a direct bond to $L_n$;
- $A^1$, $A^2$, $A^3$, and $A^4$ are independently —(CR$^5$R$^5$)$_n$—, wherein n is 2 or 3;
- Q is a functional group:

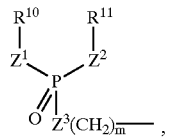

wherein:
- $R^{10}$ and $R^{11}$ are independently selected at each occurrence from: H, $C_1$–$C_{10}$ alkyl substituted with 0–5 $R^{12}$, $C_3$–$C_{10}$ cycloalkyl substituted with 0–5 $R^{12}$, $C_1$–$C_{10}$ fluoroalkyl substituted with 0–5 $R^{12}$, $C_2$–$C_{10}$ alkenyl substituted with 0–5 $R^{12}$, $C_3$–$C_{10}$ cycloalkenyl substituted with 0–5 $R^{12}$, $C_2$–$C_{10}$ fluoroalkenyl substituted with 0–5 $R^{12}$, aryl substituted with 0–5 $R^{12}$, and a direct bond to $L_n$;
- or, alternatively, $R^{10}$ and $R^{11}$ may be taken together with the atoms through which they are attached, to form a cyclic ring system, said ring system selected from: $C_3$–$C_{10}$ cycloalkyl substituted with 0–5 $R^{12}$ and aryl substituted with 0–3 $R^{12}$;
- m is 1–3;
- $R^{12}$ is independently selected at each occurrence from the group: —COR$^{13}$, —C(=O)OR$^{13}$, —C(=O)N(R$^{13}$)$_2$, —PO(OR$^{13}$)$_2$, —OR$^{13}$, —SO$_2$OR$^{13}$, and a direct bond to $L_n$;
- $R^{13}$ is independently selected at each occurrence from the group: H, $C_1$–$C_6$ alkyl, and a direct bond to $L_n$;
- X is selected from O or NR$^5$;
- $Z^1$, $Z^2$, and $Z^3$ are independently selected from: O, NH, CH$_2$NH, and a direct bond, with the proviso that when $Z^3$ a direct bond at least one of $Z^1$ and $Z^2$ NH or CH$_2$NH;
- $L_n$ is a linking group of formula:

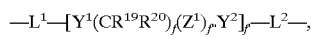

- $L^1$ is —[(CH$_2$)$_g$Z$^1$]$_g$—;
- $L^2$ is —(CR$^{19}$R$_{20}$)$_{g''}$—[Z$^1$(CH$_2$)$_g$]$_{g'}$—;
- g is independently 0–10;
- g' is independently 0–1;
- g" is independently 0–10;
- f is independently 0–10;
- f' is independently 0–10;
- f" is independently 0–1;
- $Y^1$ and $Y^2$ are independently selected, at each occurrence, from: a direct bond, —O—, —NR$_{20}$—, —C(=O)—, —C(=O)O—, —OC(=O)O—, —C(=O)NH—, —C(=NR$^{20}$), —S—, —S(O)—, —S(O)$_2$—, —NHC(=O)—, —(NH)$_2$C(O)—, and —(NH)$_2$C(=S)—;
- $R^{19}$ and $R^{20}$ are independently selected at each occurrence from: H, a direct bond to BM, $C_1$–$C_{10}$ alkyl substituted with 0–5 $R^{21}$, and alkaryl wherein the aryl is substituted with 0–5 $R^{21}$;
- $R^{21}$ is independently selected at each occurrence from the group: —NHR$^{22}$, —C(=O)R$^{22}$, —OC(=O)R$^{22}$, —OC(=O)OR$^{22}$, —C(=O)OR$^{22}$, —C(=O)NR$_2^{22}$, —CN, —SR$^{22}$, —S(O)R$^{22}$, —S(O)$_2$R$^{22}$, —NHC(=O)R$^{22}$, —NHC(=O)NHR$^{22}$, —NHC(S)NHR$^{22}$, and a direct bond to BM;
- $R^{22}$ is independently selected at each occurrence from the group: H, $C_1$–$C_6$ alkyl, benzyl, phenyl, and a direct bond to BM; and BM is a biologically active targeting molecule selected from the group: IIb/IIIa receptor ligands, fibrin binding peptides, leukocyte binding peptides, chemotactic peptides, $LTB_4$ receptor antagonists, somatostatin analogs, selectin binding peptides, vitronectin receptor antagonists, growth factor receptor antagonists, tyrosine kinase inhibitors, matrix metalloproteinase inhibitors, oligonucleotides, fatty acids, nitroimidazoles, and carbohydrates.

43. A novel metallopharmaceutical comprising a conjugate according to claim 42 chelated with a radionuclide selected from: $^{64}Cu$, $^{62}Cu$, $^{60}Cu$, $^{67}Cu$, $^{67}Ga$, $^{68}Ga$, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$, and $^{188}Re$, or alternatively the conjugate is chelated with a metal ion of atomic number 21–31, 39–49, 50, 56–80, 82, 83, 90.

\* \* \* \* \*